(12) United States Patent
Liu et al.

(10) Patent No.: US 10,858,446 B2
(45) Date of Patent: Dec. 8, 2020

(54) ANTI-PCSK9 ANTIBODIES AND USES THEREOF

(71) Applicant: PharmaExplorer Limited, Tortola (VG) (GB)

(72) Inventors: Lile Liu, Shanghai (CN); Jing Gao, Shanghai (CN); Xinxiu Yang, Shanghai (CN); Zhiqiang Xu, Shanghai (CN); Shaoping Hu, Shanghai (CN); Lini Huang, Shanghai (CN); Hongzhuan Gu, Shanghai (CN); Yu Zhang, Shanghai (CN); Yangyang Zhai, Shanghai (CN); Tatchi Teddy Yang, Shanghai (CN)

(73) Assignee: PHARMAEXPLORER LIMITED, Tortola (VG)

( * ) Notice: Subject to any disclaimer, the term of this patent is extended or adjusted under 35 U.S.C. 154(b) by 323 days.

(21) Appl. No.: 15/768,032

(22) PCT Filed: Oct. 14, 2016

(86) PCT No.: PCT/CN2016/102209
§ 371 (c)(1),
(2) Date: Apr. 13, 2018

(87) PCT Pub. No.: WO2017/063593
PCT Pub. Date: Apr. 20, 2017

(65) Prior Publication Data
US 2018/0355059 A1 Dec. 13, 2018

(30) Foreign Application Priority Data
Oct. 16, 2015 (CN) .......................... 2015 1 0673316

(51) Int. Cl.
*C07K 16/40* (2006.01)
*C07K 16/46* (2006.01)
*A61K 39/395* (2006.01)
*A61K 39/00* (2006.01)

(52) U.S. Cl.
CPC ............ *C07K 16/40* (2013.01); *A61K 39/395* (2013.01); *A61K 39/39591* (2013.01); *C07K 16/46* (2013.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

2014/0044730 A1   2/2014   Yancopoulos et al.

FOREIGN PATENT DOCUMENTS

| WO | 2008057459 A2 | 5/2008 |
| WO | 2010077854 A1 | 7/2010 |
| WO | 2011053759 A1 | 5/2011 |
| WO | 2014209384 A1 | 12/2014 |

OTHER PUBLICATIONS

Partial Supplementary European Search Report dated Mar. 25, 2019 in EP Application No. 16854969.9.
Stein et al., "Reduction of Low-Density Lipoprotein Cholesterol by Monoclonal Antibody Inhibition of PCSK9," Annual Review of Medicine, vol. 65, No. 1, pp. 417-431 (Jan. 14, 2014).
Mozaffarian et al., "Heart Disease and Stroke Statistics—2015 Update a Report from the American Heart Association", Downloaded from http://Circ.ahajournals.org, pp. e29-e417, Jan. 27, 2015.
Harding et al., "Class Switching in Human Immunoglobulin transgenic Mice" Annals New York Academy of Sciences, pp. 536-546, 2008.
Lonberg et al, "Antigen-specific Human Antibodies from Mice Comprising Four Distinct Genetic Modifications", Nature—vol. 368, pp. 856-859, Apr. 1994.
Lonberg et al., "Human Antibodies from Transgenic Mice", Intern. Rev. Immunol., vol. 13, pp. 65-93, 1995.
Gencer et al., "PCSK9 Inhibitors", Swiss Medical Weekly, pp. 1-9, Apr. 9, 2015.
Rallidis et al., "PCSK9 Inhibition as an Emerging Lipid Lowering therapy: Unanswered Questions", Hellenic Journal of Cardiology, pp. 1-6, Jan. 2016.
Int'l Search Report dated Jan. 18, 2017 in Int'l Application No. PCT/CN2016/102209.

*Primary Examiner* — Sharon X Wen
(74) *Attorney, Agent, or Firm* — Panitch Schwarze Belisario & Nadel LLP; Stephany G. Small; Lars H. Genieser

(57) ABSTRACT

Anti-PCSK9 antibodies and antigen-binding fragments thereof are described. Also described are nucleic acids encoding the antibodies, compositions comprising the antibodies, and methods of producing the antibodies and using the antibodies for treating or preventing diseases such as lipid disorders, metabolic diseases, hypercholesterolemia, inflammatory diseases and infectious diseases.

15 Claims, 16 Drawing Sheets
Specification includes a Sequence Listing.

Before concentration

After concentration

ANTI-PCSK9 ANTIBODIES AND USES THEREOF

CROSS-REFERENCE TO RELATED APPLICATION

This application is a Section 371 of International Application No. PCT/CN2016/102209, filed Oct. 14, 2016, which was published in the English language on Apr. 20, 2017 under International Publication No. WO 2017/063593 A1, which claims priority under 35 U.S.C. § 119(b) to Chinese Application No. 201510673316.1, filed Oct. 16, 2105, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing File", creation date of Sep. 19, 2016 and having a size of about 76.7 kB. The sequence listing submitted via EFS-Web is part of the specification and is herein incorporated by reference in its entirety.

FIELD OF THE INVENTION

The invention relates to monoclonal anti-PCSK9 antibodies, nucleic acids and expression vectors encoding the antibodies, recombinant cells containing the vectors, and compositions comprising the antibodies. Methods of making the antibodies, and methods of using the antibodies to treat diseases including lipid disorders, metabolic diseases, hypercholesterolemia, inflammatory diseases and infectious diseases are also provided.

BACKGROUND OF THE INVENTION

In 2008, approximately 17 million people died from cardiovascular diseases, accounting for about one third of death worldwide. That number is expected to increase to 23.6 million by the year 2030 (Mozaffarian et al., 2015, Circulation. 131(4):e29-322). Various studies have shown a strong correlation between low density lipoprotein cholesterol (LDL-C) levels and the development of cardiovascular disease, due mainly to LDL-C playing a key in atherosclerosis (Rallidis and Lekakis, 2016, Hellenic J Cardiol. 57(2): 86-91). It is therefore thought that reducing plasma LDL-C levels could be an effective way to prevent cardiovascular diseases. Statins have served as the primary treatment for hypercholesterolemia for many years and have been largely effective. However, statin treatment fails to result in target LDL-C levels in a significant number of high risk patients, and new therapeutics for the lowering of LDL-C levels are therefore needed.

The majority of LDL-C is cleared by the LDL receptor (LDLR) on hepatocytes. In 2003, proprotein convertase subtilisin/kexin type 9a (PCSK9) was discovered as a key factor in the LDL-C clearance pathway. PCSK9 is produced mainly in hepatocytes and is a secreted serine protease that binds to LDLR and results in internalization and lysosomal degradation of LDLR. The resulting decrease in concentration of LDLR proteins at the surface of hepatocytes causes a reduction in LDL-C clearance from the plasma. Thus, the presence of PCSK9 can inhibit the hepatic metabolism of plasma LDL-C. In addition to LDLR and ApoB, PCSK9 is the third gene to be associated with autosomal dominant Familial Hyperlipidemia (Rallidis and Lekakis, 2016, Hellenic J Cardiol. 57(2):86-91).

Loss-of-function mutations in PCSK9 have been associated with a reduction of LDL-C levels and cardiovascular disease, while humans with high levels of PCSK9 have elevated levels of LDL-C and significantly enhanced risk of cardiovascular disease. Gain-of-function mutants of PCSK9 are causatively associated with familial hypercholesterolaemia (Gencer et al., 2015, Swiss Med Wkly. 145:w14094). In vitro experiments have shown that PCSK9 can reduce the expression level of LDLR on HepG2 cells. Similarly, an increase in PCSK9 levels in mice has reduced LDLR expression in the liver, while PCSK9 knockout mice have elevated LDLR expression. Taken together, the data suggests that PCSK9 is a promising therapeutic target in the management of lipid disorders.

Antibodies against PCSK9 are considered to be the greatest advance in cardiovascular disease prevention since statins, and it is thought that they can be used as therapeutics for treating, e.g., high cholesterol, hyperlipidemia, coronary heart disease, metabolic syndrome and acute coronary artery syndrome.

Phase I and II clinical trials of fully human PCSK9 monoclonal antibody (mAb) from, e.g., Amgen and Sanofi/Regeneron, have been completed, and gave ranges of promising results. For example, studies of Alirocumab (Sanofi/Regeneron) saw a reduction in LDL-C levels ranging from 39.2% to 67.9% (Gencer et al., 2015, Swiss Med Wkly. 145:w14094). Phase III clinical trials, with the objective of evaluating the effect of PCSK9 inhibition on the occurrence of cardiovascular events in patients with acute coronary syndrome are ongoing.

Despite the progress, there is a need in the art for more effective therapeutics comprising anti-PCSK9 antibodies that effectively inhibit the binding of PCSK9 to LDLR while causing minimal adverse side effects in humans.

BRIEF SUMMARY OF THE INVENTION

The invention satisfies this need by providing monoclonal antibodies that specifically bind PCSK9 with high affinity, induce LDL uptake by hepatocytes, and prevent LDLR degradation in vivo. In particular, the fully human anti-PCSK9 antibodies of the invention have a higher affinity to PCSK9 than Alirocumab (Regeneron).

In one general aspect, the invention relates to isolated monoclonal antibodies or antigen-binding fragments thereof that bind PCSK9.

According to a particular aspect, the invention relates to an isolated monoclonal antibody or antigen-binding fragment thereof comprising LCDR1, LCDR2, LCDR3, HCDR1, HCDR2 and HCDR3, having the polypeptide sequences of:
  (1) SEQ ID NOs: 38, 39, 40, 34, 35, and 36, respectively
  (2) SEQ ID NOs: 6, 7, 8, 2, 3, and 4, respectively;
  (3) SEQ ID NOs: 14, 15, 16, 10, 11, and 12, respectively;
  (4) SEQ ID NOs: 22, 23, 24, 18, 19, and 20, respectively;
  (5) SEQ ID NOs: 30, 31, 32, 26, 27, and 28, respectively; or
  (6) SEQ ID NOs: 46, 47, 48, 42, 43, and 44, respectively;
wherein the antibody or antigen-binding fragment thereof binds PCSK9 specifically, preferably binds specifically to human PCSK9.

According to another particular aspect, the invention relates to an isolated monoclonal antibody or antigen-binding fragment thereof comprising:

(1) an LCDR1 having the polypeptide sequence of SEQ ID NO: 38;
(2) an LCDR2 having the polypeptide sequence of SEQ ID NO: 39;
(3) an LCDR3 having the polypeptide sequence of SEQ ID NO: 40;
(4) an HCDR1 having the polypeptide sequence of SEQ ID NO: 34;
(5) an HCDR2 having the polypeptide sequence of SEQ ID NO: 35; and
(6) an HCDR3 having the polypeptide sequence of one of SEQ ID NOs: 36 and 73-90;

wherein the antibody or antigen-binding fragment thereof binds PCSK9, preferably binds specifically to human PCSK9.

According to another particular aspect, the invention relates to an isolated monoclonal antibody or antigen-binding fragment thereof, comprising a heavy chain variable region having a polypeptide sequence at least 85%, preferably at least 90%, more preferably at least 95% identical to one of SEQ ID NOs: 1, 9, 17, 25, 33 or 91-108, or 41, or a light chain variable region having a polypeptide sequence at least 85%, preferably at least 90%, more preferably at least 95% identical to one of SEQ ID NOs: 5, 13, 21, 29, 37 or 45.

According to one embodiment, the isolated monoclonal antibody or antigen-binding fragment thereof of the invention is human/rat chimeric.

According to another embodiment, the isolated monoclonal antibody or antigen-binding fragment thereof of the invention is human.

According to yet another embodiment, the isolated monoclonal antibody or antigen-binding fragment thereof of the invention further comprises a constant region, preferably a human heavy chain IgG constant region, and a human antibody light chain kappa constant region.

In another general aspect, the invention relates to an isolated nucleic acid encoding a monoclonal antibody or antigen-binding fragment thereof of the invention.

In another general aspect, the invention relates to a vector comprising an isolated nucleic acid encoding a monoclonal antibody or antigen-binding fragment thereof of the invention.

In another general aspect, the invention relates to a host cell comprising an isolated nucleic acid encoding a monoclonal antibody or antigen-binding fragment thereof of the invention.

In another general aspect, the invention relates to a pharmaceutical composition, comprising an isolated monoclonal antibody or antigen-binding fragment thereof of the invention and a pharmaceutically acceptable carrier.

In another general aspect, the invention relates to a method of blocking the binding of PCSK9 to LDLR, or a method of augmenting uptake of LDL, in a subject in need thereof, comprising administering to the subject a pharmaceutical composition of the invention.

In another general aspect, the invention relates to a method of treating a disease, disorder or condition, preferably a lipid disorder, a metabolic disease, an inflammatory disease or an infectious disease in a subject in need thereof, comprising administering to the subject a pharmaceutical composition of the invention.

In another general aspect, the invention relates to a method of producing a monoclonal antibody or antigen-binding fragment thereof of the invention, comprising culturing a cell comprising a nucleic acid encoding the monoclonal antibody or antigen-binding fragment under conditions to produce the monoclonal antibody or antigen-binding fragment thereof, and recovering the antibody or antigen-binding fragment thereof from the cell or cell culture.

In another general aspect, the invention relates to a method of producing a pharmaceutical composition comprising a monoclonal antibody or antigen-binding fragment thereof of the invention, comprising combining the monoclonal antibody or antigen-binding fragment thereof with a pharmaceutically acceptable carrier to obtain the pharmaceutical composition.

Other aspects, features and advantages of the invention will be apparent from the following disclosure, including the detailed description of the invention and its preferred embodiments and the appended claims.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIG. 23 A: the ratio of mLDLR/mβ-actin in mice administered with 30 mg/kg, 3 mg/kg, or 0.3 mg/kg of 139G1C8, control IgG or vehicle; and FIG. 23 B: the ratio of mLDLR/mβ-actin in mice administered with 30 mg/kg, 3 mg/kg, or 0.3 mg/kg of 96F8C6, control IgG or vehicle;

FIG. 27 A: inhibition of PCSK9$^{D374Y}$-induced LDL uptake in HepG2 cells by antibody clone AF-mab023_06, AF-mab023_12, or 96F8C6; and FIG. 27 B: inhibition of PCSK9$^{D374Y}$-induced LDL uptake in HepG2 cells by antibody clone AF-mab023_01, AF-mab023_11, AF-mab023_14, or AF-mab023_18.

DETAILED DESCRIPTION OF THE INVENTION

Figure 1:
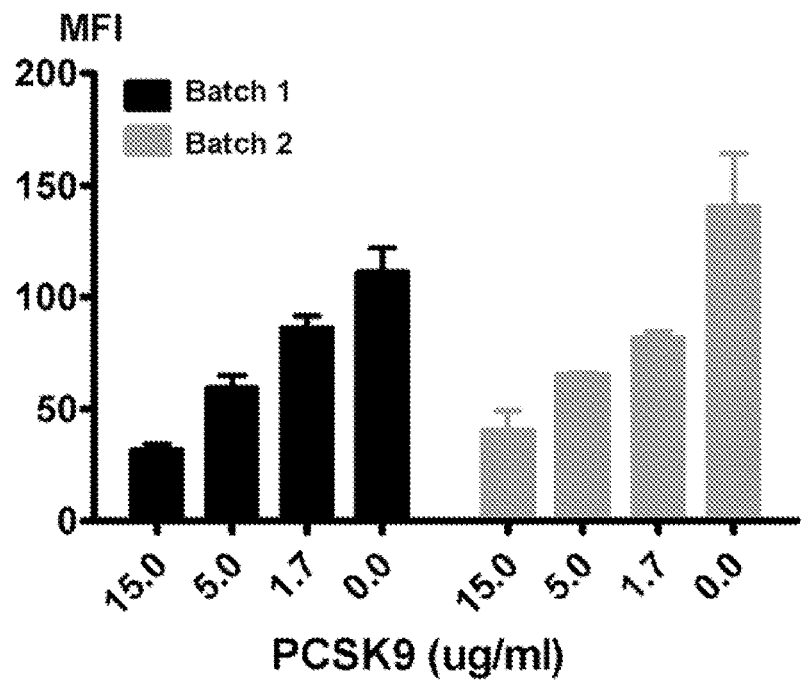
FIG. 1 shows effect of different batches of Immunogen A (hPCSK9-His) on LDL uptake inhibition in HepG2 cells.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

The invention generally relates to isolated anti-PCSK9 antibodies, nucleic acids and expression vectors encoding the antibodies, recombinant cells containing the vectors, and compositions comprising the antibodies. Methods of making the antibodies, and methods of using the antibodies to treat diseases including lipid disorders, metabolic diseases, hypercholesterolemia, inflammatory diseases and infectious diseases are also provided. The antibodies of the invention possess one or more desirable functional properties, including but not limited to high-affinity binding to PCSK9, high specificity to PCSK9, the ability to block the binding of PCSK9 to LDLR, and the ability to stimulate uptake of LDL and prevent the degradation of LDLR induced by PCSK9.

In a general aspect, the invention relates to isolated monoclonal antibodies or antigen-binding fragments thereof that bind PCSK9.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., CDR1, CDR2, and CDR3). The light chain variable region domains are alternatively referred to as LCDR1, LCDR2 and LCRD3, and the heavy chain variable region domains are alternatively referred to as HCDR1, HCRD2 and HCDR3.

As used herein, the term an "isolated antibody" refers to an antibody which is substantially free of other antibodies having different antigenic specificities (e.g., an isolated antibody that specifically binds to PCSK9 is substantially free of antibodies that do not bind to PCSK9). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab)2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the constant region of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "PCSK9" refers to the proprotein convertase subtilisin/kexin type 9 protein, a secretory protein that is a soluble member of the mammalian proprotein convertase family of secretory serine endoproteases. Secreted PCSK9 binds to LDLR on the surface of cells. Upon internalization of the bound proteins, PCSK9 prevents LDLR from endocytic recycling and results in lysosomal degradation of both proteins (Rallidis and Lekakis, 2016, Hellenic J Cardiol. 57(2):86-91). The term "human PCSK9" refers to a PCSK9 originated from a human. An exemplary amino acid sequence of a human PCSK9 is represented in GenBank Accession No. NP_777596.2.

As used herein, an antibody that "specifically binds to PCSK9" refers to an antibody that binds to a PCSK9, preferably a human PCSK9, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as a Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising LCDR1, LCDR2, LCDR3, HCDR1, HCDR2 and HCDR3, having the polypeptide sequences of:

(1) SEQ ID NOs: 38, 39, 40, 34, 35, and 36, respectively
(2) SEQ ID NOs: 6, 7, 8, 2, 3, and 4, respectively;
(3) SEQ ID NOs: 14, 15, 16, 10, 11, and 12, respectively;
(4) SEQ ID NOs: 22, 23, 24, 18, 19, and 20, respectively;
(5) SEQ ID NOs: 30, 31, 32, 26, 27, and 28, respectively; or
(6) SEQ ID NOs: 46, 47, 48, 42, 43, and 44, respectively;

wherein the antibody or antigen-binding fragment thereof binds PCSK9, preferably specifically binds to human PCSK9.

According to another particular aspect, the invention relates to an isolated monoclonal antibody or antigen-binding fragment thereof comprising:

(1) an LCDR1 having the polypeptide sequence of SEQ ID NO: 38;
(2) an LCDR2 having the polypeptide sequence of SEQ ID NO: 39;
(3) an LCDR3 having the polypeptide sequence of SEQ ID NO: 40;
(4) an HCDR1 having the polypeptide sequence of SEQ ID NO: 34;
(5) an HCDR2 having the polypeptide sequence of SEQ ID NO: 35; and
(6) an HCDR3 having the polypeptide sequence of one of SEQ ID NOs: 36 and 73-90;

wherein the antibody or antigen-binding fragment thereof binds PCSK9, preferably binds specifically to human-PCSK9.

According to another particular aspect, the invention relates to an isolated monoclonal antibody or antigen-binding fragment thereof of the invention, comprising a heavy chain variable region having a polypeptide sequence at least 85%, preferably 90%, more preferably 95% identical to one of SEQ ID NOs: 1, 9, 17, 25, 33 or 91-108, or 41, or a light chain variable region having a polypeptide sequence at least 85%, preferably 90%, more preferably 95% identical to one of SEQ ID NOs: 5, 13, 21, 29, 37 or 45. According to one preferred embodiment, the isolated monoclonal antibody or antigen-binding fragment thereof of the invention comprises a heavy chain variable region having the polypeptide sequence at least 85%, preferably 90%, more preferably 95% identical to SEQ ID NO: 1, 9, 17, 25, 33 or 41, and a light chain variable region having a polypeptide sequence at least 85%, preferably 90%, more preferably 95% identical to SEQ ID NO: 5, 13, 21, 29, 37 or 45, respectively. According to another preferred aspect, the isolated monoclonal antibody or antigen-binding fragment thereof of the invention comprises a heavy chain variable region having the polypeptide sequence at least 85% preferably 90%, more preferably 95% identical to one of SEQ ID NOs: 33 or 91-108, and a light chain variable region having a polypeptide sequence at least 85% preferably 90%, more preferably 95% identical to SEQ ID NO: 37.

According to another particular aspect, the invention relates to an isolated monoclonal antibody or antigen-binding fragment thereof of the invention, comprising:

a. a heavy chain variable region having the polypeptide sequence of SEQ ID NO: 1, and a light chain variable region having the polypeptide sequence of SEQ ID NO: 5;
b. a heavy chain variable region having the polypeptide sequence of SEQ ID NO: 9, and a light chain variable region having the polypeptide sequence of SEQ ID NO: 13;
c. a heavy chain variable region having the polypeptide sequence of SEQ ID NO: 17, and a light chain variable region having the polypeptide sequence of SEQ ID NO: 21;
d. a heavy chain variable region having the polypeptide sequence of SEQ ID NO: 25, and a light chain variable region having the polypeptide sequence of SEQ ID NO: 29;
e. a heavy chain variable region having the polypeptide sequence of one selected from the group consisting of SEQ ID NOs: 33 and 91-108, and a light chain variable region having the polypeptide sequence of SEQ ID NO: 37; or
f. a heavy chain variable region having the polypeptide sequence of SEQ ID NO: 41, and a light chain variable region having the polypeptide sequence of SEQ ID NO: 45.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 6, 7, 8, 2, 3, and 4, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 1, and a light chain variable region having a polypeptide sequence at least 85%, preferably 90%, more preferably 95% identical to SEQ ID NO: 5. Preferably, the isolated monoclonal antibody or antigen-binding fragment thereof comprises a heavy chain variable region having the polypeptide sequence of SEQ ID NO: 1; and a light chain variable region having the polypeptide sequence of SEQ ID NO: 5.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 14, 15, 16, 10, 11, and 12, respectively, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 9, and a light chain variable region having a polypeptide sequence at least 85%, preferably 90%, more preferably 95% identical to SEQ ID NO: 13. Preferably, the isolated monoclonal antibody or antigen-binding fragment thereof comprises a heavy chain variable region having the polypeptide sequence of SEQ ID NO: 9; and a light chain variable region having the polypeptide sequence of SEQ ID NO: 13.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 22, 23, 24, 18, 19, and 20, respectively, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 17, and a light chain variable region having a polypeptide sequence at least 85%, preferably 90%, more preferably 95% identical to SEQ ID NO: 21. Preferably, the isolated monoclonal antibody or antigen-binding fragment thereof comprises a heavy chain variable region having the polypeptide sequence of SEQ ID NO: 17; and a light chain variable region having the polypeptide sequence of SEQ ID NO: 21.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 30, 31, 32, 26, 27, and 28, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 25, and a light chain variable region having a polypeptide sequence at least 85%, preferably 90%, more preferably 95% identical to SEQ ID NO: 29. Preferably, the isolated monoclonal antibody or antigen-binding fragment thereof comprises a heavy chain variable region having the polypeptide sequence of SEQ ID NO: 25; and a light chain variable region having the polypeptide sequence of SEQ ID NO: 29.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 38, 39, 40, 34, 35, and 36, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 33, and a light chain variable region having a polypeptide sequence at least 85%, preferably 90%, more preferably 95% identical to SEQ ID NO: 37. Preferably, the isolated monoclonal antibody or antigen-binding fragment thereof comprises a heavy chain variable region having the polypeptide sequence of SEQ ID NO: 33; and a light chain variable region having the polypeptide sequence of SEQ ID NO:37.

In one embodiment, the invention relates to an isolated monoclonal antibody or antigen-binding fragment thereof, comprising an LCDR1 having the polypeptide sequence of SEQ ID NO: 38, an LCDR2 having the polypeptide sequence of SEQ ID NO: 39, an LCDR3 having the polypeptide sequence of SEQ ID NO: 40, an HCDR1 having the polypeptide sequence of SEQ ID NO: 34, an HCDR2 having the polypeptide sequence of SEQ ID NO: 35, and an HCDR3 having the polypeptide sequence of one selected from the group consisting of SEQ ID NOs: 36 and 73-90.

In another embodiment, the isolated monoclonal antibody or antigen-binding fragment thereof comprises a heavy chain variable region having a polypeptide sequence at least 85%, preferably 90%, more preferably 95% identical to one of SEQ ID NOs: 91-108, and a light chain variable region having a polypeptide sequence at least 85%, preferably 90%, more preferably 95% identical to SEQ ID NO: 37. Preferably, the isolated monoclonal antibody or antigen-binding fragment thereof comprises a heavy chain variable region having the polypeptide sequence of one of SEQ ID NOs: 91-108; and a light chain variable region having the polypeptide sequence of SEQ ID NO:37.

In one embodiment, the invention relates to an isolated monoclonal antibody or antigen-binding fragment thereof, comprising LCDR1, LCDR2, LCDR3, HCDR1, HCDR2 and HCDR3, having the polypeptide sequences of SEQ ID NOs: 46, 47, 48, 42, 43, and 44, respectively. In another embodiment, the isolated monoclonal antibody or antigen-binding fragment thereof comprises a heavy chain variable region having a polypeptide sequence at least 85%, preferably 90%, more preferably 95% identical to SEQ ID NO: 41, and a light chain variable region having a polypeptide sequence at least 85%, preferably 90%, more preferably 95% identical to SEQ ID NO: 45. Preferably, the isolated monoclonal antibody or antigen-binding fragment thereof comprises a heavy chain variable region having the polypeptide sequence of SEQ ID NO: 41; and a light chain variable region having the polypeptide sequence of SEQ ID NO:45.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human.

According to another particular aspect, the invention relates to an isolated monoclonal antibody or antigen-binding fragment thereof of the invention, comprising a constant region, preferably a human heavy chain IgG1 constant region (SEQ ID NO: 67), and a human antibody light chain, preferably a human light chain kappa constant region (SEQ ID NO: 69).

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

In another general aspect, the invention relates to a pharmaceutical composition, comprising an isolated monoclonal antibody or antigen-binding fragment thereof of the invention and a pharmaceutically acceptable carrier.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

In another general aspect, the invention relates to a method of blocking the binding of PCSK9 to LDLR, or of augmenting LDL uptake in liver in a subject in need thereof, comprising administering to the subject a pharmaceutical composition of the invention.

The functional activity of antibodies and antigen-binding fragments thereof that bind PCSK9 can be characterized by methods known in the art and as described herein. Methods for characterizing antibodies and antigen-binding fragments thereof that bind PCSK9 include, but are not limited to, affinity and specificity assays including Biacore, ELISA, and OctetRed analysis; receptor ligand binding assays to detect blocking of the binding of PCSK9 to LDLR; assays to detect inhibition of LDLR degradation induced by PCSK9 in HepG2 cells; assays to detect increases in LDL uptake by HepG2 cells; experiments to detect the inhibition of LDLR degradation induced by PCSK9 in liver, etc. According to particular embodiments, the methods for characterizing antibodies and antigen-binding fragments thereof that bind PCSK9 include those described in Examples 2-15 below.

In another general aspect, the invention relates to a method of treating lipid disorders, metabolic diseases, hypercholesterolemia, inflammatory diseases and infectious diseases in a subject in need thereof, comprising administering to the subject a pharmaceutical composition of the invention.

As used herein, the term "subject" refers to an animal, and preferably a mammal. According to particular embodiments, the subject is a mammal including a non-primate (e.g., a camel, donkey, zebra, cow, pig, horse, goat, sheep, cat, dog, rat, rabbit, guinea pig or mouse) or a primate (e.g., a monkey, chimpanzee, or human). In particular embodiments, the subject is a human.

According to embodiments of the invention, the pharmaceutical composition comprises a therapeutically effective amount of the anti-PCSK9 antibody or antigen-binding fragment thereof. As used herein, the term "therapeutically effective amount" refers to an amount of an active ingredient or component that elicits the desired biological or medicinal response in a subject A therapeutically effective amount can be determined empirically and in a routine manner, in relation to the stated purpose.

As used herein with reference to anti-PCSK9 antibodies or antigen-binding fragments thereof, a therapeutically effective amount means an amount of the anti-PCSK9 antibody or antigen-binding fragment thereof that stimulates LDL uptake in a subject in need thereof. Also as used herein with reference to anti-PCSK9 antibodies or antigen-binding fragments thereof, a therapeutically effective amount means an amount of the anti-PCSK9 antibody or antigen-binding fragment thereof that results in treatment of a disease, disorder, or condition; prevents or slows the progression of the disease, disorder, or condition; or reduces or completely alleviates symptoms associated with the metabolic disease, disorder, or condition.

According to particular embodiments, the disease, disorder or condition to be treated is a lipid disorder, hyperlipidemia, dyslipidemia, or a metabolic disease. According to more particular embodiments, the disease, disorder or condition to be treated is a lipid disorder, including but not limited to, primary hyperlipidemia, mixed dyslipidemia, homozygous familial hypercholesterolemia. According to other particular embodiments, the disease, disorder or condition to be treated is an inflammatory disease, such as sepsis, or an infectious diseases.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a lipid disease, disorder or condition or a metabolic disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as lipid disorder, hyperlipidemia, dyslipidemia, mixed dyslipidemia, homozygous familial hypercholesterolemia, a metabolic disease, an inflammatory disease such as sepsis, or an infectious disease. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition used in the treatment of a lipid disease, disorder or condition or a metabolic disease, disorder or condition can be used in combination with another treatment including, but not limited to, statins or other lipid lowering drugs.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

EMBODIMENTS

The invention provides also the following non-limiting embodiments.

Embodiment 1 is an isolated monoclonal antibody or antigen-binding fragment thereof comprising LCDR1, LCDR2, LCDR3, HCDR1, HCDR2 and HCDR3, having the polypeptide sequences of:
(1) SEQ ID NOs: 6, 7, 8, 2, 3, and 4, respectively;
(2) SEQ ID NOs: 14, 15, 16, 10, 11, and 12, respectively;
(3) SEQ ID NOs: 22, 23, 24, 18, 19, and 20, respectively;
(4) SEQ ID NOs: 30, 31, 32, 26, 27, and 28, respectively;
(5) SEQ ID NOs: 38, 39, 40, 34, 35, and 36, respectively; or
(6) SEQ ID NOs: 46, 47, 48, 42, 43, and 44, respectively;
wherein the antibody or antigen-binding fragment thereof binds PCSK9, preferably binds specifically to human PCSK9.

Embodiment 2 is an isolated monoclonal antibody or antigen-binding fragment thereof comprising:

(1) an LCDR1 having the polypeptide sequence of SEQ ID NO: 38;
(2) an LCDR2 having the polypeptide sequence of SEQ ID NO: 39;
(3) an LCDR3 having the polypeptide sequence of SEQ ID NO: 40;
(4) an HCDR1 having the polypeptide sequence of SEQ ID NO: 34;
(5) an HCDR2 having the polypeptide sequence of SEQ ID NO: 35;
(6) an HCDR3 having the polypeptide sequence of one of SEQ ID NOs: 36 and 73-90;
wherein the antibody or antigen-binding fragment thereof binds PCSK9, preferably binds specifically to human PCSK9.

Embodiment 3 is the isolated monoclonal antibody or antigen-binding fragment of Embodiment 1 or 2, comprising a heavy chain variable region having a polypeptide sequence at least 95% identical to one of SEQ ID NOs: 1, 9, 17, 25, 33 or 91-108, or 41, or a light chain variable region having a polypeptide sequence at least 95% identical to one of SEQ ID NOs: 5, 13, 21, 29, 37 or 45.

Embodiment 4 is the isolated monoclonal antibody or antigen-binding fragment of Embodiment 3, comprising a heavy chain variable region having a polypeptide sequence at least 95% identical to SEQ ID NO: 1, 9, 17, 25, 33 or 41, and a light chain variable region having a polypeptide sequence at least 95% identical to SEQ ID NO: 5, 13, 21, 29, 37 or 45 respectively.

Embodiment 5 is the isolated monoclonal antibody or antigen-binding fragment of Embodiment 3, comprising a heavy chain variable region having a polypeptide sequence at least 95% identical to one of SEQ ID NOs: 91-108, and a light chain variable region having a polypeptide sequence at least 95% identical to SEQ ID NO: 37.

Embodiment 6 is the isolated monoclonal antibody or antigen-binding fragment of Embodiment 4 or 5, comprising:
(a) a heavy chain variable region having the polypeptide sequence of SEQ ID NO: 1, and a light chain variable region having the polypeptide sequence of SEQ ID NO: 5;
(b) a heavy chain variable region having the polypeptide sequence of SEQ ID NO: 9, and a light chain variable region having the polypeptide sequence of SEQ ID NO: 13;
(c) a heavy chain variable region having the polypeptide sequence of SEQ ID NO: 17, and a light chain variable region having the polypeptide sequence of SEQ ID NO: 21;
(d) a heavy chain variable region having the polypeptide sequence of SEQ ID NO: 25, and a light chain variable region having the polypeptide sequence of SEQ ID NO: 29;
(e) a heavy chain variable region having the polypeptide sequence of one of SEQ ID NOs: 33 or 91-108, and a light chain variable region having the polypeptide sequence of SEQ ID NO: 37; or
(f) a heavy chain variable region having the polypeptide sequence of SEQ ID NO: 41, and a light chain variable region having the polypeptide sequence of SEQ ID NO: 45.

Embodiment 7 is the isolated monoclonal antibody or antigen-binding fragment of any of Embodiments 1 to 6, wherein the antibody or antigen-binding fragment thereof is chimeric.

Embodiment 8 is isolated monoclonal antibody or antigen-binding fragment of any of Embodiments 1 to 7, wherein the antibody or antigen-binding fragment thereof is human.

Embodiment 9 is the isolated antibody or antigen-binding fragment of Embodiment 8, comprising a human heavy chain IgG1 constant region and a human antibody light chain kappa constant region.

Embodiment 10 is the isolated antibody or antigen-binding fragment of any of Embodiments 1 to 9, wherein the antibody or antigen-binding fragment binds to a human PCSK9 with a $K_D$ of $5\times10^{-9}$ M or less, preferably a $K_D$ of $1\times10^{-9}$ M or less, wherein the $K_D$ is measured by surface plasmon resonance analysis, such as by using a Biacore system, or by a bio-layer interferometry technology, such as by using a Octet RED96 system.

Embodiment 11 is an isolated nucleic acid encoding the monoclonal antibody or antigen-binding fragment of any of Embodiments 1 to 10.

Embodiment 12 is a vector comprising the isolated nucleic acid of Embodiment 11.

Embodiment 13 is a host cell comprising the nucleic acid of Embodiment 12.

Embodiment 14 is a pharmaceutical composition, comprising the isolated monoclonal antibody or antigen-binding fragment of any of Embodiments 1 to 10 and a pharmaceutically acceptable carrier.

Embodiment 15 is a method of blocking binding of PCSK9 to LDLR, or augmenting uptake of LDL in a subject in need thereof, comprising administering to the subject the pharmaceutical composition of Embodiment 14.

Embodiment 16 is a method of treating a lipid disease, disorder or condition, a metabolic disease, disorder or condition, an inflammatory disease, disorder or condition, or an infectious disease, disorder or condition in a subject in need thereof, comprising administering to the subject the pharmaceutical composition of Embodiment 14.

Embodiment 17 is the method of Embodiment 16, further comprising administering to the subject an additional agent for treating the lipid disorder, metabolic disease, inflammatory disease, or infectious disease in the subject in need thereof.

Embodiment 18 is a method of treating a lipid disorder, metabolic disease, inflammatory disease, or infectious disease in a subject in need thereof, comprising administering to the subject the pharmaceutical composition of Embodiment 14.

Embodiment 19 is the method of Embodiment 18, wherein the lipid disorder or metabolic disease is hyperlipidemia, primary hyperlipidemia, dyslipidemia, mixed dyslipidemia, or homozygous familial hypercholesterolemia, or wherein the inflammatory disease is sepsis.

Embodiment 20 is the method of any of Embodiments 18-19, further comprising administering to the subject an additional agent for treating the lipid disorder, metabolic disease, inflammatory disease, or infectious disease in the subject in need thereof.

Embodiment 21 is a method of producing the monoclonal antibody or antigen-binding fragment of any of Embodiments 1 to 10, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or cell culture.

Embodiment 22 is a method of producing a pharmaceutical composition comprising the monoclonal antibody or antigen-binding fragment of any of Embodiments 1 to 10, comprising combining the monoclonal antibody or antigen-binding fragment with a pharmaceutically acceptable carrier to obtain the pharmaceutical composition.

Embodiment 23 is an isolated monoclonal antibody or antigen-binding fragment of any of Embodiments 1 to 10 for use in treating a lipid disorder, metabolic disease, inflammatory disease, or infectious disease, such as hyperlipidemia, primary hyperlipidemia, dyslipidemia, mixed dyslipidemia, homozygous familial hypercholesterolemia or sepsis, in a subject in need thereof.

Embodiment 24 is a pharmaceutical composition of Embodiment 14 for use in treating a lipid disorder, metabolic disease, inflammatory disease, or infectious disease, such as hyperlipidemia, primary hyperlipidemia, dyslipidemia, mixed dyslipidemia, homozygous familial hypercholesterolemia, or sepsis in a subject in need thereof.

Embodiment 25 is an use of an isolated monoclonal antibody or antigen-binding fragment of any of Embodiments 1 to 10 for the manufacture of a medicament for treating a lipid disorder, metabolic disease, inflammatory disease, or infectious disease, such as hyperlipidemia, primary hyperlipidemia, dyslipidemia, mixed dyslipidemia, homozygous familial hypercholesterolemia, or sepsis, in a subject in need thereof.

Embodiment 26 is an use of a pharmaceutical composition of Embodiment 14 for the manufacture of a medicament for treating a lipid disorder, metabolic disease, inflammatory disease, or infectious disease, such as hyperlipidemia, primary hyperlipidemia, dyslipidemia, mixed dyslipidemia, homozygous familial hypercholesterolemia, or sepsis, in a subject in need thereof.

EXAMPLES

The following examples of the invention are to further illustrate the nature of the invention. It should be understood that the following examples do not limit the invention and that the scope of the invention is to be determined by the appended claims.

Example 1—Generation of Anti-PCSK9 Antibodies

Human PCSK9 protein was used as an immunogen to generate anti-PCSK9 antibodies. The use of human immunoglobulin transgenic mouse technology for the development and preparation of fully human antibodies was first described by Abgenix (xeno mouse and Medarex (HuMab "mouse"); Lonberg et al., 1994, Nature 368: 856-859; Lonberg and Huszar, 1995, Internal Rev. Immunol. 13:65-93; Harding and Lonberg, 1995, Ann. N.Y. Acad. Sci. 764:536-546).

Antibodies with high affinity ($K_D$<1*10-9M) to PCSK9 were obtained by carrying out pilot antibody production, purification and validation. The antibodies, which are specific for PCSK9, are able to block the binding of PCSK9 to LDLR. The amino acid sequences of the heavy and light chain variable regions of the generated anti-PCSK9 antibodies were determined using standard molecular biology methods and are summarized in Table 1.

TABLE 1

SEQ ID NOs of the amino acid sequences of the heavy chain variable regions, HCDRs, light chain variable regions and LCDRs of chimeric anti-PCSK9 antibodies of the invention

| | SEQ ID NOs | | | | | | | |
|---|---|---|---|---|---|---|---|---|
| | Heavy Chain | | | | Light Chain | | | |
| Clone ID | variable region | CDR1 | CDR2 | CDR3 | variable region | CDR1 | CDR2 | CDR3 |
| 74C10A8 | 1 | 2 | 3 | 4 | 5 | 6 | 7 | 8 |
| 76A1B11 | 9 | 10 | 11 | 12 | 13 | 14 | 15 | 16 |
| 139G1C5 | 17 | 18 | 19 | 20 | 21 | 22 | 23 | 24 |
| 152G2F7 | 25 | 26 | 27 | 28 | 29 | 30 | 31 | 32 |
| 96F8C6 | 33 | 34 | 35 | 36 | 37 | 38 | 39 | 40 |
| 103C11E8 | 41 | 42 | 43 | 44 | 45 | 46 | 47 | 48 |

The heavy chain and light chain variable regions of the anti-PCSK9 antibodies listed in Table 1 are encoded by the nucleic acid sequences summarized in Table 2.

TABLE 2

SEQ ID NOs of the nucleic acid sequences of the heavy chain and light chain variable regions of chimeric anti-PCSK9 antibodies of the invention

| | SEQ ID NOs (nucleotides of the sequence corresponding to CDRs) | |
|---|---|---|
| Clone ID | Heavy Chain variable region | Light Chain variable region |
| 74C10A8 | 49 | 50 |
| | (CDR1: nt 76-105) | (CDR1: nt 70-102) |
| | (CDR2: nt 148-195) | (CDR2: nt 148-168) |
| | (CDR3: nt 289-351) | (CDR3: nt 263-291) |
| 76A1B11 | 51 | 52 |
| | (CDR1: nt 76-105) | (CDR1: nt 70-102) |
| | (CDR2: nt 148-198) | (CDR2: nt 148-168) |
| | (CDR3 :nt 295-342) | (CDR3: nt 265-291) |
| 139G1C5 | 53 | 54 |
| | (CDR1: nt 76-108) | (CDR1: nt 70-102) |
| | (CDR2: nt 151-198) | (CDR2: nt 148-168) |
| | (CDR3: nt 295-321) | (CDR3: nt 265-291) |
| 152G2F7 | 55 | 56 |
| | (CDR1: nt 76-105) | (CDR1: nt 70-102) |
| | (CDR2: nt 148-195) | (CDR2: nt 148-168) |
| | (CDR3: nt 295-354) | (CDR3: nt 265-291) |
| 96F8C6 | 57 | 58 |
| | (CDR1: nt 76-105) | (CDR1: nt 70-102) |
| | (CDR2: nt 148-198) | (CDR2: nt 148-168) |
| | (CDR3: nt 295-357) | (CDR3: nt 265-291) |
| 103C11E8 | 59 | 60 |
| | (CDR1: nt 76-108) | (CDR1: nt 70-102) |
| | (CDR2: nt 151-198) | (CDR2: nt 148-168) |
| | (CDR3: nt 295-330) | (CDR3: nt 265-291) |

Fully human versions of the anti-PCSK9 antibodies were generated. The fully human anti-PCSK9 antibodies bound to the human PCSK9 with high affinity ($K_D < 1*10^{-9}$M), and blocked the binding of PCSK9 to LDLR. The biological activities of the anti-PCSK9 antibodies were evaluated by receptor ligand blocking assay and LDL uptake assays, in which they blocked PCSK9 binding to LDLR, enhanced LDL uptake by HepG2 cells, and prevented PCSK9-induced LDLR degradation in vivo. The anti-PCSK9 antibodies can be used for the treatment of lipid disorders, metabolic diseases, hypercholesterolemia, inflammatory diseases or infectious diseases.

Example 2—Preparation of Anti-PCSK9 Antibodies (Step 1) Preparation of Immunogen A, His-Tagged PCSK9 (PCSK9-his)

The coding sequence of human PCSK9 (hPCSK9; SEQ ID NO: 61), corresponding to the full-length protein sequence of SEQ ID NO: 62 (UniProtKB ID Q8NBP7), was cloned along with a His tag into pCpC vector (Invitrogen, # V044-50) using standard molecular biology cloning techniques (Sambrook and Russell, 1989, Molecular cloning: a laboratory manual, New York: Cold Spring Haibor Laboratory Press, 2nd ed.). HEK293 cells (Invitrogen) were transiently transfected using polyethylenimine (PEI, Polysciences) with the plasmid and expanded in FreeStyle 293 expression medium (Invitrogen) at 37° C. After 4 days of expansion, the culture medium was collected and centrifuged to remove cell components. The culture supernatant contained the recombinant His-tagged PCSK9. Imidazole was added to a final concentration of 10 mM to the culture supernatant, which contained the recombinant His-tagged PCSK9. The sample was passed through a 0.22 micron sterile filter and subjected to Ni-NTA affinity chromatography. After equilibrating the sample with Buffer A [1×PBS, pH 7.2 containing 20 mM Imidazole) and Buffer B [(Buffer A, 0.1% (v/v) Triton X100, 0.1% (v/v) Triton X114], His-tagged PCSK9 protein (PCSK9-His) was eluted from the Ni-NTA affinity chromatography column with Buffer C [1×PBS (pH7.2), 250 mM imidizole]. The eluate was further purified using a Superdex 200 column (GE, Healthcare) to obtain highly pure His-tagged recombinant human PCSK9 protein. The sample was dialyzed with 1×PBS (pH7.2) at 4° C. overnight. After dialysis, the purified PCSK9-His was passed through a 0.22 micron sterile filter, aliquoted and stored at −80° C.

To characterize the PCSK9-His immunogen, the sample's protein concentration and purity were determined, and the immunogen's molecular weight and biological activity were determined.

The biological activity of the His-tagged hPCSK9 immunogen was assessed in a series of in vitro characterizations, and it was found that the immunogen displayed the bioactivity of PCSK9, and it inhibited LDL uptake by HepG2 cells in a dose-dependent manner. The two batches of His-tagged hPCSK9 immunogen that were produced demonstrated comparable bioactivity in the inhibition of HepG2 LDL uptake (see FIG. 1). These two batches of biologically active His-tagged hPCSK9 immunogen were used for mouse immunizations.

TABLE 3

Recombinant human PCSK9 inhibits LDL uptake by HepG2 cells

| Mean fluorescence intensity | hPCSK9 protein (ug/mL) | | | |
|---|---|---|---|---|
| Batch | 15.0 | 5.0 | 1.7 | 0.0 |
| hPCSK9-batch 1 | 31.7 | 59.4 | 86.0 | 111.3 |
| hPCSK9- batch 2 | 40.4 | 65.1 | 81.8 | 140.4 |

(Step 2) Preparation of Immunogen B, hPCS9 Expressing Construct

The coding sequence of human PCSK9 (hPCSK9; SEQ ID NO: 61) was subcloned into pcDNA3.1 vector (Invitrogen), and the resulting plasmid was coated onto a 1.0 um colloidal gold bullet (Bio-RAD) for subsequent immunization using a Helios gene gun (Bio-rad No. 165-2431), following the instructions of the Helios gene gun data sheet (Step 3) Hybridoma Cell Fusion and Antibody Screening Human Ig Fc does not interact with the mouse Fc receptor, so immune responses triggered in mice by hFc-containing immunogens are weak, resulting in low efficiency generation of monoclonal antibodies. Harbour H2L2 transgenic mice were generated by introducing the gene encoding the human immunoglobulin (Ig) variable region and the gene encoding the rat Ig constant region into the mouse genome, such that the mice contained a chimeric Ig comprising hV-rC, while expression of the mouse Ig was disabled (WO 2010/070263 A1). Harbour H2L2 transgenic mice are able to produce comparable immune responses and antibody titers to wild type mice (e.g., Balb/c).

(part 3A) 6-8 week old Harbour H2L2 transgenic mice (Beijing Weitong Lihua) were immunized with Immunogen A, and the mice were kept under Specific Pathogen Free (SPF) conditions. In the first immunization, 50 ug of Immunogen A was injected into the abdominal cavity of each mouse along with 0.25 mL Complete Freund's Adjuvant (CFA). To enhance the immune response, 50 ug of Immunogen A was injected into the abdominal cavity of each mouse along with 0.25 Incomplete Freund's Adjuvant (IFA) two weeks after the first immunization, and subsequent boosts were administered 3 weeks apart. Blood samples were collected one week after immunization. The antibody titer and specificity in serum were determined by ELISA, and the results are shown in Table 4. The blank control was 1% (w/w) BSA. The OD450 nm values shown in Table 4 are the serum titer values from 7 days after the third boost, as determined by ELISA. The serum titer after the third boost usually reached at least 1:10,000.

TABLE 4

Serum titers of Harbour H2L2 transgenic mice immunized with hPCSK9-His protein, as determined by ELISA

| | $OD_{450\ nm}$ Serum dilution factors | | | | | | |
|---|---|---|---|---|---|---|---|
| Animal No. | 1:100 | $1:10^3$ | $1:10^4$ | $1:10^5$ | $1:10^6$ | $1:10^7$ | Blank |
| 1556 (TB3) | 3.32 | 3.11 | 0.84 | 0.17 | 0.08 | 0.12 | 0.12 |
| 1557 (TB3) | 3.31 | 3.05 | 0.85 | 0.14 | 0.06 | 0.06 | 0.06 |
| 1558 (TB3) | 3.31 | 3.11 | 1.04 | 0.17 | 0.06 | 0.07 | 0.08 |
| 1559 (TB3) | 3.35 | 3.23 | 1.16 | 0.18 | 0.07 | 0.06 | 0.06 |
| 1560 (TB3) | 3.00 | 0.84 | 0.15 | 0.08 | 0.06 | 0.05 | 0.07 |

(part 3B) 6-8 week old Harbour H2L2 transgenic mice (Beijing Weitong Lihua) were immunized with Immunogen A, and the mice were kept under SPF conditions. In the first immunization, 50 ug of Immunogen A was injected into bottom of the tail (BOT) of each mouse along with 0.20 ml of Gerbu adjuvant (Invitrogen). The first the boost was administered two weeks after the first immunization, and subsequent boosts were administered three weeks apart. Blood samples were collected one week after immunization. The antibody titer and specificity in serum were determined by ELISA, and the results are shown in Table 5. The blank control was 1% (w/w) BSA. The OD450 nm values shown in Table 5 are the serum titer values from 7 days after the third boost, as determined by ELISA. The serum titer after the third boost usually reached at least 1:10,000.

TABLE 5

Serum titers of Harbour H2L2 transgenic mice immunized with hPCSK9-His protein, as determined by ELISA

| | $OD_{450\ nm}$ Serum dilution factors | | | | | | |
|---|---|---|---|---|---|---|---|
| Animal No. | 1:100 | $1:10^3$ | $1:10^4$ | $1:10^5$ | $1:10^6$ | $1:10^7$ | Blank |
| 1576 (TB3) | 3.26 | 1.74 | 0.28 | 0.08 | 0.06 | 0.07 | 0.07 |
| 1577 (TB3) | 3.16 | 1.20 | 0.23 | 0.07 | 0.06 | 0.07 | 0.07 |
| 1578 (TB3) | 2.83 | 0.58 | 0.12 | 0.07 | 0.06 | 0.06 | 0.07 |
| 1579 (TB3) | 3.26 | 2.69 | 0.47 | 0.11 | 0.08 | 0.07 | 0.06 |
| 1580 (TB3) | 3.16 | 1.44 | 0.23 | 0.09 | 0.06 | 0.07 | 0.07 |

(part 3C) 6-8 week old Harbour H2L2 transgenic mice (Beijing Weitong Lihua) were immunized with Immunogen A, and the mice were kept under SPF conditions. In the first immunization, 50 ug of Immunogen A was injected into the abdominal cavity of each mouse along with 0.25 mL Complete Freund's Adjuvant (CFA). To enhance the immune response, 50 ug of Immunogen A was injected into the abdominal cavity of each mouse along with 0.25 Incomplete Freund's Adjuvant (IFA) two weeks after the first immunization, and subsequent boosts were administered 3 weeks apart Blood samples were collected one week after immunization. The antibody titer and specificity in serum were determined by ELISA and FACS analysis, and the results are shown in Table 6. Table 6 shows that serum from mice immunized with PCSK9 exhibited different levels of binding to Immunogen A. The highest serum dilution was about one million. The blank control was 1% (w/w) BSA. The OD450 nm values shown in Table 6 are the serum titer values from 7 days after the third boost, as determined by ELISA.

TABLE 6

Serum titers of Harbour H2L2 transgenic mice immunized with hPCSK9-His protein, as determined by ELISA

| | $OD_{450\ nm}$ Serum dilution factors | | | | | | |
|---|---|---|---|---|---|---|---|
| Animal No. | 1:100 | $1:10^3$ | $1:10^4$ | $1:10^5$ | $1:10^6$ | $1:10^7$ | Blank |
| 1581 (TB3) | 2.52 | 0.90 | 0.37 | 0.28 | 0.25 | 0.26 | 0.22 |
| 1582 (TB3) | 2.79 | 2.13 | 0.66 | 0.23 | 0.17 | 0.224 | 0.23 |
| 1583 (TB3) | 1.76 | 0.44 | 0.35 | 0.23 | 0.27 | 0.30 | 0.30 |
| 1584 (TB3) | 2.19 | 0.83 | 0.37 | 0.19 | 0.16 | 0.18 | 0.22 |
| 1585 (TB3) | 2.19 | 0.68 | 0.33 | 0.24 | 0.18 | 0.27 | 0.24 |

Prior to the completion of steps 3A-C above, mice with specific immune response against hPCSK9 were selected for fusion and were given a final boost by intraperitoneal injection of 100 ug hPCSK9-His. Three days later, the mice were sacrificed, and their splenocytes were collected. NH4OH was added to the splenocyte samples to a final concentration of 1% (w/w) to lyse red blood cells in the sample. The samples were centrifuged at 1000 rpm and washed three times with DMEM culture media. The viability of the splenocytes was determined, and viable splenocytes were then fused with mouse myeloma cells SP2/0 (ATCC) at a ratio of 5:1 by the high efficiency electric fusion method (see Methods in Enzymology, Vol. 220).

Fused cells were re-suspended in DMEM media containing 20% FBS and 1× hypoxanthine-aminopterin-thymidine (HAT) medium (w/w), and the concentration was adjusted to $10^5$ cells/200 uL. 200 uL of fused cells were added to each well of 96-well plate, which was incubated at 37° C., 5% $CO_2$. 14 days after cell fusion, hybridoma supernatants were collected and screened by ELISA. Clones with an OD450 nm greater than 0.5 by ELISA were expanded in a 24-well plate containing DMEM with 10% (w/w) heat-inactivated FBS at 37° C., 5% (v/v) $CO_2$. Supernatants were collected after 3 days of culturing. The antibody isotypes were determined, and their ability to bind to recombinant $PCSK9^{D374Y}$ protein (gain-of-function mutant; prepared using the method of Example 1) was determined by ELISA (see Example 3). A receptor ligand binding assay was performed to determine the blocking activity of the hybridoma supernatant (see Example 4), an assay to measure degradation of LDLR was performed (see Example 5), and a blocking assay to measure PCSK9-mediated cellular LDL uptake was carried out (see Example 6).

Based on the 24-well plate screening results, clones that bound to PCSK9, blocked the receptor-ligand interaction between PCSK9 and LDLR, and inhibited PCSK9-mediated reduction in LDL uptake were selected and subcloned. Subcloning was carried out by limited dilution in a 96-well plate with DMEM media containing 10% (v/v) FBS at 37° C. and 5% (v/v) $CO_2$. After 10 days of culturing, the supernatants were collected and preliminarily screened by assessing their ability to bind to recombinant human PCSK9, $PCSK9^{D374Y}$, cyno monkey PCSK9 (SEQ ID NO: 63, prepared using the method of Example 1) and mouse PCSK9 (UniProtKB ID Q80W65; SEQ ID NO: 65, prepared using the method of Example 1), as determined by ELISA, or their ability to block binding of PCSK9 or $PCSK9^{D374Y}$ to LDLR.

Clones that met the selection criteria were expanded in DMEM media containing 10% (w/w) FBS at 37° C., 5% (v/v) $CO_2$ and frozen in liquid nitrogen so that the hybridoma cells could be used for subsequent antibody production and purification.

(Step 4) Production and Purification of Lead Candidate Antibodies

The antibody concentrations from the hybridoma cells were low, about 1-10 ug/mL, and there was a large variation in antibody concentrations. In addition, the FBS and the components of the culture medium can interfere with the analysis. Therefore, it was necessary to perform small scale antibody production and purification (1-5 mg).

Hybridoma cells from Example 2 were cultured in T-75 culture flasks using Hybridoma serum free medium (Invitrogen), and passaged for 3 generations. Cells were transferred to 2 L culture flasks when the hybridoma cells were in good condition. 500 mL of production media was added to each culture flask, and the cell density was adjusted to $10^5$ cells/mL. The culture flasks were placed onto a rotary incubator at 37° C. with a rotating speed of 3 cycles per minute. Hybridoma cells were cultured for 14 days, after which the supernatant was collected and the cells were removed. The supernatants were then filtered through 0.45 micron filtration. The culture supernatants were then ready for purification or storage at −30° C.

Monoclonal antibodies were purified by passing the hybridoma culture supernatants through 2 mL Protein G columns (GE Healthcare). Protein G columns were first equilibrated with PBS buffer (pH7.2), and the hybridoma culture supernatants were then applied to the equilibrated Protein G columns with a constant flow rate of 3 mL/minute. The columns were then washed with 4 volumes of PBS buffer. The anti-PCSK9 antibodies were then eluted with elution buffer (0.1M acetate buffer, pH2.5), and the UV absorbance of the eluates were monitored using a UV detector (A280 UV absorption peak). 10% of 1.0M Tris-HCL buffer was added to the eluates to neutralize the pH, and the samples were sterile-filtered by passing them through 0.22 micron filters. Sterile-filtered purified anti-PCSK9 antibodies were obtained.

The concentrations of purified anti-PCSK9 antibodies were determined by UV absorbance (A280/1.4), and the purity and endotoxin level (Lonza kit) were measured. The results of the analyses are shown in Table 7. The purified anti-PCSK9 antibodies had endotoxin concentrations less than 1.0 EU/mg.

TABLE 7

Quality Control analysis of Purified Chimeric PCSK9 mAbs from Hybridoma

| Clone ID | Purity | Protein Concentration (ug/mL) | Endotoxin(EU/μg) |
|---|---|---|---|
| 74C10A8 | >90% | 1.35 | <0.12 |
| 76A1B11 | >90% | 0.58 | <0.12 |
| 139G1C5 | >90% | 0.30 | <0.12 |
| 152G2F7 | >90% | 0.54 | <0.12 |
| 96F8C6 | >90% | 0.98 | <0.12 |
| 103C11E8 | ND | 0.43 | <0.12 |

Example 3—Characterization of Lead Candidate Antibodies (Part A) Detection of the Binding of Anti-PCSK9 Antibodies to Recombinant PCSK9 and $PCSK9^{D374Y}$ Protein by ELISA The binding of purified anti-PCSK9 antibodies from Example 2 to recombinant human PCSK9 protein (Immunogen A), $PCSK9^{D374Y}$ and cyno PCSK9 protein was analyzed by ELISA.

Figure 2:
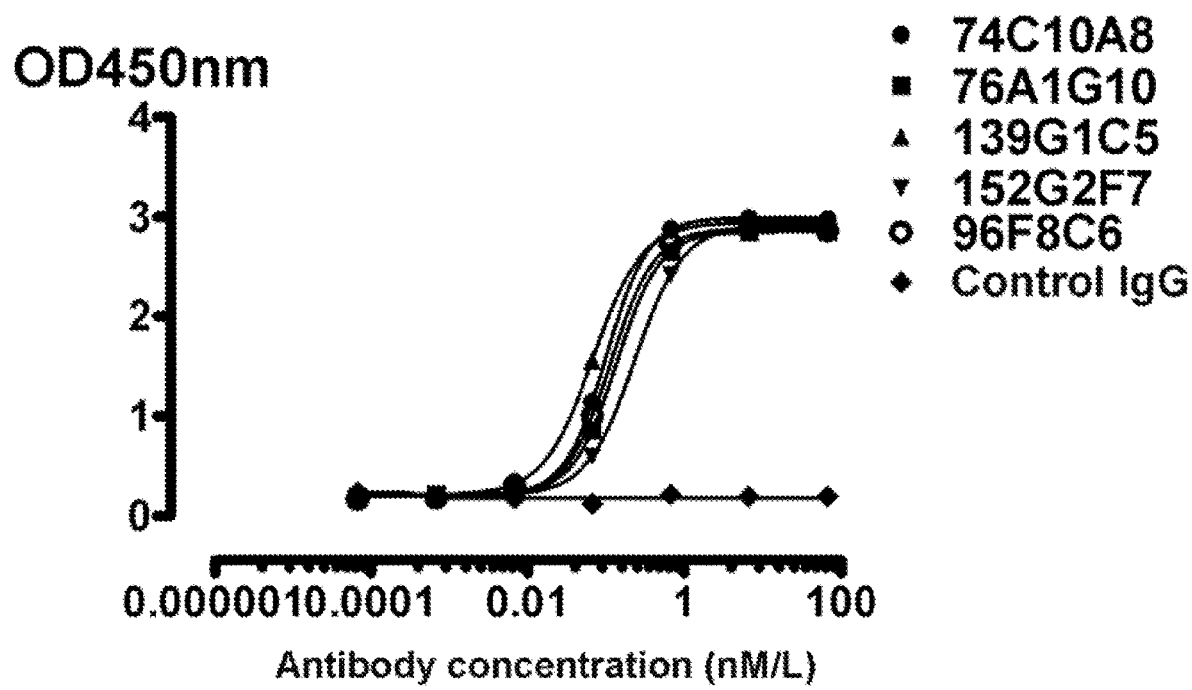
FIG. 2 shows the binding activity of chimeric anti-PCSK9 antibodies according to embodiments of the invention to Immunogen A (hPCSK9-His), as measured by ELISA.
Figure 3:
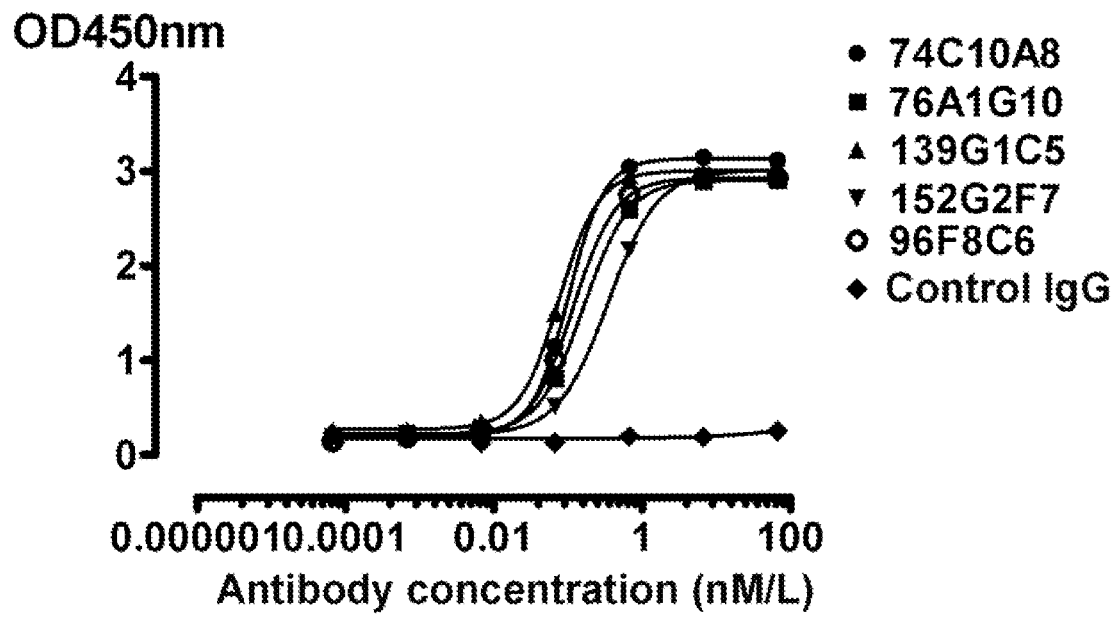
FIG. 3 shows the binding activity of chimeric anti-PCSK9 antibodies according to embodiments of the invention to recombinant human $PCSK9^{D374Y}$ protein, as measured by ELISA.
Figure 4:
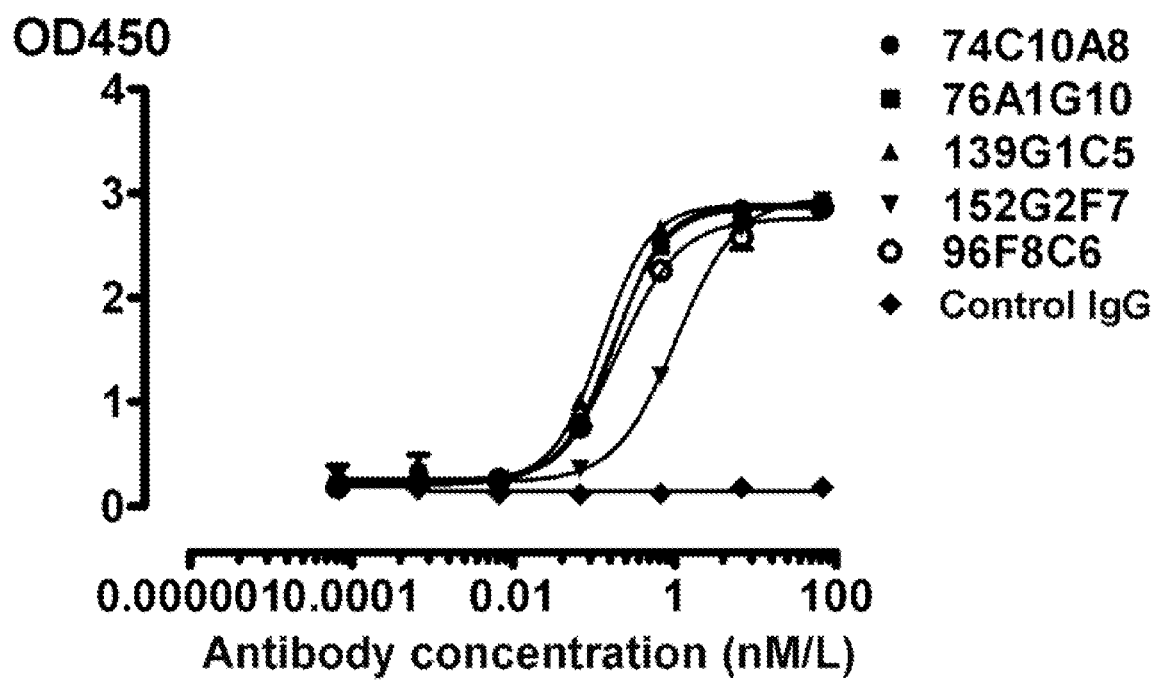
FIG. 4 shows the binding activity of chimeric anti-PCSK9 antibodies according to embodiments of the invention to recombinant cyno monkey PCSK9 protein, as measured by ELISA.

Streptavidin (Cat No. 85878, Sigma) was diluted with PBS to a final concentration of 1 ug/mL, 100 uL were added to each well of a 96-well ELISA plate that was then sealed with a plastic film and incubated overnight at 4° C. The next day, the plates were washed twice with wash buffer [0.01% (v/v) Tween 20], then blocked with blocking buffer [0.01% (v/v) 0.1% BSA (w/w) Tween 20] at room temperature for 2 hours. The blocking buffer was aspirated away, and 100 uL of 0.5 ug/mL biotinylated immunogen A (hPCSK9-His), biotinylated $PCSK9^{D374Y}$ or biotinylated cyno PCSK9 proteins (Biotin labeling kit, Invitrogen) were added to each well and incubated at 37° C. for 1 hour. Unbound PCSK9 proteins were removed by washing the plate three times with wash buffer [0.01% (v/v) Tween 20]. 200 uL of purified PCSK9 antibodies from Example 2 were added to each well and incubated for 1 hour at 37° C. The plates were washed twice with wash buffer [0.01% (v/v) Tween 20], and 200 uL HRP-conjugated secondary antibody (Sigma) was added to each well and incubated for 2 hours at 37° C. After the plates were washed three times with wash buffer, 100 ul TMB substrate were added to each well and incubated for 30 minutes at room temperature. 100 ul stop solution (0.1N HCl) were added to each well to stop the reaction. The absorbance at 450 nm was measured using an ELISA plate reader (384 plus SpectraMax, Molecular Device). The results are shown in FIGS. 2-4 and in Tables 8-10. The IgG control was rat IgG.

The extracellular domain of LDLR (SEQ ID NO: 64; corresponding to Ala22-Arg788 of full-length LDLR) was cloned along with a His tag (LDLR$^{ECD}$-His; prepared using the method of Example 1). Purified LDLR$^{ECD}$-His was diluted with PBS to a final concentration of 1.0 ug/ml, and 100 uL of diluted LDLR$^{ECD}$-His were added to each well of

TABLE 8

Binding activities of chimeric anti-PCSK9 mAbs to human PCSK9-His, as measured by ELISA

| | OD$_{450\,nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 74C10A8 | 2.98 | 2.99 | 2.89 | 1.15 | 0.30 | 0.17 | 0.19 | 0.22 |
| 76A1B11 | 2.85 | 2.85 | 2.66 | 0.86 | 0.27 | 0.21 | 0.20 | 0.18 |
| 139G1C5 | 2.93 | 2.94 | 2.87 | 1.55 | 0.36 | 0.21 | 0.19 | 0.22 |
| 152G2F7 | 2.91 | 2.91 | 2.42 | 0.60 | 0.25 | 0.21 | 0.18 | 0.17 |
| 96F8C6 | 2.86 | 2.89 | 2.73 | 1.00 | 0.30 | 0.18 | 0.17 | 0.20 |
| IgG control | 0.19 | 0.20 | 0.22 | 0.12 | 0.18 | 0.18 | 0.24 | 0.20 |
| 103C11E8 | 2.72 | 2.71 | 2.41 | 0.68 | 0.21 | 0.15 | 0.11 | 0.14 |
| IgG control | 0.11 | 0.10 | 0.09 | 0.09 | 0.10 | 0.09 | 0.11 | 0.10 |

TABLE 9

Binding activities of chimeric anti-PCSK9 mAbs to human PCSK9$^{D374Y}$, as measured by ELISA

| | OD$_{450\,nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 74C10A8 | 3.11 | 3.14 | 3.05 | 1.15 | 0.28 | 0.20 | 0.20 | 0.23 |
| 76A1B11 | 2.90 | 2.89 | 2.59 | 0.81 | 0.29 | 0.21 | 0.20 | 0.19 |
| 139G1C5 | 3.00 | 3.00 | 2.94 | 1.50 | 0.36 | 0.27 | 0.27 | 0.24 |
| 152G2F7 | 3.01 | 2.96 | 2.17 | 0.52 | 0.24 | 0.24 | 0.20 | 0.18 |
| 96F8C6 | 2.92 | 2.92 | 2.75 | 1.00 | 0.27 | 0.19 | 0.15 | 0.24 |
| IgG control | 0.25 | 0.20 | 0.20 | 0.14 | 0.13 | 0.18 | 0.23 | 0.14 |
| 103C11E8 | 2.80 | 2.82 | 2.61 | 0.81 | 0.21 | 0.15 | 0.15 | 0.14 |
| IgG control | 0.08 | 0.09 | 0.09 | 0.09 | 0.09 | 0.12 | 0.10 | 0.10 |

TABLE 10

Binding activities of chimeric anti-PCSK9 mAbs to Cyno Monkey PCSK9-His, as measured by ELISA

| | OD$_{450\,nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 74C10A8 | 2.89 | 2.86 | 2.53 | 0.76 | 0.27 | 0.34 | 0.18 | 0.21 |
| 76A1B11 | 2.88 | 2.82 | 2.50 | 0.81 | 0.26 | 0.23 | 0.21 | 0.19 |
| 139G1C5 | 2.90 | 2.88 | 2.67 | 1.00 | 0.27 | 0.26 | 0.23 | 0.20 |
| 152G2F7 | 2.93 | 2.67 | 1.25 | 0.35 | 0.20 | 0.21 | 0.27 | 0.33 |
| 96F8C6 | 2.87 | 2.58 | 2.26 | 0.77 | 0.25 | 0.23 | 0.19 | 0.25 |
| IgG control | 0.18 | 0.17 | 0.12 | 0.12 | 0.12 | 0.16 | 0.19 | 0.15 |

Example 4—Determination of the Ability of the Anti-PCSK9 Antibodies to Block the Binding of PCSK9 and PCSK9$^{D374Y}$ to LDLR Both wild type PCSK9 and its mutant PCSK9$^{D374Y}$ bind to LDLR, and the mutant form of PCSK9$^{D374Y}$ has higher binding affinity to LDLR than the wild type version. A receptor ligand binding assay was performed to determine the ability of the anti-PCSK9 antibodies to block the binding of PCSK9 and PCSK9$^{D374Y}$ to LDLR.

Figure 5:
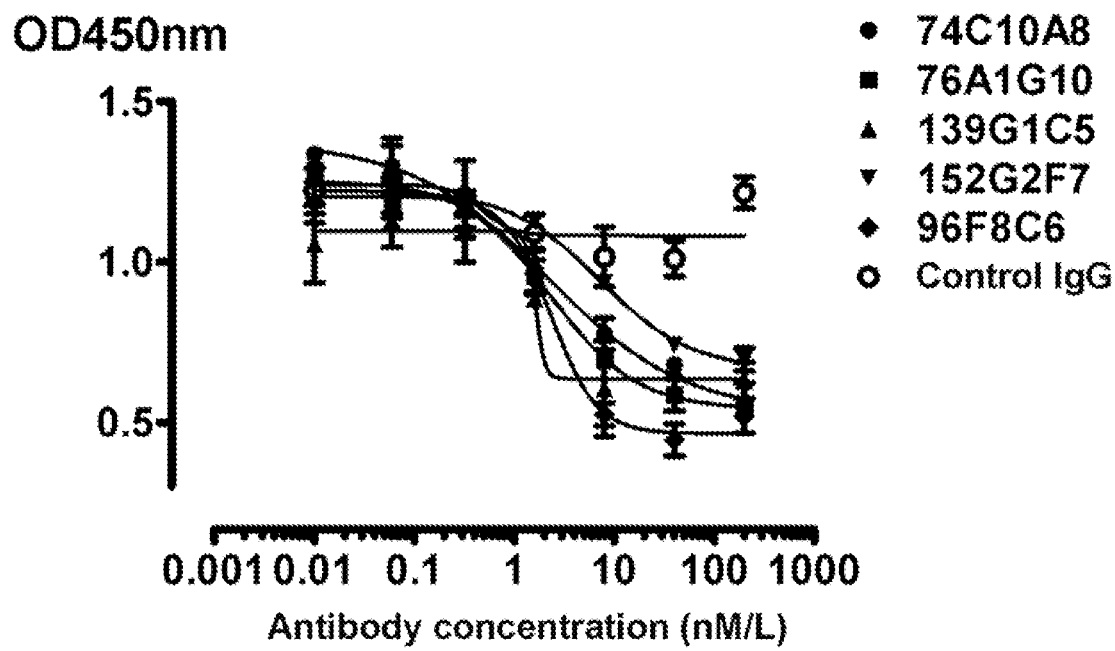
FIG. 5 shows the inhibition of binding of recombinant PCSK9 protein to LDLR ECD protein by chimeric anti-PCSK9 antibodies according to embodiments of the invention, as measured by ELISA.
Figure 6:
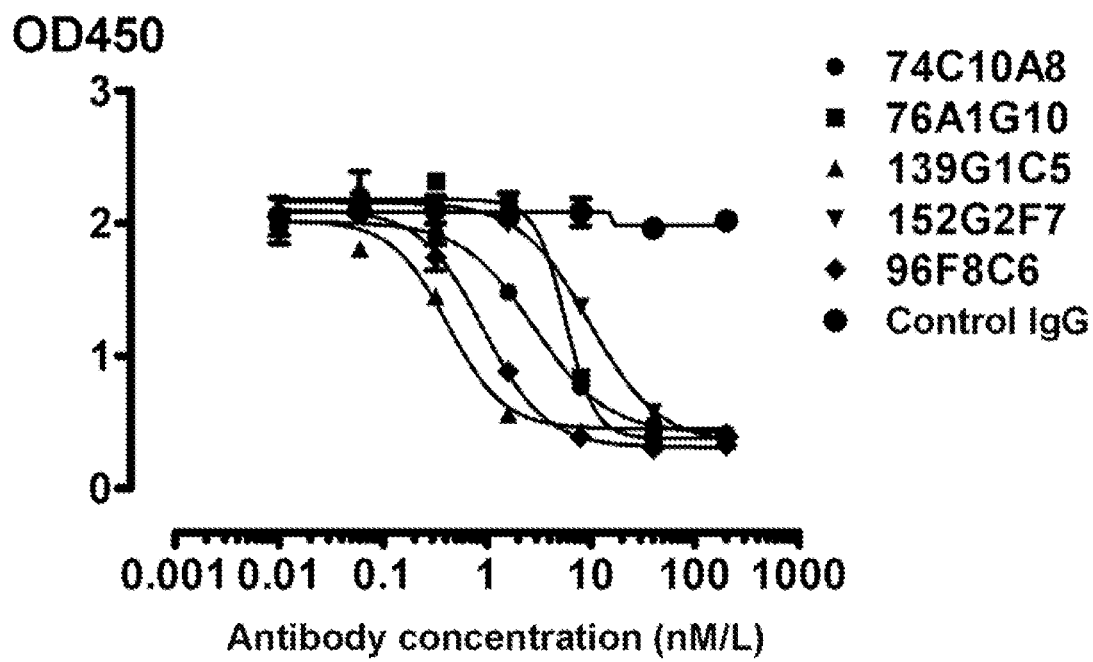
FIG. 6 shows the inhibition of binding of recombinant $PCSK9^{D374Y}$ protein to LDLR ECD protein by chimeric anti-PCSK9 antibodies according to embodiments of the invention, as measured by ELISA.

96-well plate that was then sealed with plastic film and incubated at 4° C. overnight. The plate was washed twice with wash buffer [PBS+0.01% (v/v) Tween 20] and incubated with blocking buffer [PBS+0.01% (v/v) BSA+1% Tween20 (w/w)] at room temperature for 2 hours. The blocking buffer was aspirated, and 50 uL purified anti-PCSK9 antibodies from Example 2 were added to each well of 96-well plate. 50 ul of 0.5 ug/mL biotinylated recombinant hPCSK9-His or biotinylated PCSK9$^{D374Y}$ protein (biotinylated using the Biotin labeling kit, Invitrogen) were added to each well, mixed, and incubated at 37° C. for 2 hours. The plate was washed three times with wash buffer [0.01% (v/v) Tween 20]. 100 uL HRP-conjugated streptavidin (Sigma) were then added to each well and incubated at 37° C. for 1 hour. The plate was then washed three times with wash buffer, and 100 uL TMB substrate were added to each well. After 15 minutes of incubation at room temperature, the reaction was stopped by adding 50 uL stop solution (0.1N HCl). The absorbance at OD450 nm was measured with an ELISA plate reader (384 plus SpectraMax, Molecular Devices). The results, shown in FIGS. 5-6 and in Tables 11-12, demonstrate that the anti-PCSK9 antibodies can block the binding of PCSK9 and PCSK9$^{D374Y}$ to LDLR.

TABLE 11

Inhibition of binding of human PCSK9 to LDLR by chimeric anti-PCSK9 mAbs, as measured by ELISA

| | $OD_{450\ nm}$ | | | | | |
|---|---|---|---|---|---|---|
| | Antibody concentration (nM) | | | | | |
| Clone ID | 200 | 40 | 8 | 1.6 | 0.32 | 0.06 | 0.01 |
| 74C10A8 | 0.55 | 0.68 | 0.78 | 0.97 | 1.20 | 1.30 | 1.34 |
| 76A1B11 | 0.55 | 0.59 | 0.70 | 0.96 | 1.19 | 1.18 | 1.29 |
| 139G1C5 | 0.63 | 0.67 | 0.61 | 0.89 | 1.11 | 1.13 | 1.06 |
| 152G2F7 | 0.70 | 0.74 | 0.94 | 1.20 | 1.17 | 1.20 | 1.26 |
| 96F8C6 | 0.63 | 0.45 | 0.53 | 0.97 | 1.16 | 1.25 | 1.19 |
| IgG control | 1.22 | 1.01 | 1.02 | 1.09 | 1.20 | 1.26 | 1.22 |
| 103C11E8 | 0.54 | 0.77 | 0.87 | 0.91 | 0.92 | 0.96 | 0.97 |
| IgG control | 1.14 | 1.11 | 1.07 | 1.12 | 1.13 | 1.20 | 1.18 |

TABLE 12

Inhibition of binding of human PCSK9$^{D374Y}$ to LDLR by chimeric anti-PCSK9 mAbs, as measured by ELISA

| | $OD_{450\ nm}$ | | | | | |
|---|---|---|---|---|---|---|
| | Antibody concentration (nM) | | | | | |
| Clone ID | 200 | 40 | 8 | 1.6 | 0.32 | 0.06 | 0.01 |
| 74C10A8 | 0.42 | 0.49 | 0.77 | 1.49 | 1.92 | 2.06 | 1.96 |
| 76A1B11 | 0.36 | 0.40 | 0.85 | 2.14 | 2.33 | 2.17 | 2.05 |
| 139G1C5 | 0.44 | 0.53 | 0.43 | 0.56 | 1.45 | 1.81 | 2.14 |
| 152G2F7 | 0.38 | 0.58 | 1.37 | 1.99 | 2.14 | 2.18 | 2.15 |
| 96F8C6 | 0.33 | 0.30 | 0.39 | 0.88 | 1.75 | 2.23 | 1.98 |
| IgG control | 2.02 | 1.97 | 2.09 | 2.05 | 2.11 | 2.11 | 2.06 |
| 103C11E8 | 0.19 | 0.91 | 1.51 | 1.12 | 1.04 | 1.03 | 1.02 |
| IgG control | 0.96 | 0.93 | 1.00 | 1.04 | 0.96 | 1.04 | 1.04 |

Example 5—Assay to Measure PCSK9-Mediated LDLR Degradation

Figure 7:
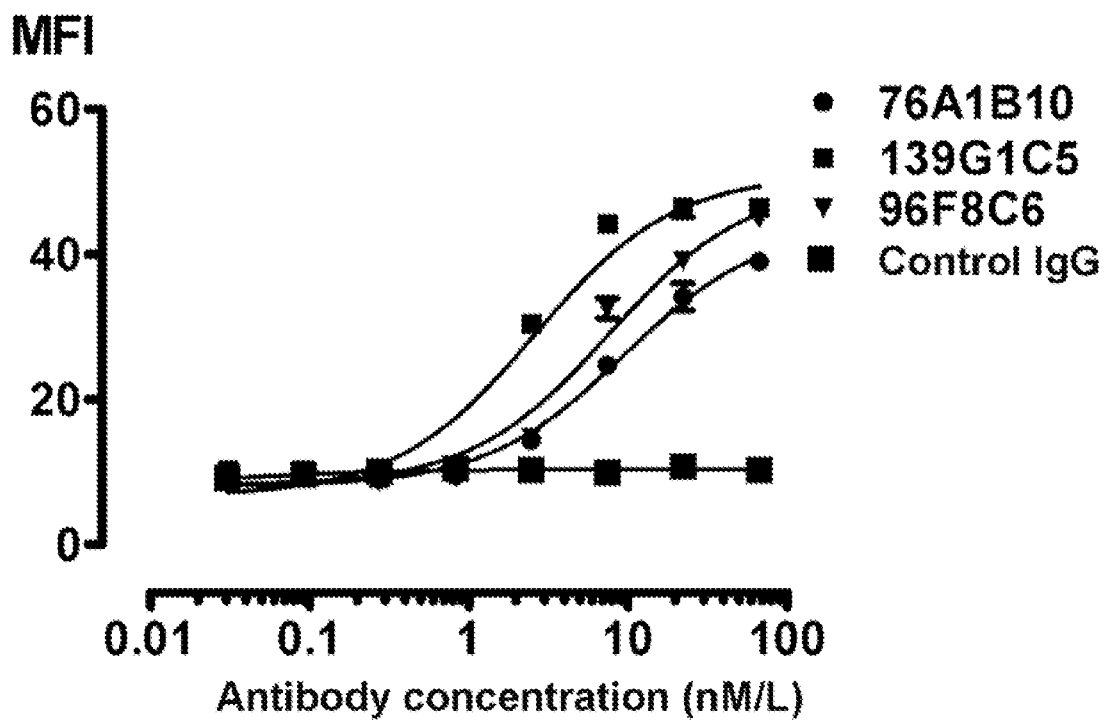
FIG. 7 shows the inhibition of $PCSK9^{D374Y}$-induced down regulation of LDLR by chimeric anti-PCSK9 antibodies according to embodiments of the invention, as determined by FACS.

Log phase HepG2 cells (ATCC) were digested with trypsin, centrifuged and resuspended in MEM medium (Invitrogen Cat No. 11095-080) supplemented with 10% (w/w) fetal bovine serum. The cell density was adjusted to 3×10$^5$ cells/mL, and cells were added to each well of 24-well plate. After the places were incubated for 6 hours to allow the HepG2 cells to adhere, the culture medium was aspirated and replenished with MEM medium supplemented with 10% (w/w) LPDS (Kalen Biomedical LLC, 880100-2) and incubated overnight. The next day, 0.4 ug/mL PCSK9$^{D374Y}$ and anti-PCSK9 antibodies from Example 2 were mixed and added to the 24-well plate, which was incubated for 4 hours at 37° C. MEM medium supplemented with 10% LPDS was removed, and the plates were washed twice with PBS. The HepG2 cells were dissociated from the plate using Versene solution (Invitrogen) and collected. The cells were washed twice with PBS, the cell counts were determined, and the cell density was adjusted to 2×10$^6$ cells/mL with PBS. Blocking buffer [1% (w/w) FBS PBS] was added to the cell suspension, and 100 uL of the cell suspension were added to each well of 96-well FACS plate (FACS Calibur, BD) that was incubated on ice for 15 minutes, then centrifuged. The blocking buffer was aspirated away, and 100 uL of 1 ug/uL LDLR antibody (Progen, 61009) was added to each well and incubated on ice for 15 minutes. The plates were washed twice with FACS buffer [1% (w/w) BSA HBSS], and 100 uL Alexa-488-conjugated anti-rabbit secondary antibody (Molecular Probes, A-11034) were added to each well and incubated on ice for 15 minutes. The plates were washed three times with FACS buffer and resuspended in 100 uL FACS buffer after the final wash. The Mean Fluorescence Intensity (MFI) was determined using FACS Calibur (BD), and the results are shown in FIG. 7 and in Table 13. The IgG control was rat IgG, and the values in the table are the mean fluorescence intensities of the cell populations. The results showed that the anti-PCSK9 antibodies inhibited PCSK9$^{D374Y}$-induced LDLR degradation in HepG2 cells in a dose dependent manner.

TABLE 13

Effect of chimeric anti-PCSK9 mAbs on human PCSK9$^{D374Y}$-mediated down regulation of LDLR

| | Mean fluorescence intensity | | | | | | | |
|---|---|---|---|---|---|---|---|---|
| | Antibody concentration (nM) | | | | | | | |
| Clone ID | 66.70 | 22.23 | 7.41 | 2.47 | 0.82 | 0.27 | 0.09 | 0.03 |
| 74C10A8 | 39.1 | 34.2 | 24.8 | 14.4 | 9.6 | 9.0 | 9.2 | 9.2 |
| 139G1C5 | 46.5 | 46.5 | 44.3 | 30.4 | 10.7 | 9.3 | 10.2 | 10.1 |
| 96F8C6 | 44.9 | 39.1 | 32.6 | 14.7 | 10.5 | 8.7 | 10.3 | 10.3 |
| IgG control | 10.3 | 10.7 | 10.0 | 10.3 | 10.5 | 10.0 | 9.7 | 9.2 |

Figure 8:
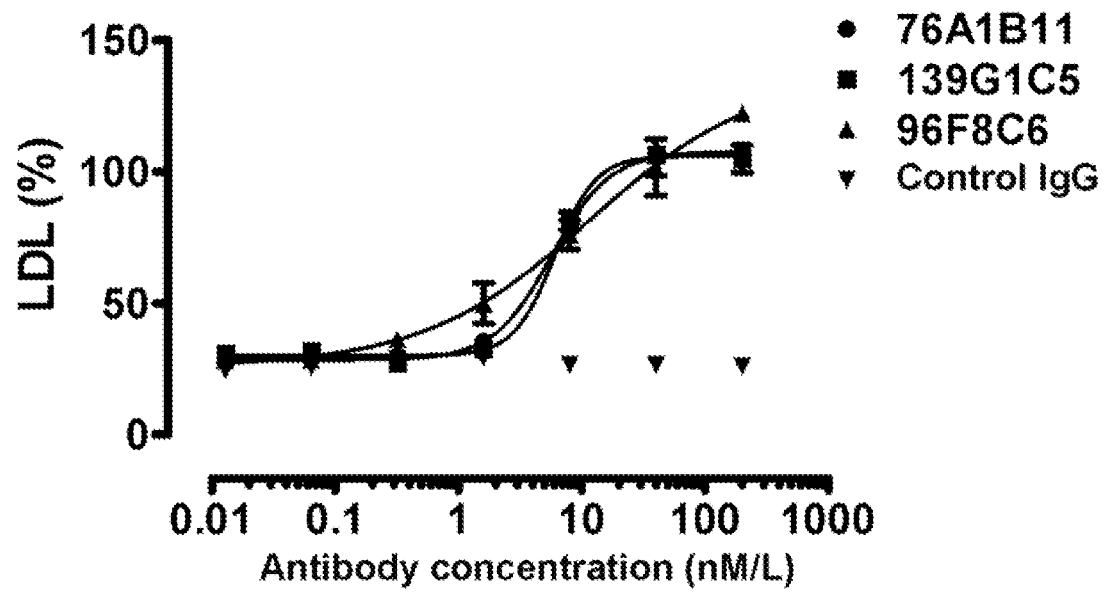
FIG. 8 shows the inhibition of $PCSK9^{D374Y}$-induced LDL uptake in HepG2 cells by chimeric anti-PCSK9 antibodies according to embodiments of the invention.
Figure 9:
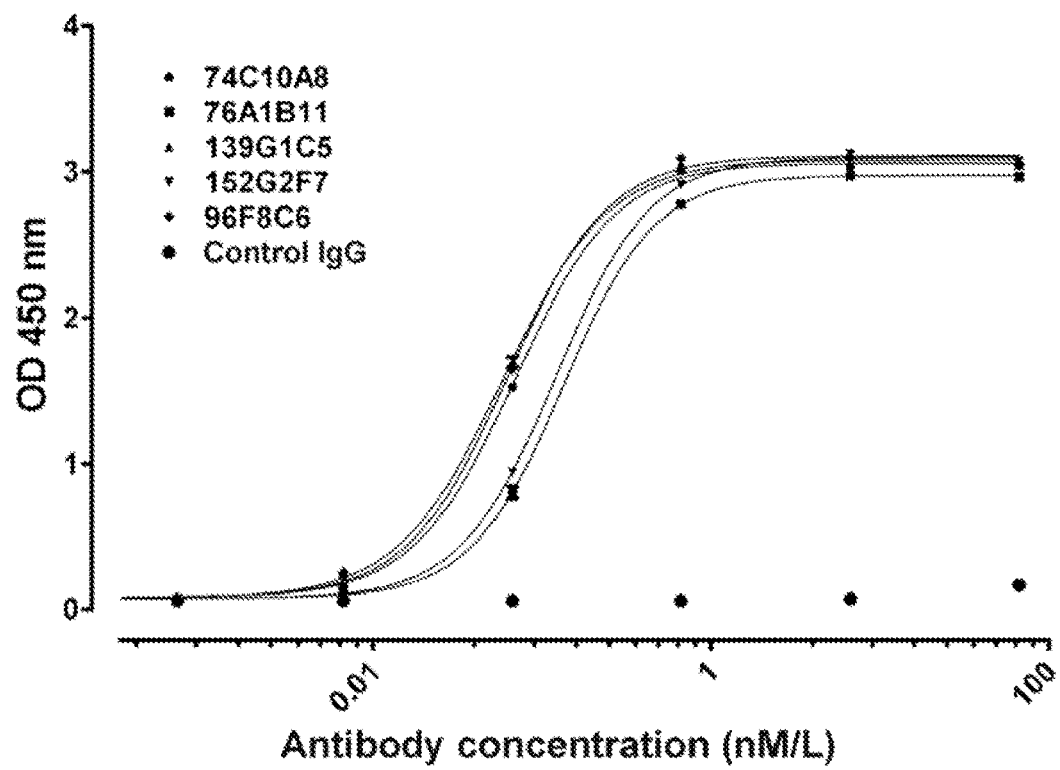
FIG. 9 shows the binding activity of fully human anti-PCSK9 antibodies according to embodiments of the invention to Immunogen A (hPCSK9-His), as measured by ELISA.
Figure 10:
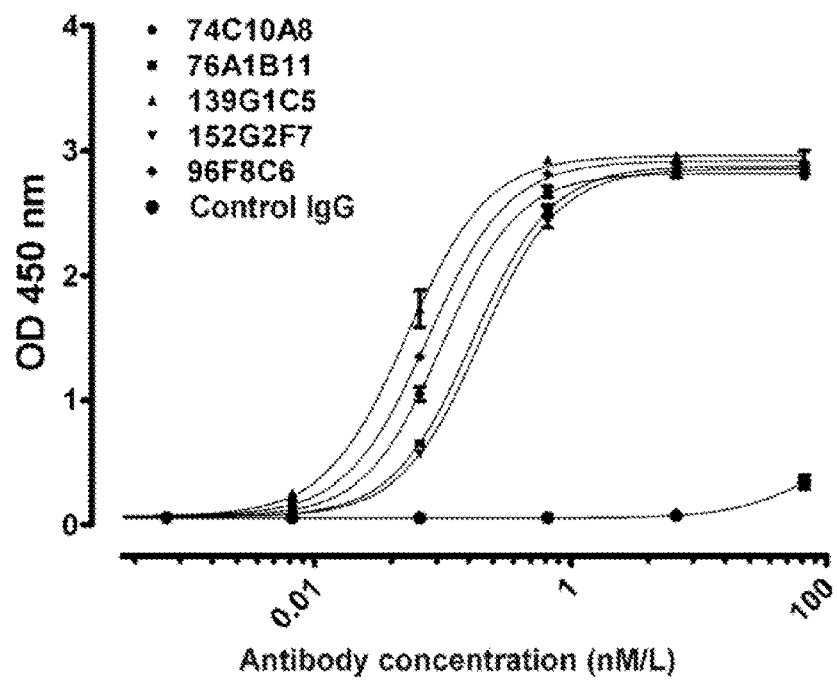
FIG. 10 shows the binding activity of fully human anti-PCSK9 antibodies according to embodiments of the invention to recombinant $PCSK9^{D374Y}$ protein, as measured by ELISA.
Figure 11:
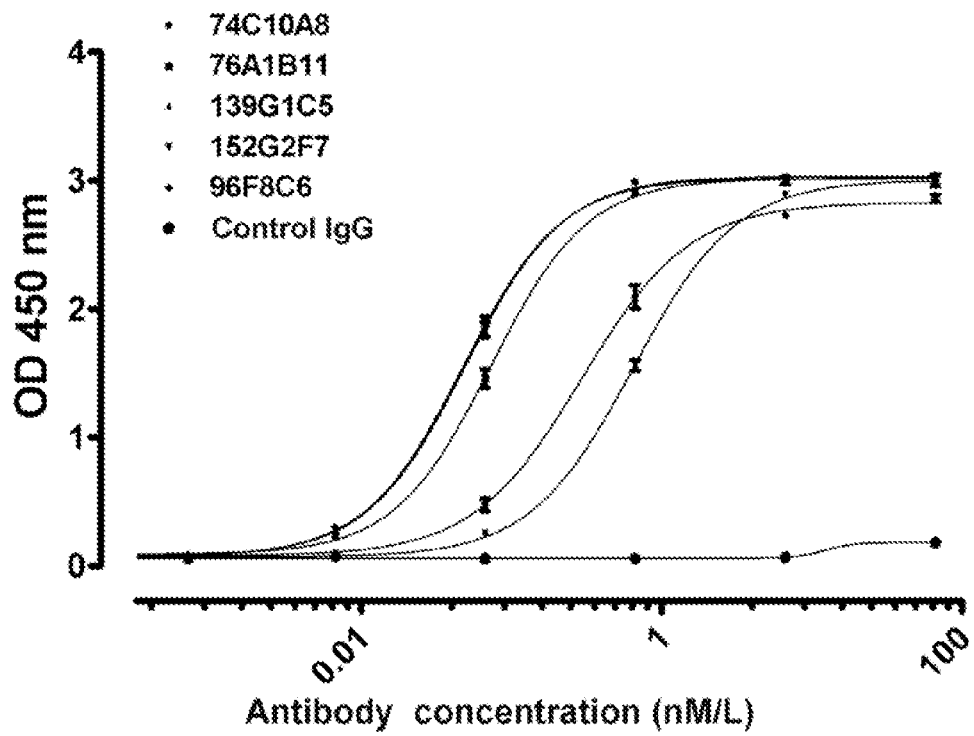
FIG. 11 shows the binding activity of fully human anti-PCSK9 antibodies according to embodiments of the invention to cyno monkey PCSK9, as measured by ELISA.
Figure 12:
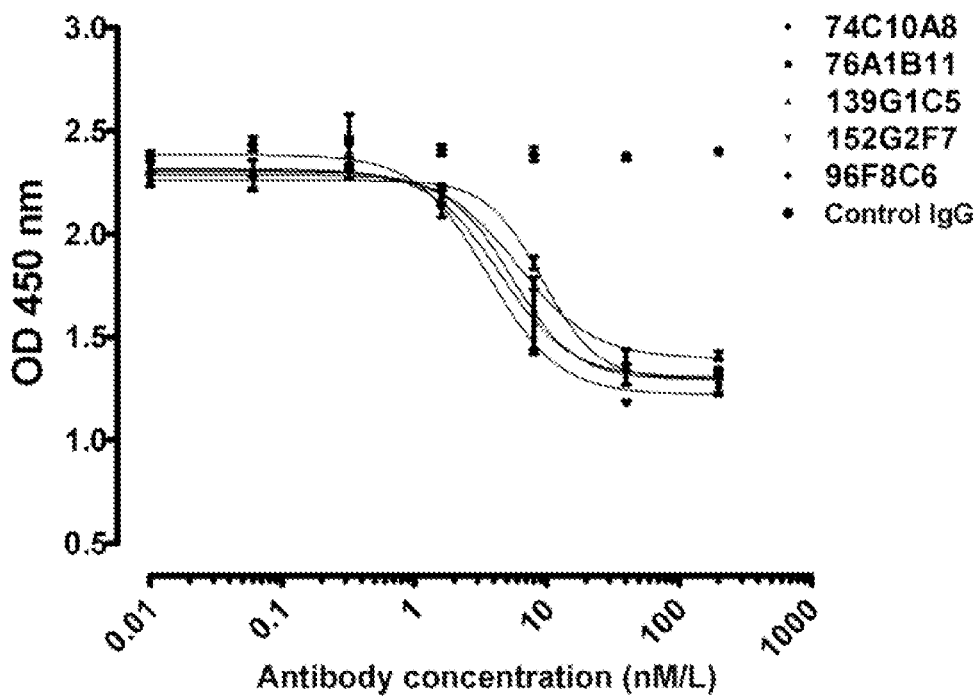
FIG. 12 shows the inhibition of binding of recombinant PCSK9 protein to LDLR ECD protein by fully human anti-PCSK9 antibodies according to embodiments of the invention, as measured by ELISA.
Figure 13:
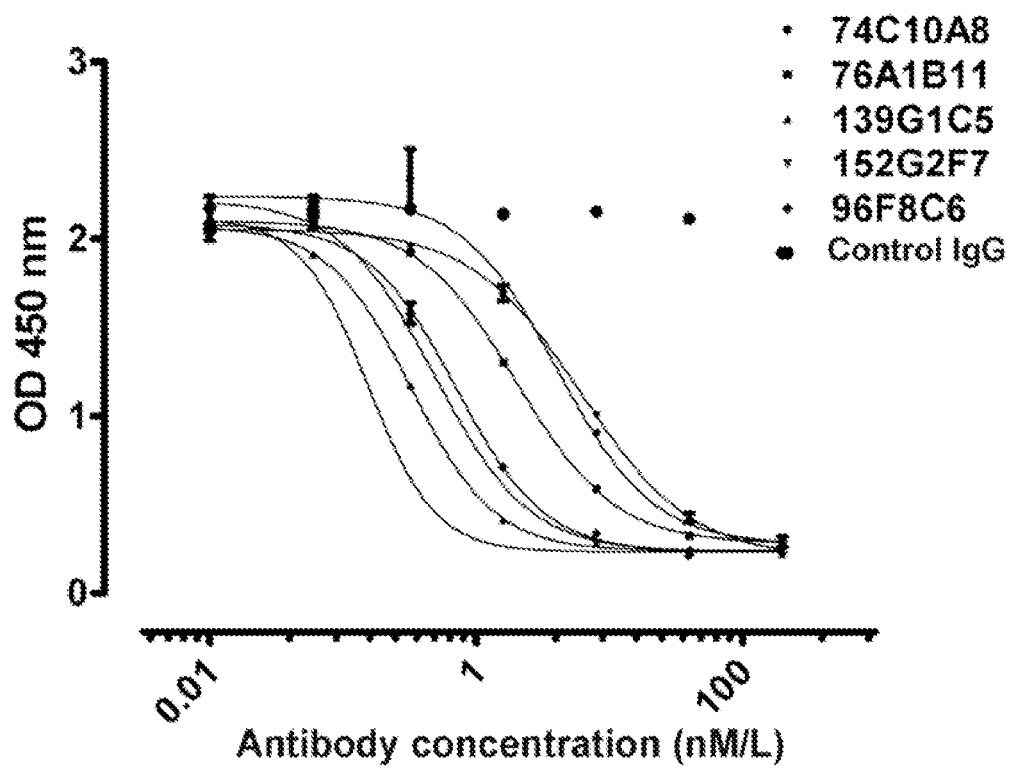
FIG. 13 shows the inhibition of binding of recombinant PCSK9$^{D374Y}$ protein to LDLR ECD protein by fully human anti-PCSK9 antibodies according to embodiments of the invention, as measured by ELISA.
Figure 14:
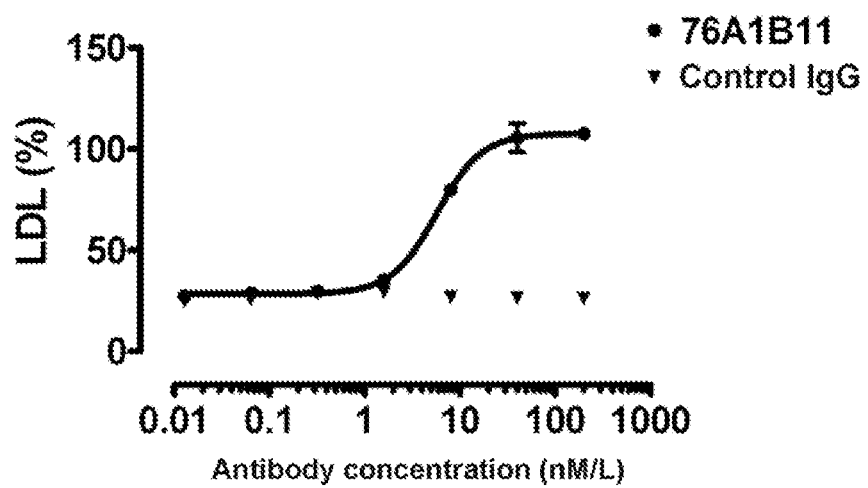
FIG. 14 shows the inhibition of PCSK9$^{D374Y}$-induced LDL uptake in HepG2 cells by a fully human anti-PCSK9 antibody according to embodiments of the invention.
Figure 15:
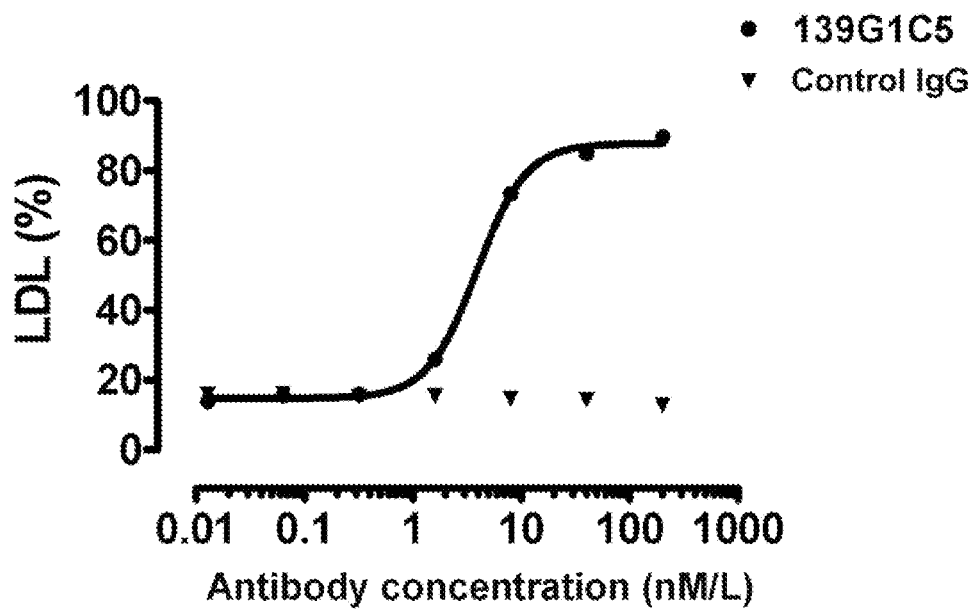
FIG. 15 shows the inhibition of PCSK9$^{D374Y}$-induced LDL uptake in HepG2 cells by a fully human anti-PCSK9 antibody according to embodiments of the invention.
Figure 16:
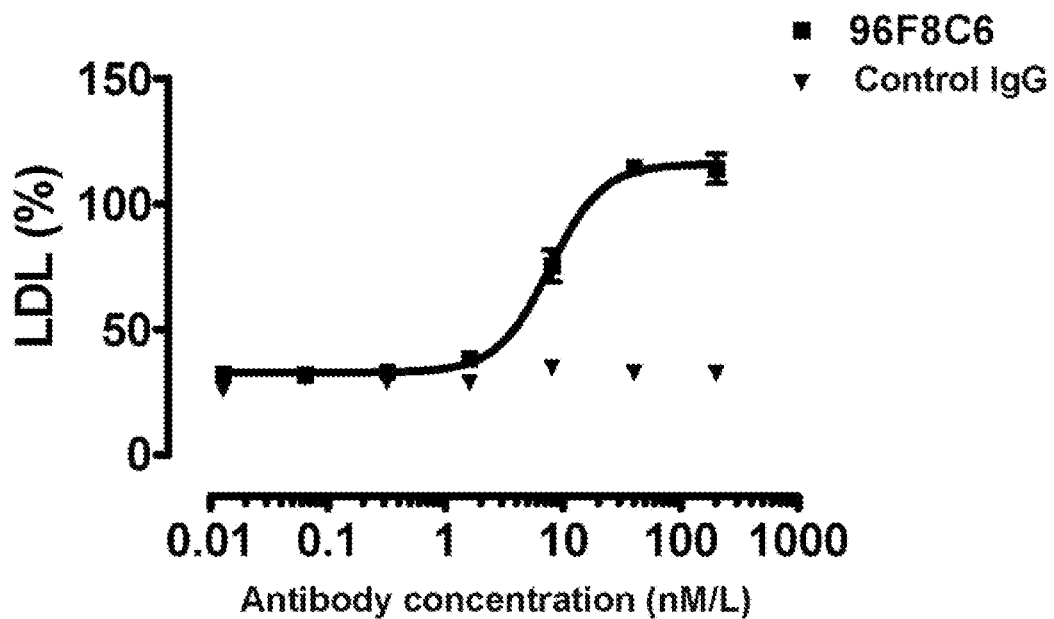
FIG. 16 shows the inhibition of PCSK9$^{D374Y}$-induced LDL uptake in HepG2 cells by a fully human anti-PCSK9 antibody according to embodiments of the invention.
Figure 17:
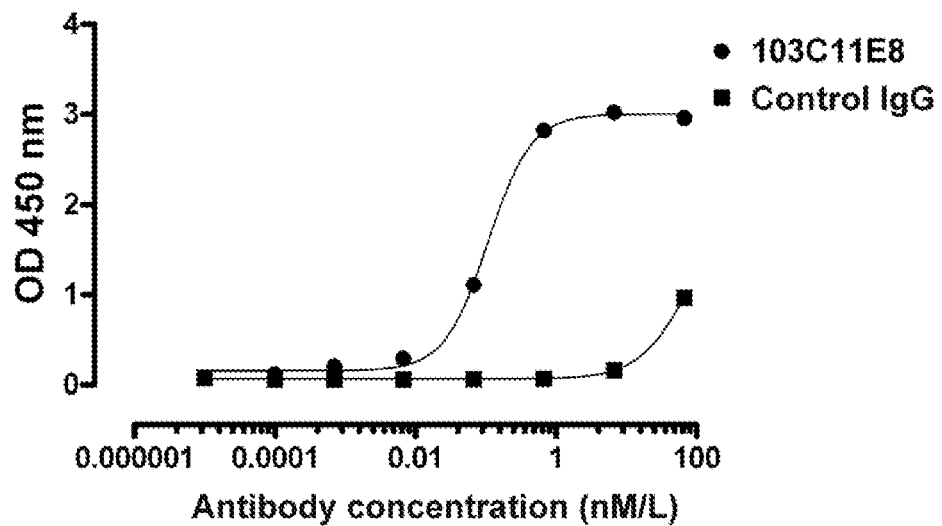
FIG. 17 shows the binding activity of a fully human anti-PCSK9 antibody according to embodiments of the invention to Immunogen A, as measured by ELISA.
Figure 18:
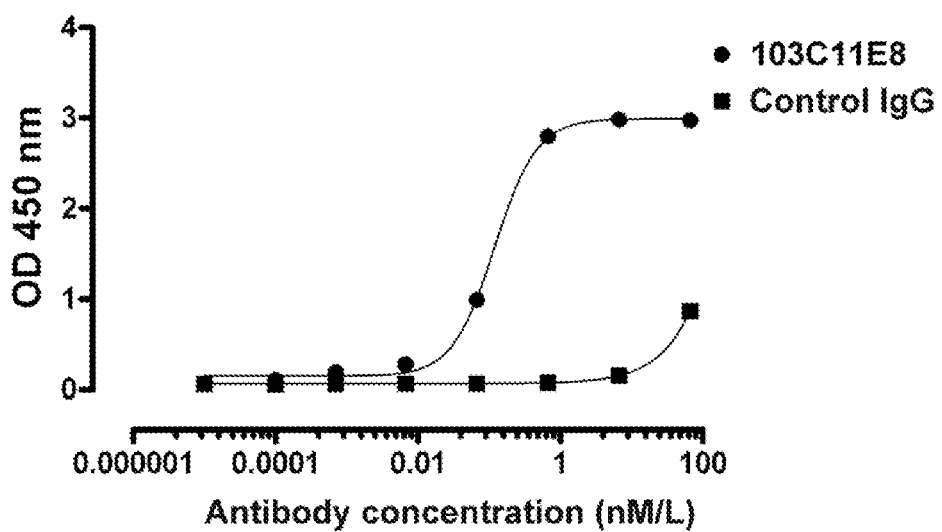
FIG. 18 shows the binding activity of a fully human anti-PCSK9 antibody according to embodiments of the invention to recombinant PCSK9$^{D374Y}$ protein, as measured by ELISA.
Figure 19:
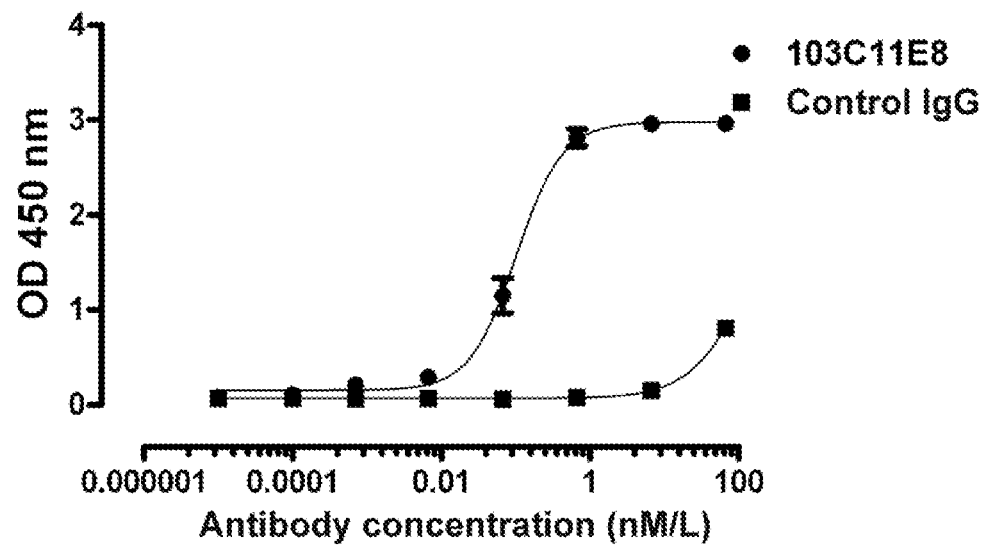
FIG. 19 shows the binding activity of a fully human anti-PCSK9 antibody according to embodiments of the invention to cyno monkey PCSK9, as measured by ELISA.
Figure 20:
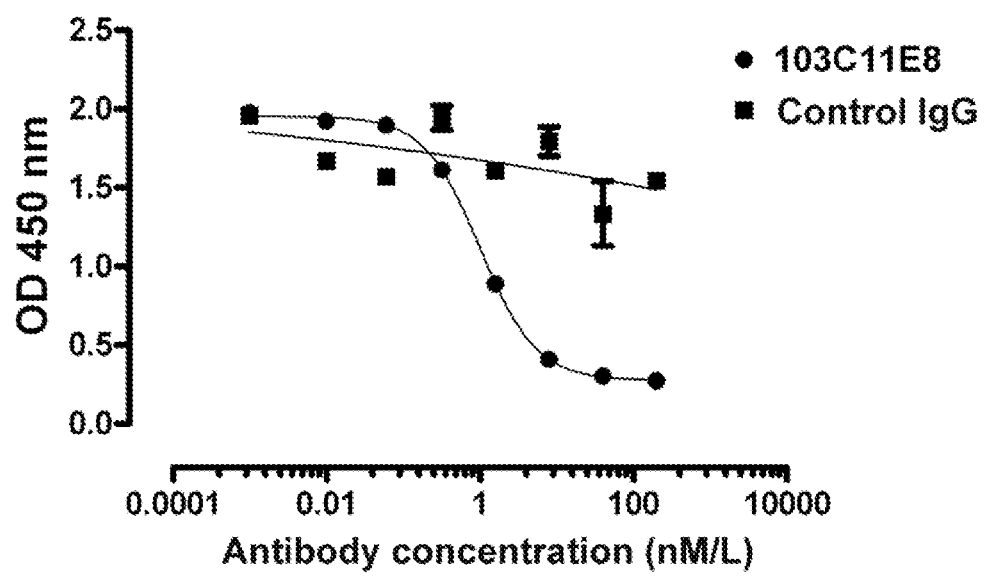
FIG. 20 shows the inhibition of binding of recombinant PCSK9 protein to LDLR ECD protein by a fully human anti-PCSK9 antibody according to embodiments of the invention, as measured by ELISA.
Figure 21:
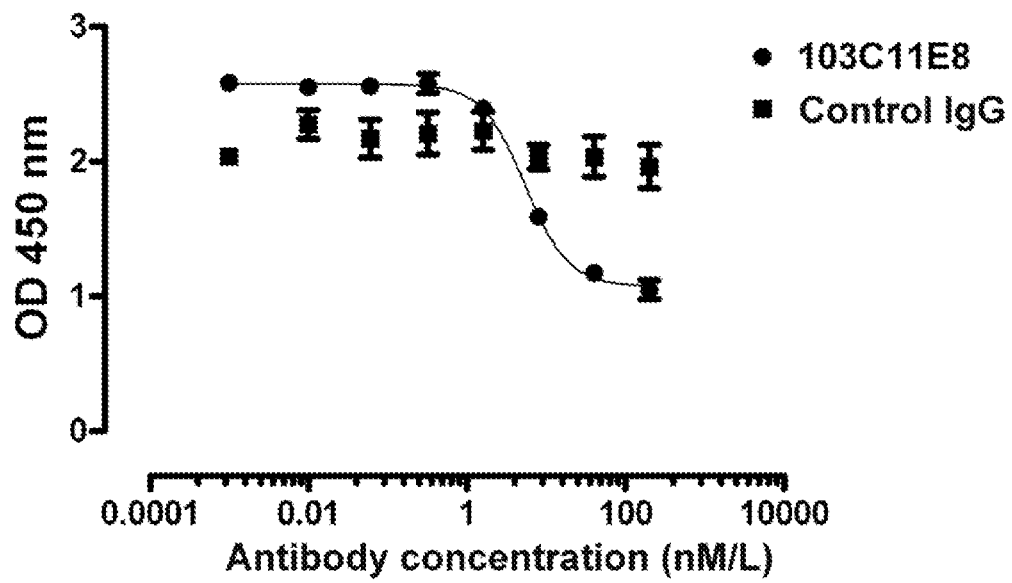
FIG. 21 shows the inhibition of binding of recombinant PCSK9$^{D374Y}$ to LDLR ECD protein by a fully human anti-PCSK9 antibody according to embodiments of the invention, as measured by ELISA.
Figure 22:
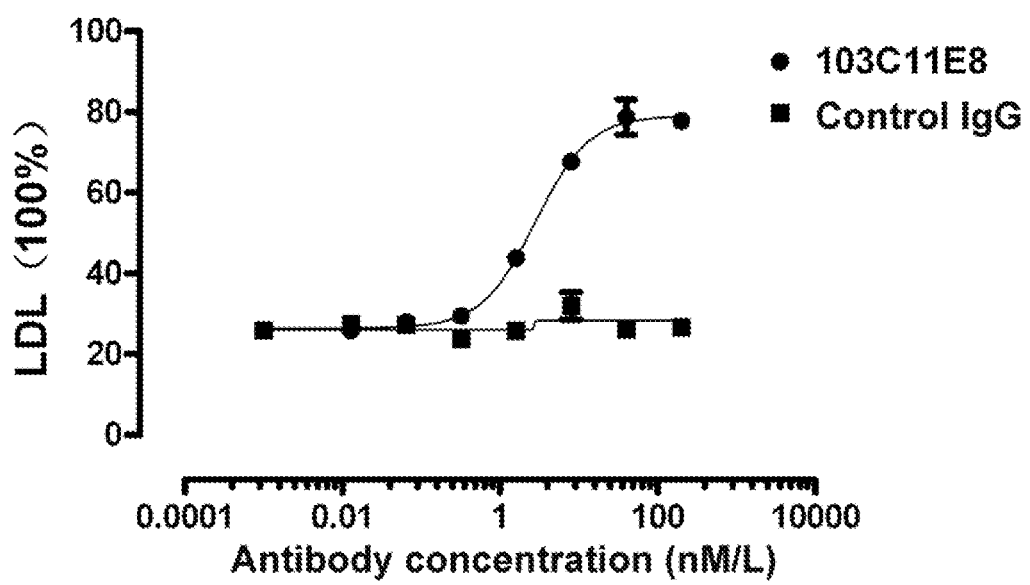
FIG. 22 shows the inhibition of PCSK9$^{D374Y}$-induced LDL uptake in HepG2 cells by a fully human anti-PCSK9 antibody according to embodiments of the invention, as measured by ELISA.

Example 6—Assay to Measure Inhibition of PCSK9-Mediated LDL Uptake in HepG2 Cells Log phase HepG2 cells (ATCC) were digested with trypsin, centrifuged and resuspended in MEM medium (Invitrogen Cat No. 11095-080) supplemented with 10% (w/w) fetal bovine serum. The cell density was adjusted to 5×10$^5$ cells/mL, and cells were added to a PDL-coated (Millipore, A-003-E) 96-well plate. After the places were incubated for 6 hours to allow the HepG2 cells to adhere, the culture medium was aspirated and replenished with MEM medium supplemented with 10% (w/w) LPDS (Kalen Biomedical LLC, 880100-2) and incubated overnight. 10 ug/mL of BODIPY® FL LDL (Invitrogen, L3483), 0.5 ug/mL of PCSK9$^{D374Y}$, and anti-PCSK9 antibodies from Example 2 were mixed and added to the 96-well plate, which was incubated for 6 hours. The culture medium was aspirated, the plates were washed twice with PBS, and the fluorescence intensity at 520 nm/485 nm was measured using an MS plate reader (Molecular Device). The results, shown in FIG. 8 and in Tables 14 and 15, indicated that the anti-PCSK9 antibodies blocked PCSK9$^{D374Y}$-mediated inhibition of LDL uptake in a dose-dependent manner.

TABLE 14

Effect of chimeric anti-PCSK9 mAbs on human PCSK9$^{D374Y}$-mediated inhibition of LDL uptake

| Clone ID | LDL (%) Antibody concentration (nM) | | | | | | | |
|---|---|---|---|---|---|---|---|---|
| | 200 | 40 | 8 | 1.6 | 0.32 | 0.06 | 0.01 | 0 |
| 74C10A8 | 107.4 | 105.4 | 79.8 | 35.4 | 29.6 | 28.8 | 27.4 | 24.4 |
| 139G1C5 | 104.9 | 106.4 | 81.2 | 32.6 | 27.1 | 31.6 | 31.0 | 27.2 |
| 96F8C6 | 122.15 | 101.6 | 76.0 | 49.9 | 36.2 | 28.5 | 28.4 | 32.6 |
| IgG control | 26.0 | 26.5 | 26.6 | 29.3 | 28.8 | 25.8 | 24.5 | 24.4 |

TABLE 15

Effect of chimeric anti-PCSK9 mAbs on human PCSK9$^{D374Y}$-mediated inhibition of LDL uptake

| Clone ID | LDL (%) Antibody concentration (nM) | | |
|---|---|---|---|
| | 66.70 | 6.67 | 0.67 |
| 103C11E8 | 86.4 | 43.8 | 20.0 |
| IgG control | 25.8 | 27.9 | 28.4 |

Example 7—Determination of the Amino Acid Sequences in the Variable Regions of the Anti-PCSK9 Antibodies Total RNA isolation: After the supernatants from the hybridoma subclones obtained from Example 2 were characterized (i.e., validation and determination of bioactivity, Examples 3-6), 5×10$^7$ hybridoma cells were collected by centrifugation. 1 mL Trizol was added to the cell pellets, mixed and transferred to 1.5 mL centrifuge tubes, and incubated at room temperature for 5 minutes. 0.2 mL chloroform was added to the samples and vortexed for 15 seconds. After standing for 2 minutes, the mixtures were centrifuged at 12000 g at 4° C. for 5 minutes. The supernatants were collected and transferred to new 1.5 mL centrifuge tubes, 0.5 mL isoprpyl alcohol was added and mixed gently, and the samples were incubated at room temperature for 10 minutes. The samples were centrifuged at 12000 g at 4° C. for 15 minutes. The supernatants were aspirated, and the precipitates were washed with 1 mL 75% (v/v) ethanol. The mixtures were centrifuged at 12000 g at 4° C. for 5 minutes, the supernatants were decanted, and the precipitates were air-dried. Total RNA was obtained by adding DEPC-treated water to the precipitates (55° C. water bath for 10 minutes).

Reverse transcription and PCR: 1 ug of RNA and reverse transcriptase were added to a reaction mixture of a final volume of 20 uL, and the mixture was incubated at 42° C. for 60 minutes and then at 70° C. for 10 minutes to terminate the reaction. A 50 uL PCR reaction mixture was prepared, containing 1 uL cDNA, 25 pmol of each primer, 1 uL DNA polymerase, 250 umol dNTPs, and the buffer system. The PCR program settings were as follows: denaturation at 95° C. for 3 minutes, 35 cycles of denaturation (95° C. for 30 seconds), annealing (55° C. for 30 seconds) and elongation (72° C. for 35 seconds), followed by a final extension at 72° C. for 5 minutes to obtain the PCR product. The commercially available reverse transcription kit used was Prime-Script RT Master Mix (Takara, RR036), and the commercially available Q5 ultra-fidelity polymerase PCR kit was from NEB (M0492).

Cloning and sequencing: 5 uL PCR products were examined by agarose gel electrophoresis, and the samples were recovered from the agarose gel using NucleoSpin Gel & PCR Clean-up kit (MACHEREY-NAGEL, 740609). Ligation reaction: To a 50 ng sample, 50 ng T vector, 0.5 uL ligase, and 1 uL buffer were added and brought to a final volume of 10 uL with water. The reaction mixture was incubated at 16° C. for 30 minutes using the T4 DNA Ligase (NEB, M0402). 5 uL ligation product was added to 100 uL competent cells (E cos 101 competent cells, Yeastern, FYE607), which were incubated on ice for 5 minutes, heat shocked at 42° C. for 1 minute and incubated on ice again for 1 minute. Cells were recovered by adding 650 uL SOC medium without antibiotics and incubating at 37° C. in a shaking incubator for 30 minutes at 200 rpm. 200 uL of each bacterial culture was spread onto an LB agar plate containing antibiotics at 37° C. overnight. The next day, PCR reactions were set up using the T vector primers M13F and M13R. Pipette tips were used to pick bacterial colonies and were dipped into the PCR reaction mixture and pipetted up and down. Half of the reaction mixture was transferred to an LB agar plate containing 100 nM ampicillin. After the PCR reactions, 5 uL of the PCR products were removed and examined by agarose gel electrophoresis, and positive samples were sent for sequencing and analysis (Kabat, 1991, "Sequences of proteins of objective interest," the NIH, Bethesda, Md.). The sequencing results are shown in Tables 1-2.

Example 8—Conversion, Expression and Purification of Fully Human Anti-PCSK9 Antibody (Step 1) Plasmid construction and preparation: Sequences of the anti-PCSK9 antibody heavy and light chain variable regions were obtained according to Example 7. The anti-PCSK9 antibodies' heavy chain variable region sequences were subcloned into expression vectors containing a signal peptide and a human heavy chain IgG1 constant region. The anti-PCSK9 antibodies' light chain variable region sequences were subcloned into expression vectors containing a signal peptide and a human antibody light chain kappa constant region. The recombinant plasmids were verified and confirmed by sequencing (the sequencing method was the same as in Example 7). Alkaline lysis was performed using a reagent kit (MACHEREY-NAGEL) to improve the purity and quality of the recombinant plasmids, and the plasmids were filtered through 0.22 uM filters (Millpore). The purified plasmids were used for transfection.

(Step 2) Transfection: HEK293E cells (Invitrogen) were cultured in FreeStyle 293 medium (Invitrogen) at 37° C., 130 RPM, 8% CO$_2$ (v/v). HEK293E cells were adjusted to 1-1.5×10$^6$/mL cell density for transfection. 10% (v/v) F68 (Invitrogen) was added to the FreeStyle 293 medium to a final concentration of 0.1% (v/v), as Medium A. 5 mL of Medium A and 200 ug/mL PEI (Sigma) were mixed to generate Medium B. 5 mL of Medium A and 100 ug/mL recombinant plasmid from step 1 were mixed to generate Medium C. After 5 minutes of incubation, Medium B and Medium C were mixed and incubated for 15 minutes to generate Mixture D. 10 mL of Mixture D were slowly added to 100 mL HEK293E cells with continuous stirring to avoid local accumulation of PEI. HEK293E cells were incubated overnight while shaking. The next day, peptone was added to a final concentration of 0.5% (w/v). On about day 5-7, the antibodies' titers were determined. On about day 6-7, the HEK293E cultures were centrifuged (30 minutes, 3500 RPM), and the supernatants were collected and filtered through 0.22 uM filters for purification.

(Step 3) Antibody purification: Protein A columns (GE) were washed with 0.1M NaOH for 30 minutes or with 5 bed volumes of 0.5M NaOH to get rid of endotoxin. Columns that had not been used in a long time were soaked in 1M NaOH for at least 1 hour, washed with endotoxin-free water to a neutral pH, and washed with 10 bed volumes of 1% Triton X100. The columns were then equilibrated with 5 bed volumes of PBS (PBS phosphate buffer, pH7.2). The filtered supernatants from Step 2 were loaded onto the columns, and the flow through was collected, if necessary. The columns were washed with 5 bed volume of PBS and then eluted with bed volumes of 0.1M Glycine-HCl pH3.0. The eluate containing anti-PCSK9 antibody was neutralized with 0.5 bed volume of 1M Tris-HCl (NaCl 1.5M) pH8.5. The human anti-PCSK9 antibodies were dialyzed in 1×PBS for 4 hours, to avoid endotoxin contamination. After dialysis, anti-PCSK9 antibodies' concentrations were determined by spectrophotometry or a reagent kit, the purities of the antibodies were determined by HPLC-SEC, and the levels of endotoxin were determined by an endotoxin test kit (Lonza). The fully human anti-PCSK9 antibodies were characterized, and the results are shown in FIGS. 9-11 and 17-19, and in Tables 16-21.

TABLE 16

Binding activities of fully human anti-PCSK9 mAbs to human PCSK9, as measured by ELISA

| | $OD_{450\,nm}$ | | | | | | | |
|---|---|---|---|---|---|---|---|---|
| | Antibody concentration (nM) | | | | | | | |
| Clone ID | 66.67 | 6.67 | 0.67 | 0.067 | 0.0067 | 0.00067 | 0.000067 | 0 |
| 74C10A8 | 3.04 | 3.04 | 3.00 | 1.52 | 0.23 | 0.08 | 0.06 | 0.06 |
| 76A1B11 | 2.97 | 2.97 | 2.77 | 0.80 | 0.14 | 0.07 | 0.06 | 0.06 |
| 139G1C5 | 3.04 | 3.06 | 3.05 | 1.70 | 0.26 | 0.08 | 0.06 | 0.06 |
| 152G2F7 | 3.07 | 3.12 | 2.91 | 0.94 | 0.15 | 0.07 | 0.06 | 0.06 |
| 96F8C6 | 3.06 | 3.10 | 3.09 | 1.65 | 0.25 | 0.08 | 0.06 | 0.06 |
| IgG control | 0.16 | 0.07 | 0.06 | 0.06 | 0.06 | 0.06 | 0.06 | 0.06 |

TABLE 17

Binding activities of fully human anti-PCSK9 mAbs to human PCSK9, as measured by ELISA

| | $OD_{450\,nm}$ | | | | | | | |
|---|---|---|---|---|---|---|---|---|
| | Antibody concentration (nM) | | | | | | | |
| Clone ID | 66.67 | 6.67 | 0.67 | 0.067 | 0.0067 | 0.00067 | 0.000067 | 0 |
| 103C11E8 | 2.96 | 3.02 | 2.83 | 1.11 | 0.29 | 0.21 | 0.12 | 0.08 |
| IgG control | 0.97 | 0.16 | 0.07 | 0.07 | 0.06 | 0.06 | 0.06 | 0.07 |

TABLE 18

Binding activities of fully human anti-PCSK9 mAbs to human $PCSK9^{D374Y}$, as measured by ELISA

| | $OD_{450\,nm}$ | | | | | | | |
|---|---|---|---|---|---|---|---|---|
| | Antibody concentration (nM) | | | | | | | |
| Clone ID | 66.67 | 6.67 | 0.67 | 0.067 | 0.0067 | 0.00067 | 0.000067 | 0 |
| 74C10A8 | 2.79 | 2.81 | 2.67 | 1.05 | 0.17 | 0.07 | 0.06 | 0.05 |
| 76A1B11 | 2.87 | 2.86 | 2.52 | 0.66 | 0.13 | 0.06 | 0.06 | 0.06 |
| 139G1C5 | 2.91 | 2.96 | 2.93 | 1.73 | 0.27 | 0.08 | 0.06 | 0.06 |
| 152G2F7 | 2.85 | 2.84 | 2.44 | 0.57 | 0.11 | 0.07 | 0.05 | 0.06 |
| 96F8C6 | 2.91 | 2.90 | 2.81 | 1.35 | 0.21 | 0.07 | 0.06 | 0.06 |
| IgG control | 0.35 | 0.08 | 0.06 | 0.06 | 0.06 | 0.06 | 0.06 | 0.06 |

TABLE 19

Binding activities of fully human anti-PCSK9 mAbs to human PCSK9$^{D374Y}$, as measured by ELISA

| | $OD_{450\ nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 103C11E8 | 2.98 | 2.99 | 2.80 | 0.99 | 0.28 | 0.19 | 0.11 | 0.07 |
| IgG control | 0.87 | 0.15 | 0.08 | 0.07 | 0.07 | 0.06 | 0.06 | 0.07 |

TABLE 20

Binding activities of fully human anti-PCSK9 mAbs to Cyno Monkey PCSK9, as measured by ELISA

| | $OD_{450\ nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 74C10A8 | 2.86 | 2.73 | 2.10 | 0.48 | 0.11 | 0.06 | 0.13 | 0.06 |
| 76A1B11 | 3.00 | 3.00 | 2.91 | 1.46 | 0.24 | 0.08 | 0.11 | 0.07 |
| 139G1C5 | 3.00 | 3.01 | 3.00 | 1.84 | 0.29 | 0.08 | 0.08 | 0.06 |
| 152G2F7 | 2.97 | 2.89 | 1.56 | 0.26 | 0.08 | 0.06 | 0.07 | 0.06 |
| 96F8C6 | 2.97 | 3.00 | 2.99 | 1.86 | 0.31 | 0.09 | 0.08 | 0.06 |
| IgG control | 0.18 | 0.07 | 0.06 | 0.06 | 0.07 | 0.06 | 0.06 | 0.06 |

TABLE 21

Binding activities of fully human anti-PCSK9 mAbs to Cyno Monkey PCSK9, as measured by ELISA

| | $OD_{450\ nm}$ Antibody concentration (nM) | | | | | | | |
|---|---|---|---|---|---|---|---|---|
| Clone ID | 66.67 | 6.67 | 0.67 | 0.067 | 0.0067 | 0.00067 | 0.000067 | 0 |
| 103C11E8 | 2.97 | 2.96 | 2.81 | 1.15 | 0.29 | 0.21 | 0.11 | 0.07 |
| IgG control | 0.81 | 0.15 | 0.08 | 0.06 | 0.07 | 0.07 | 0.07 | 0.07 |

Receptor ligand binding assays confirmed that fully human anti-PCSK9 antibodies, generated by conversion of the chimeric anti-PCSK9 antibodies, are able to block the binding of PCSK9 to LDLR. The results, shown in FIGS. 12-13 and 20-21, and in Tables 22-25, indicated that the fully human anti-PCSK9 antibodies can block the binding of PCSK9 and PCSK9$^{D374Y}$ to LDLR. The IgG control was human IgG.

TABLE 22

Inhibition of binding of human PCSK9 to LDLR by fully human anti-PCSK9 mAbs, as measured by ELISA

| | $OD_{450\ nm}$ Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 74C10A8 | 1.41 | 1.43 | 1.76 | 2.19 | 2.32 | 2.28 | 2.31 | 2.40 |
| 76A1B11 | 1.27 | 1.35 | 16.1 | 2.19 | 2.31 | 2.28 | 2.26 | 2.38 |
| 139G1C5 | 1.29 | 1.35 | 1.57 | 2.16 | 2.28 | 2.31 | 2.33 | 2.31 |
| 152G2F7 | 1.32 | 1.31 | 1.86 | 2.19 | 2.31 | 2.25 | 2.27 | 2.29 |
| 96F8C6 | 2.40 | 2.38 | 2.38 | 2.40 | 2.45 | 2.43 | 2.38 | 2.40 |
| IgG control | 1.41 | 1.43 | 1.76 | 2.19 | 2.32 | 2.28 | 2.31 | 2.40 |

TABLE 23

Inhibition of binding of human PCSK9 to LDLR by fully human anti-PCSK9 mAbs, as measured by ELISA

| | $OD_{450\ nm}$ Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 103C11E8 | 1.05 | 1.17 | 1.59 | 2.39 | 2.58 | 2.56 | 2.56 | 2.59 |
| IgG control | 1.96 | 2.03 | 2.03 | 2.23 | 2.21 | 2.17 | 2.27 | 2.04 |

TABLE 24

Inhibition of binding of human PCSK9$^{D374Y}$ to LDLR by fully human anti-PCSK9 mAbs, as measured by ELISA

| | $OD_{450\ nm}$ Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 74C10A8 | 0.26 | 0.41 | 0.91 | 1.69 | 2.34 | 2.20 | 2.15 | 2.08 |
| 76A1B11 | 0.29 | 0.32 | 0.59 | 1.30 | 1.92 | 2.07 | 2.09 | 2.04 |
| 139G1C5 | 0.22 | 0.24 | 0.28 | 0.41 | 1.17 | 1.91 | 2.06 | 2.01 |

TABLE 24-continued

Inhibition of binding of human PCSK9$^{D374Y}$ to LDLR by fully human anti-PCSK9 mAbs, as measured by ELISA

| | OD$_{450\,nm}$ Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 152G2F7 | 0.25 | 0.43 | 1.00 | 1.69 | 1.96 | 2.10 | 2.01 | 1.97 |
| 96F8C6 | 0.23 | 0.21 | 0.33 | 0.71 | 1.58 | 2.09 | 2.02 | 2.01 |
| IgG control | 1.92 | 2.11 | 2.15 | 2.14 | 2.17 | 2.16 | 2.17 | 2.05 |

TABLE 25

Inhibition of binding of human PCSK9$^{D374Y}$ to LDLR by fully human anti-PCSK9 mAbs, as measured by ELISA

| | OD$_{450\,nm}$ Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 103C11E8 | 0.28 | 0.30 | 0.41 | 0.89 | 1.61 | 1.90 | 1.92 | 1.98 |
| IgG control | 1.55 | 1.34 | 1.80 | 1.61 | 1.95 | 1.57 | 1.67 | 1.96 |

Fully human anti-PCSK9 antibodies, generated by conversion of the chimeric anti-PCSK9 antibodies, are able to inhibit PCSK9$^{D374Y}$-mediated reduction of LDL uptake. The results, shown in FIGS. 14-16 and 22, and in Tables 26-27, indicated that fully human anti-PCSK9 antibodies blocked PCSK9$^{D374Y}$-mediated inhibition in LDL uptake in a dose-dependent manner. The IgG control was human IgG.

TABLE 26

Effect of fully human anti-PCSK9 mAbs on human PCSK9$^{D374Y}$-mediated inhibition of LDL uptake

| | LDL (%) Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 76A1B10 | 107.37 | 105.40 | 79.84 | 35.36 | 29.56 | 28.76 | 27.34 | 24.43 |
| IgG control | 25.96 | 26.50 | 26.55 | 29.28 | 28.78 | 25.73 | 24.43 | 24.43 |
| 139G1C5 | 89.56 | 84.96 | 73.34 | 25.86 | 15.84 | 15.50 | 13.83 | 15.74 |
| IgG control | 12.77 | 14.35 | 14.67 | 15.38 | 15.37 | 16.03 | 15.74 | 15.74 |
| 96F8C6 | 114.01 | 114.53 | 75.41 | 38.21 | 33.12 | 31.85 | 32.37 | 31.30 |
| IgG control | 32.26 | 32.55 | 34.70 | 28.71 | 28.89 | 30.55 | 25.64 | 31.30 |

TABLE 27

Effect of fully human anti-PCSK9 mAbs on human PCSK9$^{D374Y}$-mediated inhibition of LDL uptake

| | LDL (%) Antibody concentration (nM) | | | | | | | |
|---|---|---|---|---|---|---|---|---|
| Clone ID | 200 | 40 | 8 | 1.6 | 0.32 | 0.06 | 0.01 | 0 |
| 103C11E8 | 77.83 | 78.75 | 67.70 | 43.82 | 29.49 | 27.90 | 25.89 | 25.97 |
| IgG control | 26.72 | 26.17 | 31.97 | 25.85 | 23.85 | 27.27 | 27.57 | 25.97 |

Example 9—Determination of Binding and Dissociation Constants by Octed Red 96

Dissociation constants were determined by Octed red 96 (Fortiebio). The detailed operation and methods were followed according to the specifications of the instrument provided by the manufacturer. Briefly, an AHC sensor (Anti-human Fc sensor, Fortiebio) was used for the affinity determination. The anti-PCSK9 antibody was diluted to 10 ug/mL in PBS buffer (pH7.4) containing 0.1% (w/w) BSA and 0.02% (v/v) Tween 20 and incubated with the AHC sensor. Five different concentrations of recombinant hPCSK9-His (two-fold serially diluted from a starting concentration of 100 nM or 400 nM) were incubated with the antibody-loaded AHC sensor at 30° C. for 3 minutes. The reaction mixture was further incubated in PBS buffer (pH7.4) containing 0.1% (v/w) BSA and 0.02% (v/v) Tween 20 at 30° C. for 5 minutes. The association and dissociation signals of anti-PCSK9 antibodies to Immunogen A were recorded in real time using Octet Red 96. The affinity, association and dissociation constants were determined using Octet User software, and the results are shown in Table 28.

TABLE 28

Binding kinetics and affinities of fully human anti-PCSK9 mAbs to human PCSK9-His protein, as determined by Octet Red 96

| Clone ID | K$_D$ (nM) | k$_a$ (1/Ms) | k$_d$ (1/s) |
|---|---|---|---|
| 74C10A8 | 14.50 | 1.96 × 10$^5$ | 2.84 × 10$^{-3}$ |
| 76A1B11 | 12.10 | 5.31 × 10$^4$ | 6.43 × 10$^{-4}$ |
| 139G1C5 | 0.63 | 2.54 × 10$^5$ | 1.61 × 10$^{-4}$ |
| 152G2F7 | 2.69 | 1.68 × 10$^5$ | 4.53 × 10$^{-4}$ |
| 96F8C6 | 3.63 | 2.55 × 10$^5$ | 9.25 × 10$^{-4}$ |
| 103C11E8 | 2.17 | 6.95 × 10$^4$ | 1.51 × 10$^{-4}$ |

Example 10—Determination of Binding and Dissociation Constants by Biacore

Anti-human Fc IgG was immobilized on flow cells 1 and 2: HBS-EP+(10 mM HEPES, 150 mM NaCl, 3 mM EDTA, 0.05% P20, pH 7.4) was used as running buffer, and the immobilization of anti-human Fc IgG was carried out using the immobilization wizard template. Flow cells 1 and 2 of a Series S CM5 sensor chip were activated with freshly-mixed 50 mmol/L NHS and 200 mmol/L EDC. 20 ug/mL of anti-human Fc IgG diluted in 10 mM NaAC (pH 4.5) was injected into the activated flow cells 1 and 2. The remaining active coupling sites were blocked with 1M ethanolamine.

Recombinant His-tagged hPCSK9 protein was diluted to 50 nM, followed by four 2-fold serial dilutions with HBS-EP+ buffer. The His-tagged hPCSK9 protein concentrations were 0 nM, 3.125 nM, 6.25 nM, 12.5 nM, 25 nM and 50 nM. K$_D$ measurements were carried out with HBS-EP+ as the running buffer. Each antibody was injected over the CM5 sensor flow cell 2 with a flow rate of 10 uL/min to reach response 230 RU. Prepared His-tagged hPCSK9 protein was then injected over flow cells 1 and 2, at a flow rate of 30 ulmin for 180 sec. Buffer flow was maintained for 400 seconds for dissociation measurements (30 uL/min). To remove the tested antibody from the surface, 10 mM glycine-HCl pH 1.5 was injected for 20 seconds (30 ulJmin). Flow cell 1 was used as reference flow cell. The above steps were repeated for each concentration of serially-diluted His-tagged hPCSK9 protein. The K$_D$ value for each antibody was evaluated using Biacore T200 evaluation software 1.0, and the data was fit with a 1:1 binding model. The results are shown in Table 29.

TABLE 29

Binding kinetics and affinities of fully human anti-PCSK9 mAbs to human PCSK9-His protein, as determined by Biacore

| Clone ID | $K_D$ (M) | $k_a$ (1/Ms) | $k_d$ (1/s) |
|---|---|---|---|
| 74C10A8 | ND | ND | ND |
| 76A1B11 | ND | ND | ND |
| 139G1C5 | 7.09E−11 | 1.71E+05 | 2.40E−05 |
| 152G2F7 | ND | ND | ND |
| 96F8C6 | 2.33E−09 | 9.13E+04 | 3.92E−05 |
| 103C11E8 | 1.42E−09 | 3.82E+04 | 5.41E−05 |
| Alirocumab, Regeneron | 3.94E−10 | 3.18E+04 | 8.06E−05 |
| Evolocumab, Amgen | <1.22E−10 | <1.0E+05 | 8.22E−04 |

Figure 23:
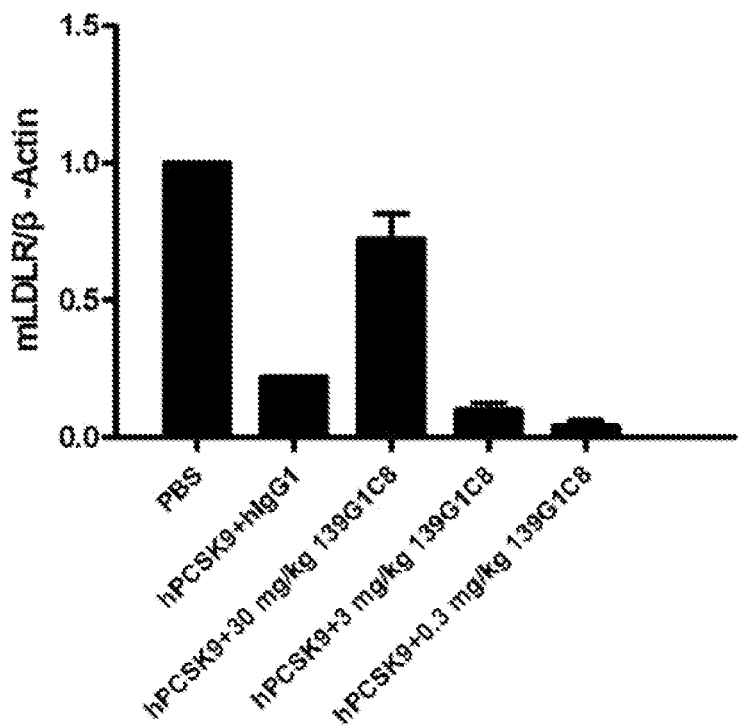
FIGS. 23 A &B show the inhibition of recombinant hPCSK9 protein-mediated LDLR degradation in mice by anti-PCSK9 antibodies according to embodiments of the invention: liver lysates from mice administered with recombinant human PCSK9 protein (hPCSK9) and anti-PCSK9 antibodies, control IgG or vehicle were subject to Western blot analysis using an antibody against mouse LDLR (mLDLR) and an antibody against mouse β-actin (mβ-actin), the ratio of the density of the mLDLR band v.s. the density of the mβ-actin band on the Western Blot was plotted.
Figure 23:
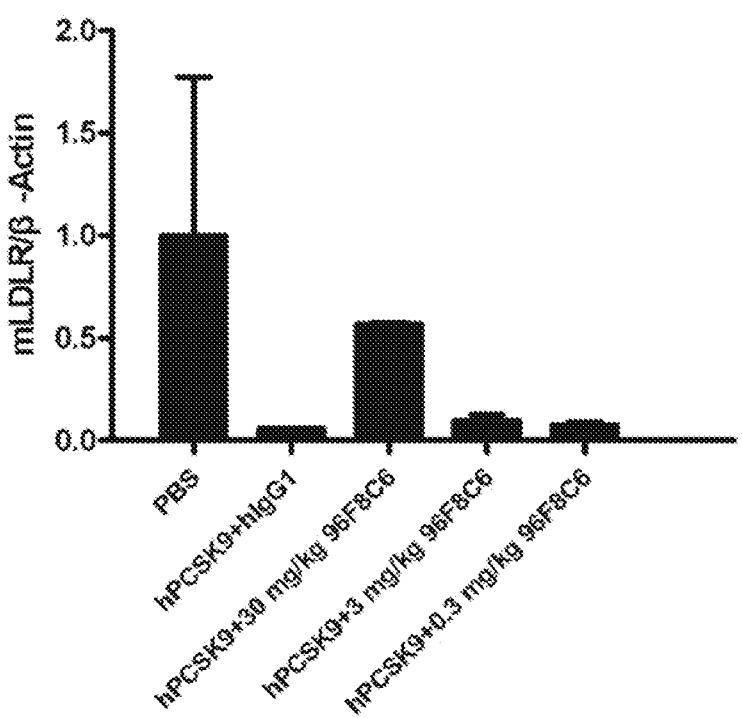

Example 11—Effect of PCSK9 Antibody on PCSK9-Mediated LDLR Degradation 9-10 week old C57BL/6 mice were housed and maintained under SPF conditions. Mice were randomized into 5 groups, with 4 mice in each group. At Day −1, mice were intraperitoneally administered 30 mg/kg, 3 mg/kg, or 0.3 mg/kg test anti-PCSK9 antibody (e.g., 139G1C8 or 96F8C6) control IgG or vehicle. The next day, all mice were intravenuously administered recombinant human PCSK9 protein (30 ug/mouse). One hour after injection with PCSK9, the mice were sacrificed and their livers were harvested. Western blot analysis of liver lysates was performed using an antibody against mouse LDLR (mLDLR) and an antibody against mouse β-actin (mβ-actin). The protein bands were quantified using densitometry, and the ratio of mLDLR to mβ-actin is plotted. The results, shown in FIGS. 23 A and B, indicated that the anti-PCSK9 antibodies inhibited PCSK9-mediated LDLR degradation in vivo.

Example 12—Antibody Thermostability, Measured by Differential Scanning Calorimetry (DSC)

Figure 24:
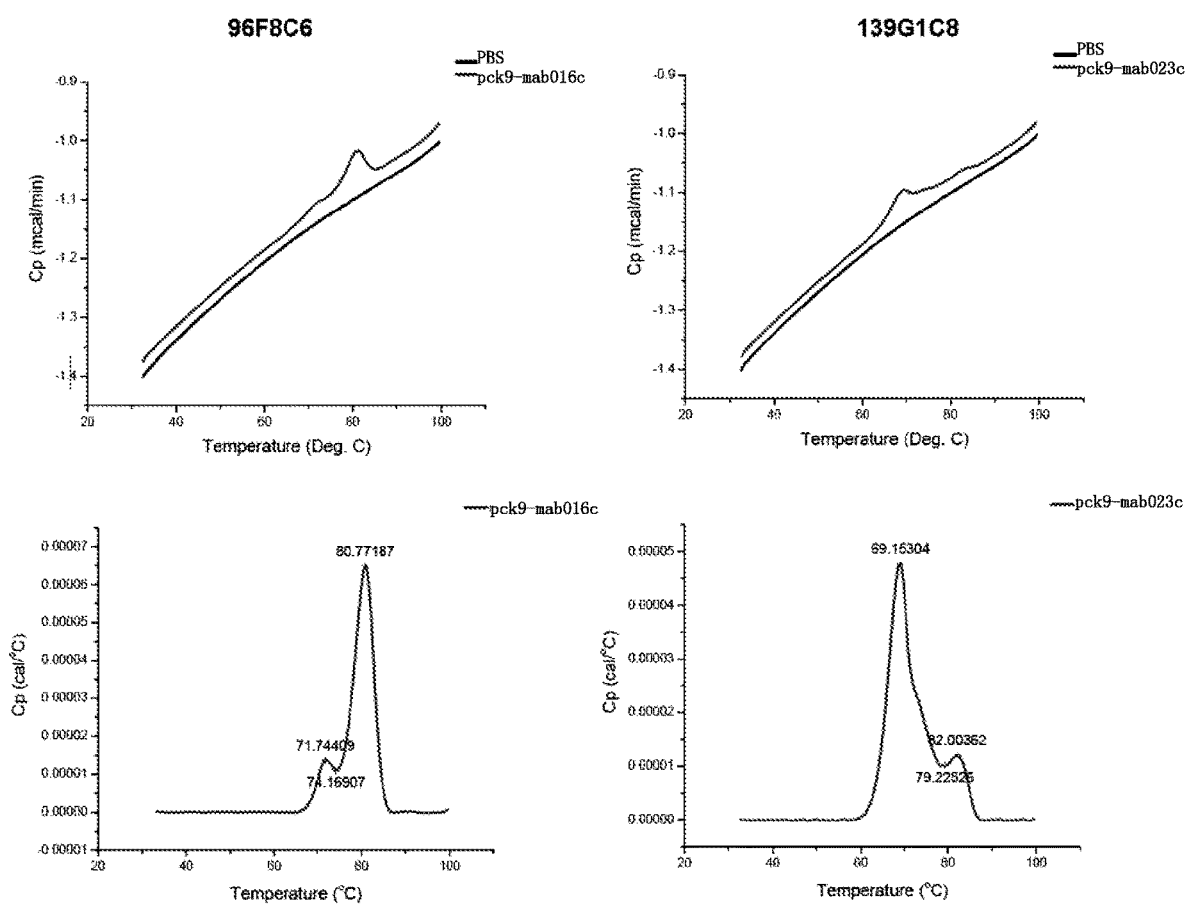
FIG. 24 shows the thermostability of fully human anti-PCSK9 antibodies according to embodiments of the invention, as measured by Differential Scanning Calorimetry (DSC)

Fully human anti-PCSK9 antibodies were adjusted to 1mg/mL and a final volume of about 700 uL with sample buffer. The parameters were set up as follows (VP-DSC): Starting Temperature 30° C.; Final Temperature 100° C.; Scan rate 50° C./hour, Number of Rescans 0; PreScan Thermostat 3 min; PostScan Thermostat 0 min; Post Cycle Thermostat 25° C.; Filtering Period 25 seconds; Feedback Mode/Gain None; Cell Refill Parameters 35° C. The resulting protein-buffer thermograms were processed by subtracting a corresponding buffer-buffer scan and subsequently fitting a baseline to the trace. The Tins were recorded at each peak maxima observed in the thermograms using Origin™ 7.0 software. The results are shown in FIG. 24.

Example 13—Antibody Freeze/Thaw Stability

Figure 25:
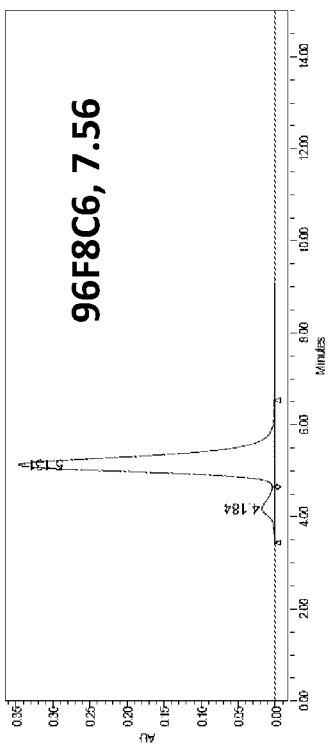
FIG. 25 shows the freeze/thaw stability of fully human anti-PCSK9 antibodies according to embodiments of the invention.
Figure 25:
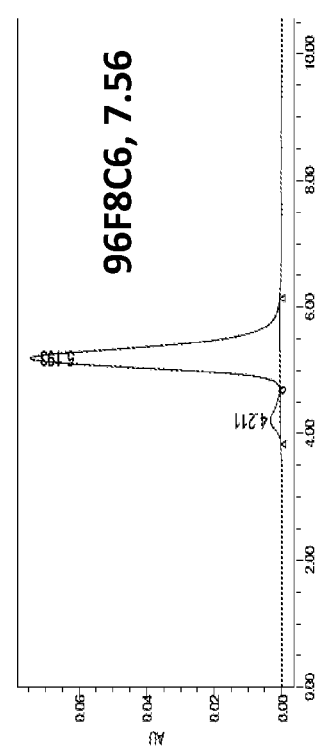
Figure 25:
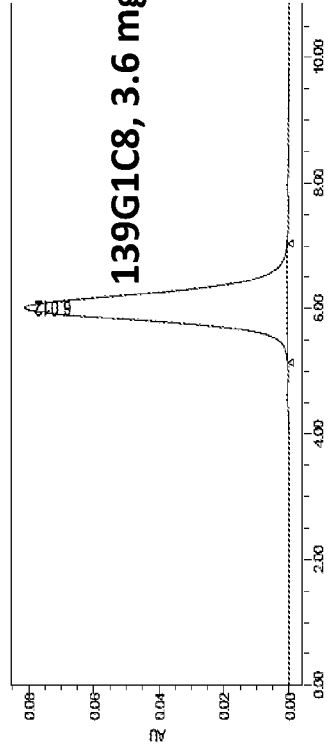

The freeze/thaw stabilities of the fully human anti-PCSK9 antibodies were characterized as follows. A 100 uL aliquot from the frozen stocks of each anti-PCSK9 antibody was thawed at room temperature. Once fully thawed, the samples were then rapidly frozen in the −80° C. freezer and kept at −80° C. for at least two hours before being thawed again at room temperature. The samples went through three identical freeze/thaw cycles. Visual inspection was used to check for precipitation. 20 uL aliquots were removed from the samples for size-exclusion chromatography (SEC) analysis after three freeze/thaw cycles. The stability of the fully human anti-PCSK9 antibodies before and after the freeze/thaw cycles were analyzed by HPLC-SEC characterization. The results, shown in FIG. 25, demonstrated that after three freeze/thaw cycles, monomer IgGs accounted for more than 95% of each of the anti-PCSK9 antibodies tested.

Example 14—Antibody Solubility

Figure 26:
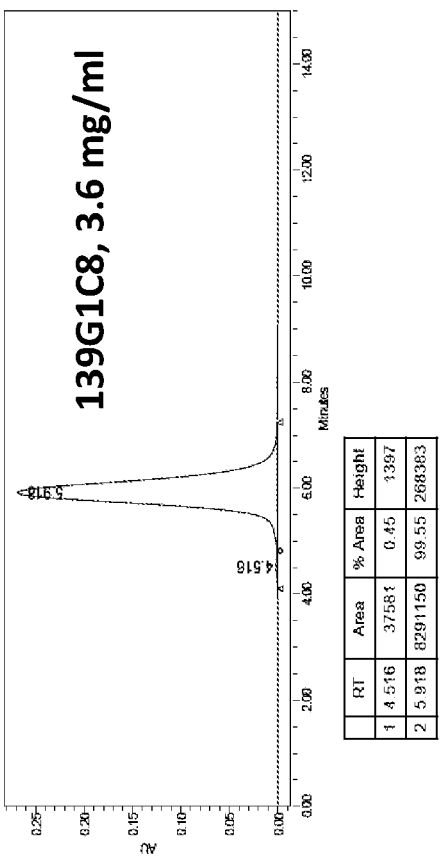
FIG. 26 shows the solubility of fully human anti-PCSK9 antibodies according to embodiments of the invention.
Figure 26:
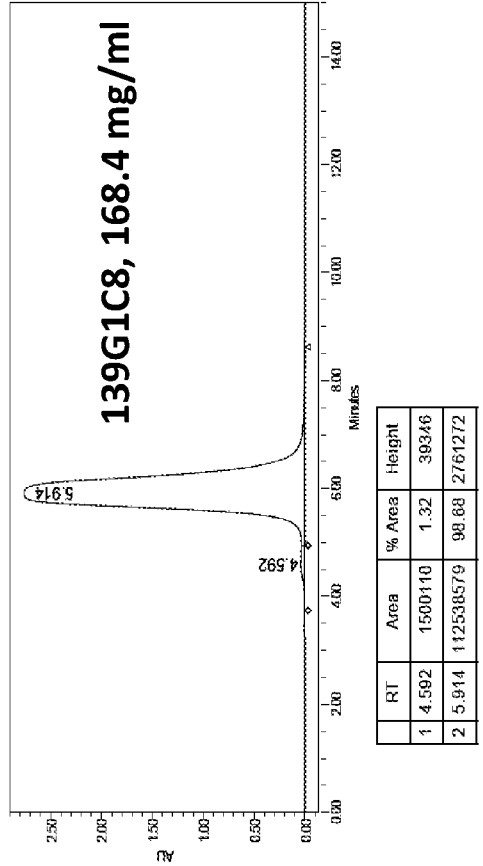
Figure 26:
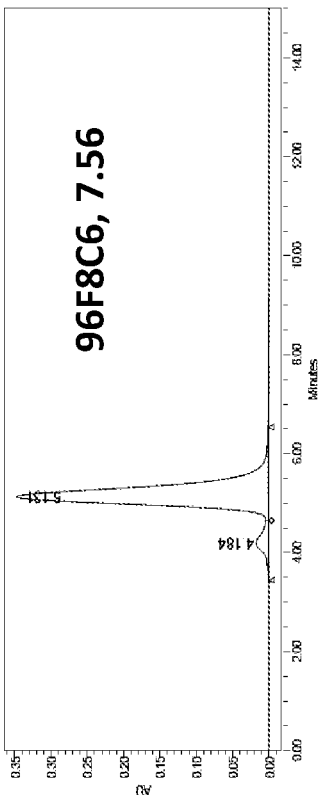
Figure 26:
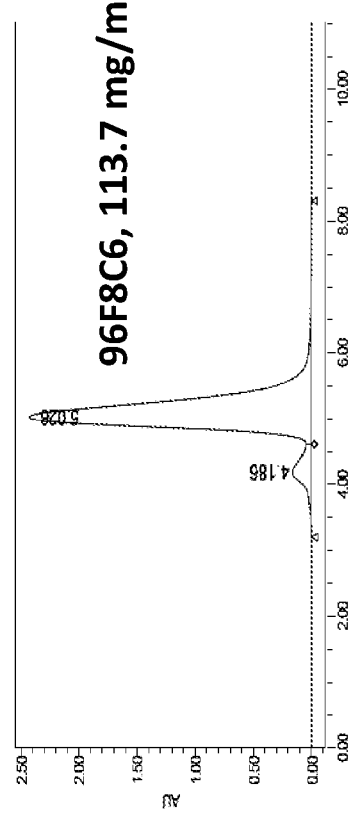

The solubility of the fully human anti-PCSK9 antibodies was characterized by concentrating 10 mg IgG using centrifugal filters (Amicon Ultra-0.5 mL 30K) at 14000 g at 4° C. down to >100 mg/mL. 2 mL or more of IgG was added into the centrifugal filters and concentrated at 14000 g at 4° C. The setting time of centrifuging was 2 min, 3 min, 5 min, 8 min, 15 min, and 20 min, and each time 20 uL were aliquoted to a collection tube to measure the concentration with a nanodrop at A280. The centrifugation was finished when the concentration reached 100 mg/mL. For HPLC-SEC characterization, 6 uL of concentrated samples were injected into an HPLC-SEC column, and the percentages of monomers and aggregates were determined based on the peak area. The results, shown in FIG. 26, demonstrated that all of the fully human anti-PCSK9 antibodies tested had a solubility over 100 mg/mL and that monomer IgGs were higher than 95% for all of the anti-PCSK9 antibodies tested.

Example 15—Affinity Maturation of Anti-PCSK9 Antibodies (Step 1) CDR Mutagenesis Library Construction and Validation 1. Construction of phagemid expression vector and verification of scFv display: Sequences of the 98F8C6 anti-PCSK9 antibody heavy and light chain variable regions were obtained according to the methods of Example 6. Nucleic acids encoding the heavy chain variable region, linker and light chain variable region were assembled using overlapping PCR to generate an scFv. The PCR product was ligated into a phagemid vector, which was then transformed into TG1 cells. Positive clones from ampicillin selection plates were selected, and their phagemid expression vectors were recovered and sequenced.

2. Design of CDR mutagenesis libraries: CDR positions were defined by Kabat numbering. In a typical antibody structure, the HCDR3 and LCDR3 domains provide the core interface for antigen recognition and are surrounded by other CDRs. Therefore, in the absence of structural information regarding which of the CRDs of the anti-PCSK9 antibodies contribute to antigen binding, HCDR3 and LCDR3 were initially targeted for library generation. Amino acid residues on the CDR3 loop were randomized using NNK primers (N=any nucleotide, K=G,T). The mutation rate of each position was kept at 50% to control the number of mutations in each variant and therefore maximally retain the original binding epitope. Long CDRs (>10 amino acids) were separated into two or three overlapping segments. Due to the size of the HCDR3 of clone 96F8C6, it was separated into two overlapping segments, CDR-H3-1 and CDR-H3-2, and each segment was mutated in a separate random library. The primers for CDR mutagenesis were as follows:

(CDRH3-1_mut-F)

SEQ ID NO: 70
gtgtattactgtgcgaga(NNKNNKNNKNNKNNKNNKNNKNNKNNKNNK
NK)tataactactactac -continued (CDRH3-2_mut-F)
SEQ ID NO: 71
attactatggttcggggagt(NNKNNKNNKNNKNNKNNKNNKNNKNNKNN
K)tggggccaagggaccacg (CDRL3_mut-F)
SEQ ID NO: 72
attttgcaacttattactgc(NNKNNKNNKNNKNNKNNKNNKNNKNNK)
tttggccaggggaccaagc 3. Library construction: Random mutagenesis libraries were constructed using overlapping PCR. PCR products were digested using the restriction enzyme SfiI for 2 hours at 50° C. and were then ligated into an SfiI-digested phagemid using T4 ligase at 16° C. overnight Each library was electro-transformed into TG1 *E. coli*.

4. Library validation: The size of each library was between $10^8$ and $10^9$ clones. 50 clones were sequenced for each library, and sequence alignments with the wild type sequence were used to evaluate the quality of the mutation libraries, such as assessment of the mutation positions and the mutation rates.

5. Library packaging and titration: After the amplification of the bacteria libraries, helper phage was added to package phage particles for the following panning steps. The titers of the purified phage libraries were measured by counting newly-infected TG1 clones.

(Step 2) Affinity-Driven Library Panning

The CDR mutagenesis ScFv phage libraries were panned using biotinylated soluble hPCSK9 as antigen in solution phase, under equilibrium conditions. The centrifuge tubes and streptavidin-magnetic to be used were first blocked with 2% MPBS (2% milk in PBS) for 2 hours at room temperature. The libraries were pre-depleted with the beads in 2% MPBS and then mixed with biotin-hPCSK9 in the blocked tubes and incubated on a rotator at room temperature for 2 hours. The concentration of antigen used was 10 nM in the first round of panning, and was reduced 10-fold at a time in the subsequent rounds. The ScFv-antigen-biotin complexes were mixed with streptavidin-beads and incubated for 15 minutes. The beads were collected with a magnet, transferred to 1.5 micro-centrifuge tubes, and washed 5 times each with MPBST (2% milk, 0.5% Tween20 in PBS), PBST (0.5% Tween 20 in PBS), MPBS (2% milk in PBS) and PBS. Bound phage was eluted from the beads with 1mL trypsin (O1 ug/mL in PBS) at 37° C. for 30 minutes. Beads were drawn to one side of the tube using a magnet, and the solution containing eluted phage was transferred to a tube containing 4 mL TG1 (A6000.6) for titration of the panned library.

After each round of panning, the output clones were sequenced to determine the enrichment of mutations. After 3 or 4 rounds of panning, the resulting clones were selected for screening.

(Step 3) ELISA Screening of Affinity-Enhanced Binding Variants

More than 500 single clones were selected after 3 or 4 rounds of panning. IPTG induction was used to induce expression of the ScFv variants, and clones with strong ELISA signal were sent for sequencing.

(Step 4) Eukaryotic Production of Affinity Improved Variants and Affinity Characterization VH and VL sequences from enriched clones were cloned into IgG expression vectors, inserted between leader sequence and constant region accordingly. The resulting vectors were transfected into HEK293 cells by transient transfection. After 5-7 days, the IgGs in the culture supernatant were purified by affinity purification using Protein A column, as described in Example 8. The VH sequences of the affinity-improved variants are listed in Table 30. The light chain sequences of these variants were the same as those of the light chain of antibody 98F8C6, e.g., the LCDR 1-3 of SEQ ID NOs:38-40, respectively, or alight chain variable region of SEQ ID NO:37, or its coding sequence SEQ ID NO:58.

TABLE 30

| VH sequences of affinity-improved human anti-PCSK9 mAb variants ||| 
|---|---|---|
| ID | Heavy chain sequence | Heavy chain CDRH3 sequence |
| AF-mab023_01 | SEQ ID NO: 91<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYG<br>IGSYNYYYYGMDVWGQGTTVTSS | SEQ ID NO: 73<br>DRGTYYYGIGSYNY<br>YYYGMDV |
| AF-mab023_02 | SEQ ID NO: 92<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYY<br>WLGTYNYYYYGMDVWGQGTTVTSS | SEQ ID NO: 74<br>DRGTYYYWLGTYN<br>YYYYGMDV |
| AF-mab023_03 | SEQ ID NO: 93<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYA<br>SGSYNYYYYGMDVWGQGTTVTSS | SEQ ID NO: 75<br>DRGTYYYASGSYNY<br>YYYGMDV |
| AF-mab023_04 | SEQ ID NO: 94<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYD<br>SGGYNYYYYGMDVWGQGTTVTSS | SEQ ID NO: 76<br>DRGTYYYDSGGYN<br>YYYYGMDV |

TABLE 30-continued

VH sequences of affinity-improved human anti-PCSK9 mAb variants

| ID | Heavy chain sequence | Heavy chain CDRH3 sequence |
|---|---|---|
| AF-mab023_05 | SEQ ID NO: 95<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYH<br>WLGSYNYYYYGMDVWGQGTTVTVSS | SEQ ID NO: 77<br>DRGTYYHWLGSYN<br>YYYYGMDV |
| AF-mab023_06 | SEQ ID NO: 96<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYFQ<br>SGSYNYYYYGMDVWGQGTTVTVSS | SEQ ID NO: 78<br>DRGTYYFQSGSYNY<br>YYYGMDV |
| AF-mab023_07 | SEQ ID NO: 97<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYQ<br>QGSYNYYYYGMDVWGQGTTVTVSS | SEQ ID NO: 79<br>DRGTYYYQQGSYN<br>YYYYGMDV |
| AF-mab023_08 | SEQ ID NO: 98<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYIA<br>DGSYNYYYYGMDVWGQGTTVTVSS | SEQ ID NO: 80<br>DRGTYYIADGSYNY<br>YYYGMDV |
| AF-mab023_10 | SEQ ID NO: 99<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYD<br>SGRYNYYYYGMDVWGQGTTVTVSS | SEQ ID NO: 81<br>DRGTYYYDSGRYN<br>YYYYGMDV |
| AF-mab023_11 | SEQ ID NO: 100<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYQ<br>EGSYNYYYYGMDVWGQGTTVTVSS | SEQ ID NO: 82<br>DRGTYYYQEGSYN<br>YYYYGMDV |
| AF-mab023_12 | SEQ ID NO: 101<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYT<br>EGGYNYYYYGMDVWGQGTTVTVSS | SEQ ID NO: 83<br>DRGTYYYIEGGYN<br>YYYYGMDV |
| AF-mab023_13 | SEQ ID NO: 102<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYT<br>EGSYNYYYYGMDVWGQGTTVTVSS | SEQ ID NO: 84<br>DRGTYYYIEGSYNY<br>YYYGMDV |
| AF-mab023_14 | SEQ ID NO: 103<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYA<br>DGGYNYYYYGMDVWGQGTTVTVSS | SEQ ID NO: 85<br>DRGTYYYADGGYN<br>YYYYGMDV |
| AF-mab023_15 | SEQ ID NO: 104<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYQ<br>DGNYNYYYYGMDVWGQGTTVTVSS | SEQ ID NO: 86<br>DRGTYYYQDGNYN<br>YYYYGMDV |
| AF-mab023_16 | SEQ ID NO: 105<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYQ<br>DGKYNYYYYGMDVWGQGTTVTVSS | SEQ ID NO: 87<br>DRGTYYYQDGKYN<br>YYYYGMDV |
| AF-mab023_17 | SEQ ID NO: 106<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYTG<br>MGEYNYYYYGMDVWGQGTTVTVSS | SEQ ID NO: 88<br>DRGTYYTGMGEYN<br>YYYYGMDV |

TABLE 30-continued

VH sequences of affinity-improved human anti-PCSK9 mAb variants

| ID | Heavy chain sequence | Heavy chain CDRH3 sequence |
|---|---|---|
| AF-mab023_18 | SEQ ID NO: 107<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYA<br>DGDYNYYYYGMDVWGQGTTVTVSS | SEQ ID NO: 89<br>DRGTYYYADGDYN<br>YYYYGMDV |
| AF-mab023_19 | SEQ ID NO: 108<br>EVQLVESGGGLVQPGGSLRLSCAASGITFSSYWMSW<br>VRQAPGKGLEWVANIKQDGSEKYYVDSVKGRFTIS<br>RDIAKNSLYLQMNSLRAEDTAVYYCARDRGTYYYA<br>SGKYNYYYYGMDVWGQGTTVTVSS | SEQ ID NO: 90<br>DRGTYYYASGKYN<br>YYYYGMDV |

Figure 27A:
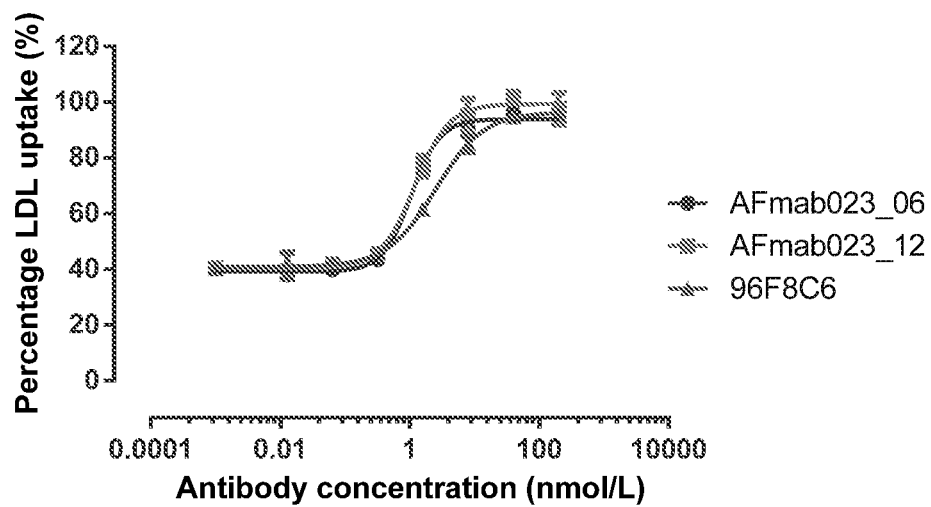
FIGS. 27 A&B show the inhibition of PCSK9$^{D374Y}$-induced LDL uptake in HepG2 cells by various human anti-PCSK9 antibodies according to embodiments of the invention having improved affinity according to embodiments of the invention.
Figure 27B:
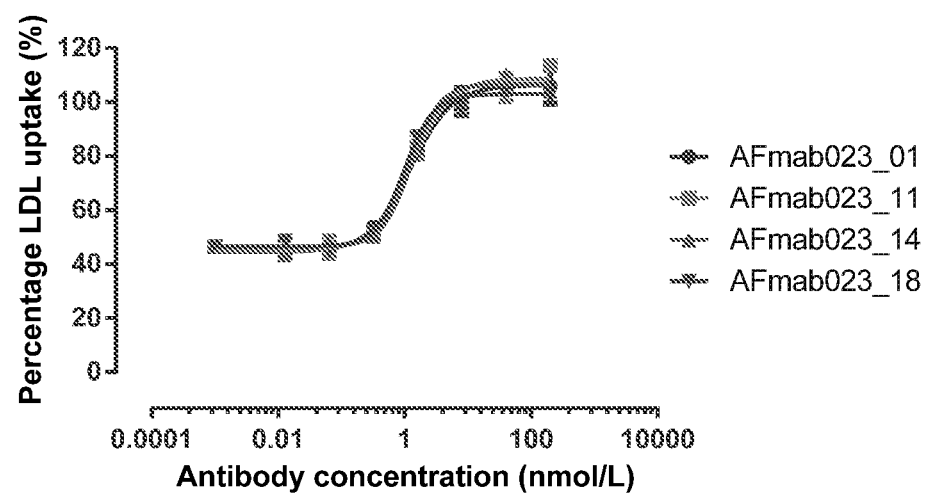

The final dissociation constant ($K_D$) of the affinity-enhanced antibodies against human PCSK9 were measured by Biacore as described in Example 10, and the data are shown in Table 31. The effect of the affinity-enhanced antibodies on recombinant PCSK9$^{D374Y}$-induced LDL uptake was determined, and the results are shown in FIGS. 27 A and B, and in Table 32.

TABLE 31

Binding kinetics and affinities of affinity-enhanced human anti-PCSK9 mAbs to human PCSK9-His protein, as determined by Biacore

| Clone ID | ka (1/M) | kd (1/s) | $K_D$ (M) |
|---|---|---|---|
| AF-mab023_01 | 3.20E+05 | 1.15E−04 | 3.6E−10 |
| AF-mab023_02 | 3.06E+05 | 8.20E−05 | 2.68E−10 |
| AF-mab023_03 | 3.70E+05 | 4.60E−04 | 1.24E−09 |
| AF-mab023_04 | 5.84E+05 | 2.39E−04 | 4.09E−10 |
| AF-mab023_05 | 3.05E+05 | 6.31E−05 | 2.07E−10 |
| AF-mab023_06 | 2.93E+05 | 6.59E−05 | 2.25E−10 |
| AF-mab023_07 | 3.27E+05 | 2.14E−04 | 6.53E−10 |
| AF-mab023_08 | 3.57E+05 | 1.58E−04 | 4.43E−10 |
| AF-mab023_10 | 3.13E+05 | 3.28E−04 | 1.05E−09 |
| AF-mab023_11 | 5.53E+05 | 1.44E−04 | 2.6E−10 |
| AF-mab023_12 | 4.80E+05 | 8.47E−05 | 1.76E−10 |
| AF-mab023_13 | 4.55E+05 | 1.78E−04 | 3.92E−10 |
| AF-mab023_14 | 5.34E+05 | 1.64E−04 | 3.06E−10 |
| AF-mab023_15 | 4.77E+05 | 1.82E−04 | 3.81E−10 |
| AF-mab023_16 | 3.19E+05 | 1.43E−04 | 4.47E−10 |
| AF-mab023_17 | 3.51E+05 | 1.09E−04 | 3.1E−10 |
| AF-mab023_18 | 5.51E+05 | 1.61E−04 | 2.92E−10 |
| AF-mab023_19 | 2.26E+05 | 3.51E−04 | 1.55E−09 |

TABLE 32

Effect of affinity-enhanced human anti-PCSK9 mAbson human PCSK9$^{D374Y}$-mediated inhibition of LDL uptake

| Clone ID | IC50 (nM) |
|---|---|
| 96F8C6 | 2.51 |
| AF-mab023_01 | 1.20 |
| AF-mab023_06 | 1.05 |
| AF-mab023_11 | 1.28 |
| AF-mab023_12 | 1.21 |
| AF-mab023_14 | 1.25 |
| AF-mab023_18 | 0.99 |

While the invention has been described in detail, and with reference to specific embodiments thereof, it will be apparent to one of ordinary skill in the art that various changes and modifications can be made therein without departing from the spirit and scope of the invention.

REFERENCES

Mozaffarian et al., 2015, Circulation. 131(4):e29-322
Gencer et al., 2015, Swiss Med Wkly. 145:w14094
Harding and Lonberg, 1995, Ann. N.Y. Acad. Sci. 764:536-546
Kabat, 1991, "Sequences of proteins of objective interest," the NIH, Bethesda, Md.
Lonberg and Huszar, 1995, Internal Rev. Immunol. 13:65-93
Lonberg et al., 1994, Nature 368: 856-859
Rallidis and Lekakis, 2016, Hellenic J Cardiol. 57(2):86-91
Sambrook and Russell, 1989, Molecular cloning: a laboratory manual, New York: Cold Spring Harbor Laboratory Press, 2nd ed

We claim:

1. An isolated monoclonal antibody or antigen-binding fragment thereof comprising:

(1) an LCDR1 having the polypeptide sequence of SEQ ID NO: 38;
   (2) an LCDR2 having the polypeptide sequence of SEQ ID NO: 39;
   (3) an LCDR3 having the polypeptide sequence of SEQ ID NO: 40;
   (4) an HCDR1 having the polypeptide sequence of SEQ ID NO: 34;
   (5) an HCDR1 having the polypeptide sequence of SEQ ID NO: 35; and
   (6) an HCDR3 having the polypeptide sequence of SEQ ID NO: 36;
   wherein the antibody or antigen-binding fragment thereof binds PCSK9.

2. The isolated monoclonal antibody or antigen-binding fragment of claim 1, comprising a heavy chain variable region having a polypeptide sequence at least 95% identical to SEQ ID NO: 33, and a light chain variable region having a polypeptide sequence at least 95% identical to SEQ ID NO: 37, respectively.

3. The isolated monoclonal antibody or antigen-binding fragment of claim 1, comprising:

a heavy chain variable region having the polypeptide sequence of SEQ ID NO: 33, and a light chain variable region having the polypeptide sequence of SEQ ID NO: 37.

4. The isolated monoclonal antibody or antigen-binding fragment of claim 1, wherein the antibody or antigen-binding fragment thereof is chimeric.

5. The isolated monoclonal antibody or antigen-binding fragment of claim 1, wherein the antibody or antigen-binding fragment thereof is human.

6. The isolated monoclonal antibody or antigen-binding fragment of claim 5, comprising a human heavy chain IgG1 constant region, and a human antibody light chain kappa constant region.

7. An isolated nucleic acid encoding the monoclonal antibody or antigen-binding fragment of claim 1.

8. A vector comprising the isolated nucleic acid of claim 7.

9. A host cell comprising the nucleic acid of claim 7.

10. A pharmaceutical composition, comprising the isolated monoclonal antibody or antigen-binding fragment of claim 1 and a pharmaceutically acceptable carrier.

11. A method of blocking binding of PCSK9 to LDLR, or augmenting uptake of LDL in a subject in need thereof, comprising administering to the subject the pharmaceutical composition of claim 10.

12. A method of treating a lipid disease, disorder or condition, a metabolic disease, disorder or condition, an inflammatory disease, disorder or condition, or an infectious disease, disorder or condition in a subject in need thereof, comprising administering to the subject the pharmaceutical composition of claim 10.

13. A method of treating a lipid disorder, metabolic disease or inflammatory disease in a subject in need thereof, comprising administering to the subject the pharmaceutical composition of claim 10, wherein the lipid disorder, metabolic disease or inflammatory disease is selected from the group consisting of hyperlipidemia, primary hyperlipidemia, dyslipidemia, mixed dyslipidemia, homozygous familial hypercholesterolemia, and sepsis.

14. A method of producing the monoclonal antibody or antigen-binding fragment of claim 1, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or cell culture.

15. A method of producing a pharmaceutical composition comprising the monoclonal antibody or antigen-binding fragment of claim 1, comprising combining the monoclonal antibody or antigen-binding fragment with a pharmaceutically acceptable carrier to obtain the pharmaceutical composition.

* * * * *

SEQUENCE LISTING

<160> NUMBER OF SEQ ID NOS: 108

<210> SEQ ID NO 1
<211> LENGTH: 128
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Asn Thr Tyr
            20                  25                  30

Tyr Trp Ser Trp Ile Arg Gln Pro Pro Gly Lys Gly Leu Glu Trp Ile

```
                35                  40                  45
Gly Tyr Ile Tyr Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Thr Ser Val Thr Ala Ala Asp Thr Ala Val Tyr Tyr Cys Ala
                 85                  90                  95

Arg Glu Arg Phe Thr Met Val Arg Gly Val Met Met Asp Tyr Tyr Tyr
            100                 105                 110

Tyr Gly Met Asp Val Trp Gly Gln Gly Thr Thr Val Thr Val Ser Ser
        115                 120                 125

<210> SEQ ID NO 2
<211> LENGTH: 10
<212> TYPE: PRT
<213> ORGANISM: Homo sapiens

<400> SEQUENCE: 2

Gly Gly Ser Ile Asn Thr Tyr Tyr Trp Ser
1               5                   10

<210> SEQ ID NO 3
<211> LENGTH: 16
<212> TYPE: PRT
<213> ORGANISM: Homo sapiens

<400> SEQUENCE: 3

Tyr Ile Tyr Tyr Ser Gly Ser Thr Asn Tyr Asn Pro Ser Leu Lys Ser
1               5                   10                  15

<210> SEQ ID NO 4
<211> LENGTH: 21
<212> TYPE: PRT
<213> ORGANISM: Homo sapiens

<400> SEQUENCE: 4

Arg Glu Arg Phe Thr Met Val Arg Gly Val Met Met Asp Tyr Tyr Tyr
1               5                   10                  15

Tyr Gly Met Asp Val
            20

<210> SEQ ID NO 5
<211> LENGTH: 107
<212> TYPE: PRT
<213> ORGANISM: Homo sapiens

<400> SEQUENCE: 5

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Arg
                 85                  90                  95
```

```
Thr Phe Gly Gln Gly Thr Lys Val Glu Ile Lys
            100                 105

<210> SEQ ID NO 6
<211> LENGTH: 11
<212> TYPE: PRT
<213> ORGANISM: Homo sapiens

<400> SEQUENCE: 6

Arg Ala Ser Gln Gly Ile Ser Ser Tyr Leu Ala
1               5                   10

<210> SEQ ID NO 7
<211> LENGTH: 7
<212> TYPE: PRT
<213> ORGANISM: Homo sapiens

<400> SEQUENCE: 7

Ala Ala Ser Thr Leu Gln Ser
1               5

<210> SEQ ID NO 8
<211> LENGTH: 9
<212> TYPE: PRT
<213> ORGANISM: Homo sapiens

<400> SEQUENCE: 8

Gln Gln Leu Asn Ser Tyr Pro Arg Thr
1               5

<210> SEQ ID NO 9
<211> LENGTH: 125
<212> TYPE: PRT
<213> ORGANISM: Homo sapiens

<400> SEQUENCE: 9

Gln Val Gln Leu Val Glu Ser Gly Gly Val Val Gln Pro Gly Arg
1               5                   10                  15

Ser Leu Arg Leu Ser Cys Ala Ala Thr Gly Phe Thr Phe Ser Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Val Ser Asp Tyr Phe Gly Ser Gly Asn Ser Tyr Tyr Tyr Gly Met
            100                 105                 110

Asp Val Trp Gly Gln Gly Thr Thr Val Thr Val Ser Ser
        115                 120                 125

<210> SEQ ID NO 10
<211> LENGTH: 10
<212> TYPE: PRT
<213> ORGANISM: Homo sapiens

<400> SEQUENCE: 10

Gly Phe Thr Phe Ser Ile Tyr Gly Met His
1               5                   10
```

<210> SEQ ID NO 11
<211> LENGTH: 17
<212> TYPE: PRT
<213> ORGANISM: Homo sapiens

<400> SEQUENCE: 11

Val Ile Trp Tyr Asp Gly Ser Asn Lys Tyr Tyr Ala Asp Ser Val Lys
1               5                   10                  15

Gly

<210> SEQ ID NO 12
<211> LENGTH: 17
<212> TYPE: PRT
<213> ORGANISM: Homo sapiens

<400> SEQUENCE: 12

Ser Asp Tyr Phe Gly Ser Gly Asn Ser Tyr Tyr Tyr Gly Met Asp
1               5                   10                  15

Val

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ser Asn Tyr
            20                  25                  30

Leu Ala Trp Tyr Gln Gln Lys Pro Gly Lys Val Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Ala Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 14
<211> LENGTH: 11
<212> TYPE: PRT
<213> ORGANISM: Homo sapiens

<400> SEQUENCE: 14

Arg Ala Ser Gln Val Ile Ser Asn Tyr Leu Ala
1               5                   10

<210> SEQ ID NO 15
<211> LENGTH: 7
<212> TYPE: PRT
<213> ORGANISM: Homo sapiens

<400> SEQUENCE: 15

Thr Ala Ser Thr Leu Gln Ser
1               5

<210> SEQ ID NO 16

-continued

```
<211> LENGTH: 9
<212> TYPE: PRT
<213> ORGANISM: Homo sapiens

<400> SEQUENCE: 16

Gln Lys Tyr Asn Ser Ala Pro Tyr Thr
1               5

<210> SEQ ID NO 17
<211> LENGTH: 118
<212> TYPE: PRT
<213> ORGANISM: Homo sapiens

<400> SEQUENCE: 17

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Arg Asn
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Leu Leu Gly Ile Gly Leu Asp Tyr Trp Gly Gln Gly Thr
            100                 105                 110

Leu Val Thr Val Ser Ser
        115

<210> SEQ ID NO 18
<211> LENGTH: 11
<212> TYPE: PRT
<213> ORGANISM: Homo sapiens

<400> SEQUENCE: 18

Gly Gly Ser Ile Ser Arg Asn Asn Trp Trp Ser
1               5                   10

<210> SEQ ID NO 19
<211> LENGTH: 16
<212> TYPE: PRT
<213> ORGANISM: Homo sapiens

<400> SEQUENCE: 19

Glu Ile Tyr His Ser Gly Ser Thr Asn Tyr Asn Pro Ser Leu Lys Ser
1               5                   10                  15

<210> SEQ ID NO 20
<211> LENGTH: 10
<212> TYPE: PRT
<213> ORGANISM: Homo sapiens

<400> SEQUENCE: 20

Arg Asp Leu Leu Gly Ile Gly Leu Asp Tyr
1               5                   10

<210> SEQ ID NO 21
<211> LENGTH: 107
<212> TYPE: PRT
<213> ORGANISM: Homo sapiens
```

<400> SEQUENCE: 21

Glu Phe Val Leu Thr Gln Ser Pro Ala Thr Leu Ser Leu Ser Pro Gly
1               5                   10                  15

Glu Arg Ala Ile Leu Ser Cys Arg Ala Ser Gln Ser Phe Ser Ser Tyr
            20                  25                  30

Ile Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Ser Asn Trp Met Tyr
                85                  90                  95

Thr Phe Gly Gln Gly Thr Lys Leu Glu Ile Lys
            100                 105

<210> SEQ ID NO 22
<211> LENGTH: 11
<212> TYPE: PRT
<213> ORGANISM: Homo sapiens

<400> SEQUENCE: 22

Arg Ala Ser Gln Ser Phe Ser Ser Tyr Ile Ala
1               5                   10

<210> SEQ ID NO 23
<211> LENGTH: 7
<212> TYPE: PRT
<213> ORGANISM: Homo sapiens

<400> SEQUENCE: 23

Asp Ala Ser Asn Arg Ala Thr
1               5

<210> SEQ ID NO 24
<211> LENGTH: 9
<212> TYPE: PRT
<213> ORGANISM: Homo sapiens

<400> SEQUENCE: 24

Gln Gln His Ser Asn Trp Met Tyr Thr
1               5

<210> SEQ ID NO 25
<211> LENGTH: 129
<212> TYPE: PRT
<213> ORGANISM: Homo sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Phe Gly Gly Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

```
Leu His Met Asn Ser Leu Arg Ala Glu Asp Thr Ala Val Tyr Tyr Cys
                85                  90                  95

Ala Arg Asp Arg Thr Thr Met Ile Arg Gly Val Ser Leu Tyr Tyr Tyr
            100                 105                 110

Tyr Tyr Gly Met Asp Val Trp Gly Gln Gly Thr Ala Thr Val Ser
        115                 120                 125
Ser

<210> SEQ ID NO 26
<211> LENGTH: 10
<212> TYPE: PRT
<213> ORGANISM: Homo sapiens

<400> SEQUENCE: 26

Glu Phe Thr Phe Gly Gly Tyr Trp Met Thr
1               5                   10

<210> SEQ ID NO 27
<211> LENGTH: 17
<212> TYPE: PRT
<213> ORGANISM: Homo sapiens

<400> SEQUENCE: 27

Asn Ile Lys Gln Asp Gly Ser Glu Lys Tyr Tyr Val Asp Ser Val Lys
1               5                   10                  15
Gly

<210> SEQ ID NO 28
<211> LENGTH: 21
<212> TYPE: PRT
<213> ORGANISM: Homo sapiens

<400> SEQUENCE: 28

Arg Asp Arg Thr Thr Met Ile Arg Gly Val Ser Leu Tyr Tyr Tyr Tyr
1               5                   10                  15

Tyr Gly Met Asp Val
            20

<210> SEQ ID NO 29
<211> LENGTH: 107
<212> TYPE: PRT
<213> ORGANISM: Homo sapiens

<400> SEQUENCE: 29

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

```
<210> SEQ ID NO 30
<211> LENGTH: 11
<212> TYPE: PRT
<213> ORGANISM: Homo sapiens

<400> SEQUENCE: 30

Arg Ala Ser Gln Ser Val Ser Ser Tyr Leu Ala
1               5                   10

<210> SEQ ID NO 31
<211> LENGTH: 7
<212> TYPE: PRT
<213> ORGANISM: Homo sapiens

<400> SEQUENCE: 31

Asp Ala Ser Asn Arg Ala Thr
1               5

<210> SEQ ID NO 32
<211> LENGTH: 9
<212> TYPE: PRT
<213> ORGANISM: Homo sapiens

<400> SEQUENCE: 32

Gln Gln Arg Ser Asn Trp Pro Leu Thr
1               5

<210> SEQ ID NO 33
<211> LENGTH: 130
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Gly Ser Gly Ser Tyr Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 34
<211> LENGTH: 10
<212> TYPE: PRT
<213> ORGANISM: Homo sapiens

<400> SEQUENCE: 34

Gly Ile Thr Phe Ser Ser Tyr Trp Met Ser
1               5                   10
```

<210> SEQ ID NO 35
<211> LENGTH: 17
<212> TYPE: PRT
<213> ORGANISM: Homo sapiens

<400> SEQUENCE: 35

Asn Ile Lys Gln Asp Gly Ser Glu Lys Tyr Tyr Val Asp Ser Val Lys
1               5                   10                  15

Gly

<210> SEQ ID NO 36
<211> LENGTH: 22
<212> TYPE: PRT
<213> ORGANISM: Homo sapiens

<400> SEQUENCE: 36

Arg Asp Arg Gly Thr Tyr Tyr Tyr Gly Ser Gly Ser Tyr Asn Tyr Tyr
1               5                   10                  15

Tyr Tyr Gly Met Asp Val
            20

<210> SEQ ID NO 37
<211> LENGTH: 107
<212> TYPE: PRT
<213> ORGANISM: Homo sapiens

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 38
<211> LENGTH: 11
<212> TYPE: PRT
<213> ORGANISM: Homo sapiens

<400> SEQUENCE: 38

Arg Ala Ser Gln Ser Ile Ser Ser Trp Leu Ala
1               5                   10

<210> SEQ ID NO 39
<211> LENGTH: 7
<212> TYPE: PRT
<213> ORGANISM: Homo sapiens

<400> SEQUENCE: 39

Lys Ala Ser Ser Leu Glu Ser
1               5

```
<210> SEQ ID NO 40
<211> LENGTH: 9
<212> TYPE: PRT
<213> ORGANISM: Homo sapiens

<400> SEQUENCE: 40

Gln Gln Tyr Asn Ser Tyr Ser Tyr Thr
1               5

<210> SEQ ID NO 41
<211> LENGTH: 121
<212> TYPE: PRT
<213> ORGANISM: Homo sapiens

<400> SEQUENCE: 41

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ile Ala Val Ala Gly Thr Asp Val Met Asp Ala Trp Gly
            100                 105                 110

Gln Gly Ala Ser Val Thr Val Ser Ser
        115                 120

<210> SEQ ID NO 42
<211> LENGTH: 11
<212> TYPE: PRT
<213> ORGANISM: Homo sapiens

<400> SEQUENCE: 42

Gly Gly Ser Ile Ser Ser Ser Asn Trp Trp Ser
1               5                   10

<210> SEQ ID NO 43
<211> LENGTH: 16
<212> TYPE: PRT
<213> ORGANISM: Homo sapiens

<400> SEQUENCE: 43

Glu Ile Tyr His Ser Gly Ser Thr Asn Tyr Asn Pro Ser Leu Lys Ser
1               5                   10                  15

<210> SEQ ID NO 44
<211> LENGTH: 13
<212> TYPE: PRT
<213> ORGANISM: Homo sapiens

<400> SEQUENCE: 44

Arg Gly Ile Ala Val Ala Gly Thr Asp Val Met Asp Ala
1               5                   10

<210> SEQ ID NO 45
<211> LENGTH: 107
<212> TYPE: PRT
```

<213> ORGANISM: Homo sapiens

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Val Trp Tyr Gln Gln Lys Ser Gly Gln Ala Pro Arg Leu Leu Ile
        35                  40                  45

Tyr Gly Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Leu Tyr Tyr Cys Gln Gln Arg Gly Asn Trp Met Tyr
                85                  90                  95

Thr Phe Gly Gln Gly Thr Lys Leu Glu Ile Lys
                100                 105

<210> SEQ ID NO 46
<211> LENGTH: 11
<212> TYPE: PRT
<213> ORGANISM: Homo sapiens

<400> SEQUENCE: 46

Arg Ala Ser Gln Ser Val Ser Ser Tyr Leu Val
1               5                   10

<210> SEQ ID NO 47
<211> LENGTH: 7
<212> TYPE: PRT
<213> ORGANISM: Homo sapiens

<400> SEQUENCE: 47

Gly Thr Ser Asn Arg Ala Thr
1               5

<210> SEQ ID NO 48
<211> LENGTH: 9
<212> TYPE: PRT
<213> ORGANISM: Homo sapiens

<400> SEQUENCE: 48

Gln Gln Arg Gly Asn Trp Met Tyr Thr
1               5

<210> SEQ ID NO 49
<211> LENGTH: 384
<212> TYPE: DNA
<213> ORGANISM: Homo sapiens

<400> SEQUENCE: 49
caggtgcagc tgcaggagtc gggcccagga ctggtgaagc cttcggagac cctgtccctc      60
acctgcagtg tctctggtgg ctccatcaat acttactact ggagctggat ccggcagccc     120
ccagggaagg gactggagtg gattgggtat atctattaca gtgggagcac caactacaac     180
ccctccctca agagtcgagt caccatatca gtagacacgt ccaagaacca gttctccctg     240
aagttgactt ctgtgaccgc tgcggacacg gccgtgtatt actgtgcgag agaaaggttt     300
actatggttc ggggagttat gatgactac tactactacg gtatggacgt ctggggccaa     360
gggaccacgg tcaccgtctc ctca                                            384

<210> SEQ ID NO 50
<211> LENGTH: 375
<212> TYPE: DNA
<213> ORGANISM: Homo sapiens

<400> SEQUENCE: 50

| | | | | | |
|---|---|---|---|---|---|
| caggtgcagt | tggtggagtc | tgggggaggc | gtggtccagc | ctggagggtc | cctgagactc | 60 |
| tcctgtgcag | cgactggatt | caccttcagt | atctatggca | tgcactgggt | ccgccaggct | 120 |
| ccaggcaagg | gactggagtg | ggtggcagtt | atatggtatg | atggaagtaa | taaatactat | 180 |
| gcagactccg | tgaagggccg | attcatcatc | tccagagaca | attccaagaa | tacgttgtat | 240 |
| ctgcaaatga | acagcctgag | agtcgaggac | acggctgttt | attactgtgt | gagcgattac | 300 |
| tttggttcgg | ggaactccta | ttactactac | ggtatggacg | tctggggcca | agggaccacg | 360 |
| gtcaccgtct | cctca | | | | | 375 |

<210> SEQ ID NO 51
<211> LENGTH: 354
<212> TYPE: DNA
<213> ORGANISM: Homo sapiens

<400> SEQUENCE: 51

| | | | | | |
|---|---|---|---|---|---|
| caggtgcagc | tgcaggagtc | gggcccagga | ctggtgaagc | cttcggggac | cctgtccctc | 60 |
| acctgcgctg | tctctggtgg | ctccatcagc | aggaataatt | ggtggagttg | ggtccgccag | 120 |
| cccccaggga | aggggctgga | gtggattggg | gaaatctatc | atagtgggag | caccaactac | 180 |
| aacccgtccc | tcaagagtcg | agtcaccata | tcagtagaca | agtccaagaa | ccagttctcc | 240 |
| ctgaagctga | gctctgtgac | ggccgcggac | acggccgtgt | attactgtgc | gagagatctg | 300 |
| ctggggatcg | gtcttgacta | ctggggccag | ggaaccctgg | tcaccgtctc | ctca | 354 |

<210> SEQ ID NO 52
<211> LENGTH: 387
<212> TYPE: DNA
<213> ORGANISM: Homo sapiens

<400> SEQUENCE: 52

| | | | | | |
|---|---|---|---|---|---|
| gaggtgcagc | tggtggagtc | tgggggaggc | ttggtccagc | ctggagggtc | cctgagactc | 60 |
| tcctgtgcag | cctctgaatt | cacctttggt | ggctattgga | tgacctgggt | ccgccaggct | 120 |
| ccagggaagg | ggctggagtg | ggtggccaac | ataaagcaag | atggaagtga | gaaatactat | 180 |
| gtggactctg | tgaagggccg | attcaccatc | tccagagaca | acgccaagaa | ctcactgtat | 240 |
| ctgcacatga | acagcctgag | agccgaggac | acggctgtat | attactgtgc | gagagatcgg | 300 |
| actactatga | ttcgggggagt | ctctctttac | tactactact | acggtatgga | cgtctggggc | 360 |
| caagggaccg | cggtcaccgt | ctcctca | | | | 387 |

<210> SEQ ID NO 53
<211> LENGTH: 390
<212> TYPE: DNA
<213> ORGANISM: Homo sapiens

<400> SEQUENCE: 53

| | | | | | |
|---|---|---|---|---|---|
| gaggtgcagc | tggtggagtc | tgggggaggc | ttggtccagc | ctgggggtc | cctgagactc | 60 |
| tcctgtgcag | cctctggaat | caccttttagt | agctattgga | tgagctgggt | ccgccaggct | 120 |
| ccagggaagg | ggctggagtg | ggtggccaac | ataaagcaag | atggaagtga | gaaatactat | 180 |

```
gtggactctg tgaagggccg attcaccatc tccagagaca tcgccaagaa ctcactgtat    240
ctgcaaatga acagcctgag agccgaggac acggctgtgt attactgtgc gagagatagg    300
ggaacgtatt actatggttc ggggagttat aactactact actacggtat ggacgtctgg    360
ggccaaggga ccacggtcac cgtctcctca                                     390
```

<210> SEQ ID NO 54
<211> LENGTH: 363
<212> TYPE: DNA
<213> ORGANISM: Homo sapiens

<400> SEQUENCE: 54

```
caggtgcagc tgcaggagtc gggcccagga ctggtgaagc cttcgggac cctgtccctc      60 acctgcgctg tctctggtgg ctccatcagc agtagtaact ggtggagttg gtccgccag     120 cccccaggga aggggctgga gtggattggg gaaatctatc atagtgggag caccaactac    180
aacccgtccc tcaagagtcg agtcaccata tcagtagaca gtccaagaa ccagttctcc    240 ctgaagctga gctctgtgac cgccgcggac acggccgtgt attactgtgc gagaggaata    300
gcagtggctg gtacggatgt tatggatgcc tggggtcaag gagcttcagt cactgtctcc    360
tca                                                                 363
```

<210> SEQ ID NO 55
<211> LENGTH: 321
<212> TYPE: DNA
<213> ORGANISM: Homo sapiens

<400> SEQUENCE: 55

```
gacatccagt tgacccagtc tccatccttc ctgtctgcat ctgtaggaga cagagtcacc     60
atcacttgcc gggccagtca gggcattagt agttatttag cctggtatca gcaaaaacca   120
gggaaagccc ctaagctcct gatctatgct gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaatagtt accctcggac gttcggccaa   300
gggaccaagg tggaaatcaa a                                              321
```

<210> SEQ ID NO 56
<211> LENGTH: 321
<212> TYPE: DNA
<213> ORGANISM: Homo sapiens

<400> SEQUENCE: 56

```
gacatccaga tgacccagtc tccatcctcc ctgtctgcat ctgtaggaga cagagtcacc     60
atcacttgcc gggcgagtca ggtcattagc aattatttag cctggtatca gcagaaacca   120
gggaaagttc ctaagctcct gatctatact gcatccactt tacaatcagg ggtcccttct   180
cggttcagtg gcagtggatc tggggcagat ttcactctca ccatcagcag cctgcagcct   240
gaagatgttg caacttatta ctgtcaaaag tataacagtg ccccgtacac ttttggccag   300
gggaccaagc tggagatcaa a                                              321
```

<210> SEQ ID NO 57
<211> LENGTH: 321
<212> TYPE: DNA
<213> ORGANISM: Homo sapiens

<400> SEQUENCE: 57

```
gaatttgtgt tgacacagtc tccagccacc ctgtctttgt ctccaggtga aagagccatc     60
```

| | | | |
|---|---|---|---|
| ctctcctgca gggccagtca gagttttagc agctacatag cctggtacca acagaaacct | | | 120 |
| ggccaggctc ccaggctcct catctatgat gcatccaaca gggccactgg catcccagcc | | | 180 |
| aggttcagtg gcagtgggtc tgggacagac ttcactctca ccatcagcag cctagagcct | | | 240 |
| gaagattttg cagtttatta ctgtcagcag catagcaact ggatgtacac ttttggccag | | | 300 |
| gggaccaagc tggagatcaa a | | | 321 |

<210> SEQ ID NO 58
<211> LENGTH: 321
<212> TYPE: DNA
<213> ORGANISM: Homo sapiens

<400> SEQUENCE: 58

| | | | |
|---|---|---|---|
| gaaattgtgt tgacacagtc tccagccacc ctgtctttgt ctccagggga aagagccacc | | | 60 |
| ctctcctgca gggccagtca gagtgttagc agctacttag cctggtacca acagaaacct | | | 120 |
| ggccaggctc ccaggctcct catctatgat gcatccaaca gggccactgg catcccagcc | | | 180 |
| aggttcagtg gcagtgggtc tgggacagac ttcactctca ccatcagcag cctagagcct | | | 240 |
| gaagattttg cagtttatta ctgtcagcag cgtagcaact ggcctctcac tttcggcgga | | | 300 |
| gggaccaagg tggagatcaa a | | | 321 |

<210> SEQ ID NO 59
<211> LENGTH: 321
<212> TYPE: DNA
<213> ORGANISM: Homo sapiens

<400> SEQUENCE: 59

| | | | |
|---|---|---|---|
| gacatccaga tgacccagtc tccttccacc ctgtctgcat ctgtaggaga cagagtcacc | | | 60 |
| atcacttgcc gggccagtca gagtattagt agttggttgg cctggtatca gcagaaacca | | | 120 |
| gggaaagccc ctaagctcct gatctataag gcgtctagtt tagaaagtgg ggtcccatca | | | 180 |
| aggttcagcg gcagtggatc tgggacagaa ttcactctca ccatcagcag cctgcagcct | | | 240 |
| gatgattttg caacttatta ctgccaacag tataatagtt attcgtacac ttttggccag | | | 300 |
| gggaccaagc tggagatcaa a | | | 321 |

<210> SEQ ID NO 60
<211> LENGTH: 321
<212> TYPE: DNA
<213> ORGANISM: Homo sapiens

<400> SEQUENCE: 60

| | | | |
|---|---|---|---|
| gaaattgtgt tgacacagtc tccagccacc ctgtctttgt ctccagggga aagagccacc | | | 60 |
| ctctcctgca gggccagtca gagtgttagc agctacttag tttggtacca acagaaatct | | | 120 |
| ggccaggctc ccaggctcct catctatggt acatccaaca gggccactgg catcccagcc | | | 180 |
| aggttcagtg gcagtgggtc tgggacagac ttcactctca ccatcagcag cctagagcct | | | 240 |
| gaagattttg cactttatta ctgtcagcag cgtggcaact ggatgtacac ttttggccag | | | 300 |
| gggaccaagc tggagatcaa a | | | 321 |

<210> SEQ ID NO 61
<211> LENGTH: 2079
<212> TYPE: DNA
<213> ORGANISM: Homo sapiens

<400> SEQUENCE: 61

```
atgggcaccg tcagctccag gcggtcctgg tggccgctgc cactgctgct gctgctgctg    60
ctgctcctgg gtcccgcggg cgcccgtgcg caggaggacg aggacggcga ctacgaggag   120
ctggtgctag ccttgcgttc cgaggaggac ggcctggccg aagcacccga gcacggaacc   180
acagccacct ccaccgctg cgccaaggat ccgtggaggt tgcctggcac ctacgtggtg    240
gtgctgaagg aggagaccca cctctcgcag tcagagcgca ctgcccgccg cctgcaggcc   300
caggctgccc gccggggata cctcaccaag atcctgcatg tcttccatgg ccttcttcct   360
ggcttcctgg tgaagatgag tggcgacctg ctggagctgg ccttgaagtt gccccatgtc   420
gactacatcg aggaggactc ctctgtcttt gcccagagca tcccgtggaa cctggagcgg   480
attacccctc cacggtaccg gcggatgaa taccagcccc ccgacggagg cagcctggtg    540
gaggtgtatc tcctagacac cagcatacag agtgaccacc gggaaatcga gggcagggtc   600
atggtcaccg acttcgagaa tgtgcccgag gaggacggga cccgcttcca cagacaggcc   660
agcaagtgtg acagtcatgg cacccacctg cagggtgtgg tcagcggccg ggatgccggc   720
gtggccaagg tgccagcat gcgcagcctg cgcgtgctca actgccaagg aagggcacg     780
gttagcggca ccctcatagg cctggagttt attcggaaaa gccagctggt ccagcctgtg   840
gggccactgg tggtgctgct gccccctggcg ggtgggtaca gccgcgtcct caacgccgcc   900
tgccagcgcc tggcgagggc tggggtcgtg ctggtcaccg ctgccggcaa cttccgggac   960
gatgcctgcc tctactcccc agcctcagct cccgaggtca tcacagttgg ggccaccaat  1020
gcccaagacc agccggtgac cctggggact tgggggacca actttggccg ctgtgtggac  1080
ctctttgccc caggggagga catcattggt gcctccagcg actgcagcac ctgctttgtg  1140
tcacagagtg ggacatcaca ggctgctgcc cacgtggctg gcattgcagc catgatgctg  1200
tctgccgagc cggagctcac cctggccgag ttgaggcaga gactgatcca cttctctgcc  1260
aaagatgtca tcaatgaggc ctggttccct gaggaccagc gggtactgac ccccaacctg  1320
gtggccgccc tgcccccag cacccatggg gcaggttggc agctgttttg caggactgta   1380
tggtcagcac actcggggcc tacacggatg ccacagccg tcgcccgctg cgccccagat   1440
gaggagctgc tgagctgctc cagtttctcc aggagtggga gcggcgggg cgagcgcatg   1500
gaggcccaag ggggcaagct ggtctgccgg gcccacaacg cttttgggg tgagggtgtc   1560
tacgccattg ccaggtgctg cctgctaccc caggccaact gcagcgtcca cacagctcca  1620
ccagctgagg ccagcatggg gacccgtgtc cactgccacc aacagggcca cgtcctcaca   1680
ggctgcagct cccactggga ggtggaggac cttggcaccc acaagccgcc tgtgctgagg   1740
ccacgaggtc agcccaacca gtgcgtgggc cacagggagg ccagcatcca cgcttcctgc  1800
tgccatgccc caggtctgga atgcaaagtc aaggagcatg gaatcccggc ccctcaggag  1860
caggtgaccg tggcctgcga ggagggctgg accctgactg gctgcagtgc cctccctggg  1920
acctcccacg tcctgggggc ctacgccgta gacaacacgt gtgtagtcag gagccgggac  1980
gtcagcacta caggcagcac cagcgaaggg ccgtgacag ccgttgccat ctgctgccgg   2040
agccggcacc tggcgcaggc ctcccaggag ctccagtga                          2079
```

<210> SEQ ID NO 62  
<211> LENGTH: 692  
<212> TYPE: PRT  
<213> ORGANISM: Homo sapiens

<400> SEQUENCE: 62

Met Gly Thr Val Ser Ser Arg Arg Ser Trp Trp Pro Leu Pro Leu Leu

-continued

```
1               5                   10                  15
Leu Leu Leu Leu Leu Leu Leu Gly Pro Ala Gly Ala Arg Ala Gln Glu
                20                  25                  30
Asp Glu Asp Gly Asp Tyr Glu Leu Val Leu Ala Leu Arg Ser Glu
                35                  40                  45
Glu Asp Gly Leu Ala Glu Ala Pro Glu His Gly Thr Thr Ala Thr Phe
50                  55                  60
His Arg Cys Ala Lys Asp Pro Trp Arg Leu Pro Gly Thr Tyr Val Val
65                  70                  75                  80
Val Leu Lys Glu Glu Thr His Leu Ser Gln Ser Glu Arg Thr Ala Arg
                85                  90                  95
Arg Leu Gln Ala Gln Ala Ala Arg Arg Gly Tyr Leu Thr Lys Ile Leu
                100                 105                 110
His Val Phe His Gly Leu Leu Pro Gly Phe Leu Val Lys Met Ser Gly
                115                 120                 125
Asp Leu Leu Glu Leu Ala Leu Lys Leu Pro His Val Asp Tyr Ile Glu
                130                 135                 140
Glu Asp Ser Ser Val Phe Ala Gln Ser Ile Pro Trp Asn Leu Glu Arg
145                 150                 155                 160
Ile Thr Pro Pro Arg Tyr Arg Ala Asp Glu Tyr Gln Pro Pro Asp Gly
                165                 170                 175
Gly Ser Leu Val Glu Val Tyr Leu Leu Asp Thr Ser Ile Gln Ser Asp
                180                 185                 190
His Arg Glu Ile Glu Gly Arg Val Met Val Thr Asp Phe Glu Asn Val
                195                 200                 205
Pro Glu Glu Asp Gly Thr Arg Phe His Arg Gln Ala Ser Lys Cys Asp
210                 215                 220
Ser His Gly Thr His Leu Ala Gly Val Val Ser Gly Arg Asp Ala Gly
225                 230                 235                 240
Val Ala Lys Gly Ala Ser Met Arg Ser Leu Arg Val Leu Asn Cys Gln
                245                 250                 255
Gly Lys Gly Thr Val Ser Gly Thr Leu Ile Gly Leu Glu Phe Ile Arg
                260                 265                 270
Lys Ser Gln Leu Val Gln Pro Val Gly Pro Leu Val Val Leu Leu Pro
                275                 280                 285
Leu Ala Gly Gly Tyr Ser Arg Val Leu Asn Ala Ala Cys Gln Arg Leu
                290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
                340                 345                 350
Thr Asn Phe Gly Arg Cys Val Asp Leu Phe Ala Pro Gly Glu Asp Ile
                355                 360                 365
Ile Gly Ala Ser Ser Tyr Cys Ser Thr Cys Phe Val Ser Gln Ser Gly
                370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
```

```
Gln Arg Val Leu Thr Pro Asn Leu Val Ala Ala Leu Pro Pro Ser Thr
        435                 440                 445
His Gly Ala Gly Trp Gln Leu Phe Cys Arg Thr Val Trp Ser Ala His
    450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
            500                 505                 510
Asn Ala Phe Gly Gly Glu Gly Val Tyr Ala Ile Ala Arg Cys Cys Leu
        515                 520                 525
Leu Pro Gln Ala Asn Cys Ser Val His Thr Ala Pro Pro Ala Glu Ala
    530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
            580                 585                 590
Glu Ala Ser Ile His Ala Ser Cys Cys His Ala Pro Gly Leu Glu Cys
        595                 600                 605
Lys Val Lys Glu His Gly Ile Pro Ala Pro Gln Glu Gln Val Thr Val
    610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
            660                 665                 670
Thr Ala Val Ala Ile Cys Cys Arg Ser Arg His Leu Ala Gln Ala Ser
        675                 680                 685
Gln Glu Leu Gln
    690

<210> SEQ ID NO 63
<211> LENGTH: 2079
<212> TYPE: DNA
<213> ORGANISM: Macaca fascicularis

<400> SEQUENCE: 63
atgggtaccg tcagctccag gcggtcctgg tggcctctgc cgctgccact gctgctgctc      60
ctgctcctgg gtcccgctgg cgcccgtgcg caggaggacg aggacggcga ctacgaggag     120
ctggtgctag ccttgcgttc gaggaggac ggcctggccg acgcacccga gcacggagcc     180
acagccacct tccaccgctg cgccaaggat ccgtggaggc tgcccggcac ctacgtggtg     240
gtgctgaagg aggagaccca ccgctcgcag tcagagcgca ctgcccgccg cctgcaggcc     300
caagctgccc gccggggata cctcaccaag atcctgcatg tcttccatca ccttcttcct     360
ggcttcctgg tgaagatgag tggcgacctg ctggagctgg ccctgaagtt gccccatgtc     420
gactacatcg aggaggactc ctctgtcttt gcccagagca tcccatggaa cctggagcga     480
attactcctg cacggtaccg ggcggatgaa taccagcccc ccaaaggagg cagcctggtg     540
gaggtgtatc tcctagacac cagcatacag agtgaccacc gggaaatcga gggcagggtc     600
```

```
atggtcaccg acttcgagag tgtgcccgag gaggacggga cccgcttcca cagacaggcc    660
agcaagtgtg acagccatgg cacccacctg cagggggtgg tcagcggccg ggatgccggc    720
gtggccaagg tgccggcct gcgtagcctg cgcgtgctca actgccaagg aagggcacg    780
gtcagcggca ccctcatagg tctggagttt attcggaaaa gccagctggt ccagcccgtg    840
gggccactgg ttgtgctgct gcccctggcg ggtgggtaca gccgggtctt caacgccgcc    900
tgccagcgcc tggcgagggc tggggtcgtg ctggtcaccg ctgccggcaa cttccgggac    960
gatgcctgcc tctactcccc agcctcggct cccgaggtca tcacagttgg ggccaccaat   1020
gcccaggacc agccggtgac cctggggact ttggggacca ctttggccg ctgtgtggac   1080
ctctttgccc caggggagga catcattggt gcctccagcg actgcagcac ctgctttgtg   1140
tcacggagtg ggacatcgca ggctgctgcc cacgtggctg gcattgcagc catgatgctg   1200
tctgccgagc cggagctcac tctggccgag ttgaggcaga gactgatcca cttctctgcc   1260
aaagatgtca tcaatgaggc ctggttccct gaggaccagc gggtactgac ccccaacctg   1320
gtggccgccc tgcccccag cacccacagg gcaggttggc agctgttttg caggactgtg   1380
tggtcagcac actcggggcc tacacggatg ccacagccg tagcccgctg cgcccaggat   1440
gaggagctgc tgagctgctc cagtttctcc aggagtggga gcggcgggg cgagcgcatc   1500
gaggcccaag ggggcaagcg ggtctgccgg gcccacaacg cttttggggg tgagggtgtc   1560
tacgccattg ccaggtgctg cctgctaccc caggtcaact gcagcgtcca cacagctcca   1620
ccagctgggg ccagcatggg gacccgtgtc cactgccatc agcagggcca cgtcctcaca   1680
ggctgcagct cccactggga ggtggaggac cttggcaccc acaagccgcc tgtgctgagg   1740
ccacgaggtc agcccaacca gtgtgtgggc cacaggagg ccagcatcca cgcttcctgc   1800
tgccatgccc caggtctgga atgcaaagtc aaggagcatg gaatcccggc ccctcaggag   1860
caggttatcg tggcctgtga ggacggctgg accctgaccg gctgcagtcc cctccctggg   1920
acctcccatg tcctgggggc ctacgctgta gacaacacgt gtgtggtcag gagccgggac   1980
gtcagcacca caggcagcac cagcaaagaa gccgtggcag ccgttgccat ctgctgccgg   2040
agccggcacc tggtgcaggc ctcccaagag ctccagtga                          2079
```

`<210> SEQ ID NO 64`
`<211> LENGTH: 2301`
`<212> TYPE: DNA`
`<213> ORGANISM: Homo sapiens`

`<400> SEQUENCE: 64`

```
gcagtgggcg acagatgcga aagaaacgag ttccagtgcc aagacgggaa atgcatctcc     60
tacaagtggg tctgcgatgg cagcgctgag tgccaggatg ctctgatga gtcccaggag    120
acgtgcttgt ctgtcaccctg caaatccggg gacttcagct gtgggggccg tgtcaaccgc    180
tgcattcctc agttctggag gtgcgatggc caagtggact cgacaacgg ctcagacgag    240
caaggctgtc cccccaagac gtgctcccag gacgagtttc gctgccacga tgggaagtgc    300
atctctcggc agttcgtctg tgactcagac cgggactgct tggacggctc agacgaggcc    360
tcctgcccgg tgctcacctg tggtcccgcc agcttccagt gcaacagctc cacctgcatc    420
ccccagctgt gggcctgcga caacgacccc gactgcgaag atggctcgga tgagtggccg    480
cagcgctgta ggggtcttta cgtgttccaa gggacagta gccctgctc ggccttcgag    540
ttccactgcc taagtggcga gtgcatccac tccagctggc gctgtgatgg tggccccgac    600
```

```
tgcaaggaca aatctgacga ggaaaactgc gctgtggcca cctgtcgccc tgacgaattc      660
cagtgctctg atggaaactg catccatggc agccggcagt gtgaccggga atatgactgc      720
aaggacatga gcgatgaagt tggctgcgtt aatgtgacac tctgcgaggg acccaacaag      780
ttcaagtgtc acagcggcga atgcatcacc ctggacaaag tctgcaacat ggctagagac      840
tgccgggact ggtcagatga acccatcaaa gagtgcggga ccaacgaatg cttggacaac      900
aacggcggct gttcccacgt ctgcaatgac cttaagatcg gctacgagtg cctgtgcccc      960
gacggcttcc agctggtggc ccagcgaaga tgcgaagata tcgatgagtg tcaggatccc     1020
gacacctgca gccagctctg cgtgaacctg gaggtggct acaagtgcca gtgtgaggaa     1080
ggcttccagc tggaccccca cacgaaggcc tgcaaggctg tgggctccat cgcctacctc     1140
ttcttcacca accggcacga ggtcaggaag atgacgctgg accggagcga gtacaccagc     1200
ctcatcccca acctgaggaa cgtggtcgct ctggacacgg aggtggccag caatagaatc     1260
tactggtctg acctgtccca gagaatgatc tgcagcaccc agcttgacag agcccacggc     1320
gtctcttcct atgacaccgt catcagcaga gacatccagg cccccgacgg gctggctgtg     1380
gactggatcc acagcaacat ctactggacc gactctgtcc tgggcactgt ctctgttgcg     1440
gataccaagg gcgtgaagag gaaaacgtta ttcaggagaa acggctccaa gccaagggcc     1500
atcgtggtgg atcctgttca tggcttcatg tactggactg actggggaac tcccgccaag     1560
atcaagaaag ggggcctgaa tggtgtggac atctactcgc tggtgactga aaacattcag     1620
tggcccaatg gcatcaccct agatctcctc agtggccgcc tctactgggt tgactccaaa     1680
cttcactcca tctcaagcat cgatgtcaac ggggcaacc ggaagaccat cttggaggat     1740
gaaaagaggc tggcccaccc cttctccttg gccgtctttg aggacaaagt attttggaca     1800
gatatcatca cgaagccat tttcagtgcc aaccgcctca caggttccga tgtcaacttg     1860
ttggctgaaa acctactgtc cccagaggat atggttctct ccacaacct cacccagcca     1920 agaggagtga actggtgtga gaggaccacc ctgagcaatg cggctgcca gtatctgtgc     1980 ctccctgccc cgcagatcaa ccccccactcg cccaagttta cctgcgcctg cccggacggc     2040
atgctgctgg ccaggacat gaggagctgc ctcacagagg ctgaggctgc agtggccacc     2100
caggagacat ccaccgtcag gctaaaggtc agctccacag ccgtaaggac acagcacaca     2160
accacccgac tgttcccga cacctccggg ctgcctgggg ccaccctgg gctcaccacg     2220 gtggagatag tgacaatgtc tcaccaagct ctgggcgacg ttgctggcag aggaaatgag     2280
aagaagccca gtagcgtgag g                                              2301
```

<210> SEQ ID NO 65
<211> LENGTH: 2085
<212> TYPE: DNA
<213> ORGANISM: Mus musculus

<400> SEQUENCE: 65

```
atgggcaccc actgctctgc gtggctgcgg tggccgctgt gccgctgtt gccgccgctg       60 ctgctgctgt tgctgctact gtgccccacc ggcgctggtg cccaggacga ggatggagat      120
tatgaagagc tgatgctcgc cctcccgtcc caggaggatg gcctggctga tgaggccgca      180
catgtggcca ccgccacctt ccgccgttgc tccaaggagg cctggaggct gccaggaacc      240
tacattgtgg tgctgatgga ggagacccag aggctacaga ttgaacaaac tgcccaccgc      300
ctgcagaccc gggctgcccg ccggggctat gtcatcaagg ttctacatat cttttatgac      360
ctcttccctg gcttcttggt gaagatgagc agtgacctgt gggcctggc cctgaagttg      420
```

```
ccccatgtgg agtacattga ggaagactcc tttgtcttcg cccagagcat cccatggaac    480
ctggagcgaa ttatcccagc atggcaccag acagaggaag accgctcccc tgatggaagc    540
agccaggtgg aggtgtatct cttagatacc agcatccagg gtgcccatcg ggagattgag    600
ggcagggtca ccatcaccga cttcaacagc gtgccgagg aggatgggac acgcttccac     660
agacaggcga gcaagtgtga cagccacggc acccacctgg caggtgtggt cagcggccgg    720
gatgctggtg tggccaaggg caccagcctg cacagcctgc gtgtgctcaa ctgtcaaggg    780
aagggcacag tcagcggcac cctcataggc ctggagttta ttcggaagag tcagctaatc    840
cagccctcgg ggccactcgt ggttctgctg cccctggccg gtgggtatag ccgcatcctc    900
aacgctgcct gccggcacct ggcgaggact ggggtggtgc tggttgcagc agctgggaac    960
ttccgggacg acgcctgcct ctactcccca gcttctgctc agaggtcat cacagtcggg    1020 gccacgaatg cccaggacca gccagttacc ttggggactt tggggactaa ttttggacgc    1080
tgtgtggatc tctttgcccc cgggaaggac atcatcggag cgtccagtga ctgcagcaca    1140
tgcttcatgt cacagagtgg gacctcacag gctgctgccc acgtggccgg cattgtggct    1200
cggatgctga gccgggagcc cacacttacc ctggccgagc tgcggcagag gctgatccac    1260
ttctctacca aagacgtcat caacatggcc tggttccctg aggaccagca ggtgctgacc    1320
cccaacctgg tggccacact gccccccagc acccatgaga caggcgggca gctgctctgt    1380
aggacggtgt ggtcggcaca ctcggggccc actcgaacag ctacagctac agcccgctgt    1440
gccccagaag aggagctgct gagctgctcc agcttctcca ggagcgggag gcgtcgtggt    1500
gattggattg aggccatagg aggccagcag gtctgcaagg ccctcaatgc atttgggggt    1560
gagggtgtct atgccgtcgc gagatgctgc ctggttcccc gtgccaactg cagcatccac    1620
aacacccctg cagccagagc tggcctggag acccatgtcc actgccacca aaggaccat    1680 gttctcacag gctgcagctt ccattgggaa gtggaagacc ttagtgtccg gaggcagcct    1740
gcgctgaggt ccagacgtca gcctggccag tgcgttggcc accaggcggc cagtgtctat    1800
gcttcctgct gccatgcccc agggctgaat gcaaaatca aggagcatgg gatctcaggt     1860
ccttcagagc aggtcactgt ggcctgcgaa gcaggatgga ccctgactgg atgcaatgtg    1920
ctccctgggg catccctcac tctgggagcc tacagcgtgg acaacctgtg tgtggcaaga    1980
gtccatgaca ctgccagagc agacaggacc agtggagaag ccacagtagc tgctgccatc    2040
tgctgccgga gccggccttc agcaaaggcc tcctgggttc agtga                    2085
```

<210> SEQ ID NO 66
<211> LENGTH: 990
<212> TYPE: DNA
<213> ORGANISM: Artificial Sequence
<220> FEATURE:
<223> OTHER INFORMATION: human IgG1 constant region

<400> SEQUENCE: 66

```
gcttcgacca agggcccatc ggtcttcccc ctggcaccct cctccaagag cacctctggg    60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaagc cgcgggggga    360
```

```
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgcgaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 67
<211> LENGTH: 330
<212> TYPE: PRT
<213> ORGANISM: Artificial Sequence
<220> FEATURE:
<223> OTHER INFORMATION: human IgG1 constant region

<400> SEQUENCE: 67

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 68
<211> LENGTH: 324
<212> TYPE: DNA
<213> ORGANISM: Artificial Sequence
<220> FEATURE:
<223> OTHER INFORMATION: human antibody light chain kappa constant
      region

<400> SEQUENCE: 68
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttga                                          324

<210> SEQ ID NO 69
<211> LENGTH: 107
<212> TYPE: PRT
<213> ORGANISM: Artificial Sequence
<220> FEATURE:
<223> OTHER INFORMATION: human antibody light chain kappa constant
      region

<400> SEQUENCE: 69

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 70
<211> LENGTH: 47
<212> TYPE: DNA
<213> ORGANISM: Artificial Sequence
<220> FEATURE:
<223> OTHER INFORMATION: CDRH3-1_mut-F
<220> FEATURE:
```

```
<221> NAME/KEY: misc_feature
<222> LOCATION: (19)..(29)
<223> OTHER INFORMATION: n is a, c, g, or t

<400> SEQUENCE: 70
gtgtattact gtgcgagann nnnnnnnnnt ataactacta ctactac                47

<210> SEQ ID NO 71
<211> LENGTH: 48
<212> TYPE: DNA
<213> ORGANISM: Artificial Sequence
<220> FEATURE:
<223> OTHER INFORMATION: CDRH3-2_mut-F
<220> FEATURE:
<221> NAME/KEY: misc_feature
<222> LOCATION: (21)..(30)
<223> OTHER INFORMATION: n is a, c, g, or t

<400> SEQUENCE: 71
attactatgg ttcggggagt nnnnnnnnnn tggggccaag ggaccacg             48

<210> SEQ ID NO 72
<211> LENGTH: 48
<212> TYPE: DNA
<213> ORGANISM: Artificial Sequence
<220> FEATURE:
<223> OTHER INFORMATION: artificial sequence CDRL3_mut-F
<220> FEATURE:
<221> NAME/KEY: misc_feature
<222> LOCATION: (21)..(29)
<223> OTHER INFORMATION: n is a, c, g, or t

<400> SEQUENCE: 72
attttgcaac ttattactgc nnnnnnnnnt ttggccaggg gaccaagc             48

<210> SEQ ID NO 73
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 73

Asp Arg Gly Thr Tyr Tyr Tyr Gly Ile Gly Ser Tyr Asn Tyr Tyr Tyr
1               5                   10                  15

Tyr Gly Met Asp Val
            20

<210> SEQ ID NO 74
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 74

Asp Arg Gly Thr Tyr Tyr Tyr Trp Leu Gly Thr Tyr Asn Tyr Tyr Tyr
1               5                   10                  15

Tyr Gly Met Asp Val
            20

<210> SEQ ID NO 75
<211> LENGTH: 21
<212> TYPE: PRT
<213> ORGANISM: Artificial Sequence
<220> FEATURE:
<223> OTHER INFORMATION: CDRH3 sequence
```

```
<400> SEQUENCE: 75

Asp Arg Gly Thr Tyr Tyr Tyr Ala Ser Gly Ser Tyr Asn Tyr Tyr
1               5                   10                  15

Tyr Gly Met Asp Val
            20

<210> SEQ ID NO 76
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 76

Asp Arg Gly Thr Tyr Tyr Tyr Asp Ser Gly Gly Tyr Asn Tyr Tyr
1               5                   10                  15

Tyr Gly Met Asp Val
            20

<210> SEQ ID NO 77
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 77

Asp Arg Gly Thr Tyr Tyr His Trp Leu Gly Ser Tyr Asn Tyr Tyr
1               5                   10                  15

Tyr Gly Met Asp Val
            20

<210> SEQ ID NO 78
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 78

Asp Arg Gly Thr Tyr Tyr Phe Gln Ser Gly Ser Tyr Asn Tyr Tyr
1               5                   10                  15

Tyr Gly Met Asp Val
            20

<210> SEQ ID NO 79
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 79

Asp Arg Gly Thr Tyr Tyr Gln Gln Gly Ser Tyr Asn Tyr Tyr Tyr
1               5                   10                  15

Tyr Gly Met Asp Val
            20

<210> SEQ ID NO 80
<211> LENGTH: 21
<212> TYPE: PRT
<213> ORGANISM: Artificial Sequence
<220> FEATURE:
```

<223> OTHER INFORMATION: CDRH3 sequence

<400> SEQUENCE: 80

Asp Arg Gly Thr Tyr Tyr Ile Ala Asp Gly Ser Tyr Asn Tyr Tyr
1               5                   10                  15

Tyr Gly Met Asp Val
            20

<210> SEQ ID NO 81
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 81

Asp Arg Gly Thr Tyr Tyr Tyr Asp Ser Gly Arg Tyr Asn Tyr Tyr
1               5                   10                  15

Tyr Gly Met Asp Val
            20

<210> SEQ ID NO 82
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 82

Asp Arg Gly Thr Tyr Tyr Tyr Gln Glu Gly Ser Tyr Asn Tyr Tyr
1               5                   10                  15

Tyr Gly Met Asp Val
            20

<210> SEQ ID NO 83
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 83

Asp Arg Gly Thr Tyr Tyr Tyr Thr Glu Gly Gly Tyr Asn Tyr Tyr
1               5                   10                  15

Tyr Gly Met Asp Val
            20

<210> SEQ ID NO 84
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 84

Asp Arg Gly Thr Tyr Tyr Tyr Thr Glu Gly Ser Tyr Asn Tyr Tyr
1               5                   10                  15

Tyr Gly Met Asp Val
            20

<210> SEQ ID NO 85
<211> LENGTH: 21
<212> TYPE: PRT
<213> ORGANISM: Artificial Sequence

```
<220> FEATURE:
<223> OTHER INFORMATION: CDRH3 sequence

<400> SEQUENCE: 85

Asp Arg Gly Thr Tyr Tyr Tyr Ala Asp Gly Tyr Asn Tyr Tyr
1               5                   10                  15

Tyr Gly Met Asp Val
            20

<210> SEQ ID NO 86
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 86

Asp Arg Gly Thr Tyr Tyr Tyr Gln Asp Gly Asn Tyr Asn Tyr Tyr
1               5                   10                  15

Tyr Gly Met Asp Val
            20

<210> SEQ ID NO 87
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 87

Asp Arg Gly Thr Tyr Tyr Tyr Gln Asp Gly Lys Tyr Asn Tyr Tyr
1               5                   10                  15

Tyr Gly Met Asp Val
            20

<210> SEQ ID NO 88
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 88

Asp Arg Gly Thr Tyr Tyr Thr Gly Met Gly Glu Tyr Asn Tyr Tyr
1               5                   10                  15

Tyr Gly Met Asp Val
            20

<210> SEQ ID NO 89
<211> LENGTH: 21
<212> TYPE: PRT
<213> ORGANISM: Artificial Sequence
<220> FEATURE:
<223> OTHER INFORMATION: CDRH3 sequence

<400> SEQUENCE: 89

Asp Arg Gly Thr Tyr Tyr Tyr Ala Asp Gly Asp Tyr Asn Tyr Tyr
1               5                   10                  15

Tyr Gly Met Asp Val
            20

<210> SEQ ID NO 90
<211> LENGTH: 21
<212> TYPE: PRT
```

```
<213> ORGANISM: Artificial Sequence
<220> FEATURE:
<223> OTHER INFORMATION: CDRH3 sequence

<400> SEQUENCE: 90

Asp Arg Gly Thr Tyr Tyr Tyr Ala Ser Gly Lys Tyr Asn Tyr Tyr
1               5                   10                  15

Tyr Gly Met Asp Val
            20

<210> SEQ ID NO 91
<211> LENGTH: 130
<212> TYPE: PRT
<213> ORGANISM: Artificial Sequence
<220> FEATURE:
<223> OTHER INFORMATION: heavy chain sequence

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Gly Ile Gly Ser Tyr Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 92
<211> LENGTH: 130
<212> TYPE: PRT
<213> ORGANISM: Artificial Sequence
<220> FEATURE:
<223> OTHER INFORMATION: heavy chain sequence

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Trp Leu Gly Thr Tyr Asn Tyr
            100                 105                 110
```

Tyr Tyr Tyr Gly Met Asp Val Trp Gly Gln Gly Thr Thr Val Thr Val
            115                 120                 125

Ser Ser
    130

<210> SEQ ID NO 93
<211> LENGTH: 130
<212> TYPE: PRT
<213> ORGANISM: Artificial Sequence
<220> FEATURE:
<223> OTHER INFORMATION: heavy chain sequence

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Ala Ser Gly Ser Tyr Asn Tyr
            100                 105                 110

Tyr Tyr Tyr Gly Met Asp Val Trp Gly Gln Gly Thr Thr Val Thr Val
            115                 120                 125

Ser Ser
    130

<210> SEQ ID NO 94
<211> LENGTH: 130
<212> TYPE: PRT
<213> ORGANISM: Artificial Sequence
<220> FEATURE:
<223> OTHER INFORMATION: heavy chain sequence

<400> SEQUENCE: 94

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Asp Ser Gly Tyr Asn Tyr
            100                 105                 110

Tyr Tyr Tyr Gly Met Asp Val Trp Gly Gln Gly Thr Thr Val Thr Val
            115                 120                 125

Ser Ser

<210> SEQ ID NO 95
<211> LENGTH: 130
<212> TYPE: PRT
<213> ORGANISM: Artificial Sequence
<220> FEATURE:
<223> OTHER INFORMATION: heavy chain sequence

<400> SEQUENCE: 95

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr His Trp Leu Gly Ser Tyr Asn Tyr
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 96
<211> LENGTH: 130
<212> TYPE: PRT
<213> ORGANISM: Artificial Sequence
<220> FEATURE:
<223> OTHER INFORMATION: heavy chain sequence

<400> SEQUENCE: 96

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Phe Gln Ser Gly Ser Tyr Asn Tyr
            100                 105                 110

Tyr Tyr Tyr Gly Met Asp Val Trp Gly Gln Gly Thr Thr Val Thr Val
        115                 120                 125

Ser Ser
    130
```

<210> SEQ ID NO 97
<211> LENGTH: 130

```
<212> TYPE: PRT
<213> ORGANISM: Artificial Sequence
<220> FEATURE:
<223> OTHER INFORMATION: heavy chain sequence

<400> SEQUENCE: 97
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Thr Tyr Tyr Gln Gln Gly Ser Tyr Asn Tyr
            100                 105                 110

Tyr Tyr Tyr Gly Met Asp Val Trp Gly Gln Gly Thr Thr Val Thr Val
            115                 120                 125

Ser Ser
130

```
<210> SEQ ID NO 98
<211> LENGTH: 130
<212> TYPE: PRT
<213> ORGANISM: Artificial Sequence
<220> FEATURE:
<223> OTHER INFORMATION: heavy chain sequence

<400> SEQUENCE: 98
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Asp Arg Gly Thr Tyr Tyr Ile Ala Asp Gly Ser Tyr Asn Tyr
            100                 105                 110

Tyr Tyr Tyr Gly Met Asp Val Trp Gly Gln Gly Thr Thr Val Thr Val
            115                 120                 125

Ser Ser
130

```
<210> SEQ ID NO 99
<211> LENGTH: 130
<212> TYPE: PRT
<213> ORGANISM: Artificial Sequence
<220> FEATURE:
<223> OTHER INFORMATION: heavy chain sequence
```

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Asp Ser Gly Arg Tyr Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 100
<211> LENGTH: 130
<212> TYPE: PRT
<213> ORGANISM: Artificial Sequence
<220> FEATURE:
<223> OTHER INFORMATION: heavy chain sequence

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Gln Glu Gly Ser Tyr Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 101
<211> LENGTH: 130
<212> TYPE: PRT
<213> ORGANISM: Artificial Sequence
<220> FEATURE:
<223> OTHER INFORMATION: heavy chain sequence

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Ile Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Thr Glu Gly Gly Tyr Asn Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 102
<211> LENGTH: 130
<212> TYPE: PRT
<213> ORGANISM: Artificial Sequence
<220> FEATURE:
<223> OTHER INFORMATION: heavy chain sequence

<400> SEQUENCE: 102

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Ile Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Thr Glu Gly Ser Tyr Asn Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 103
<211> LENGTH: 130
<212> TYPE: PRT
<213> ORGANISM: Artificial Sequence
<220> FEATURE:
<223> OTHER INFORMATION: heavy chain sequence

<400> SEQUENCE: 103

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
            50                  55                  60

Lys Gly Arg Phe Thr Ile Ser Arg Asp Ile Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Ala Asp Gly Gly Tyr Asn Tyr
            100                 105                 110

Tyr Tyr Tyr Gly Met Asp Val Trp Gly Gln Gly Thr Thr Val Thr Val
            115                 120                 125

Ser Ser
    130

<210> SEQ ID NO 104
<211> LENGTH: 130
<212> TYPE: PRT
<213> ORGANISM: Artificial Sequence
<220> FEATURE:
<223> OTHER INFORMATION: heavy chain sequence

<400> SEQUENCE: 104

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ile Thr Phe Ser Ser Tyr
             20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
            50                  55                  60

Lys Gly Arg Phe Thr Ile Ser Arg Asp Ile Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Tyr Gln Asp Gly Asn Tyr Asn Tyr
            100                 105                 110

Tyr Tyr Tyr Gly Met Asp Val Trp Gly Gln Gly Thr Thr Val Thr Val
            115                 120                 125

Ser Ser
    130

<210> SEQ ID NO 105
<211> LENGTH: 130
<212> TYPE: PRT
<213> ORGANISM: Artificial Sequence
<220> FEATURE:
<223> OTHER INFORMATION: heavy chain sequence

<400> SEQUENCE: 105

Glu Val Gln Leu Val Glu Ser Gly Gly Gly Leu Val Gln Pro Gly Gly
  1               5                  10                  15

Ser Leu Arg Leu Ser Cys Ala Ala Ser Gly Ile Thr Phe Ser Ser Tyr
             20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
            50                  55                  60

Lys Gly Arg Phe Thr Ile Ser Arg Asp Ile Ala Lys Asn Ser Leu Tyr

```
                65                  70                  75                  80
Leu Gln Met Asn Ser Leu Arg Ala Glu Asp Thr Ala Val Tyr Tyr Cys
                    85                  90                  95

Ala Arg Asp Arg Gly Thr Tyr Tyr Gln Asp Gly Lys Tyr Asn Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 106
<211> LENGTH: 130
<212> TYPE: PRT
<213> ORGANISM: Artificial Sequence
<220> FEATURE:
<223> OTHER INFORMATION: heavy chain sequence

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Asp Arg Gly Thr Tyr Tyr Thr Gly Met Gly Glu Tyr Asn Tyr
                100                 105                 110

Tyr Tyr Tyr Gly Met Asp Val Trp Gly Gln Gly Thr Thr Val Thr Val
            115                 120                 125

Ser Ser
    130

<210> SEQ ID NO 107
<211> LENGTH: 130
<212> TYPE: PRT
<213> ORGANISM: Artificial Sequence
<220> FEATURE:
<223> OTHER INFORMATION: heavy chain sequence

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                    85                  90                  95
```

```
Ala Arg Asp Arg Gly Thr Tyr Tyr Tyr Ala Asp Gly Asp Tyr Asn Tyr
            100                 105                 110

Tyr Tyr Tyr Gly Met Asp Val Trp Gly Gln Gly Thr Thr Val Thr Val
        115                 120                 125

Ser Ser
    130

<210> SEQ ID NO 108
<211> LENGTH: 130
<212> TYPE: PRT
<213> ORGANISM: Artificial Sequence
<220> FEATURE:
<223> OTHER INFORMATION: heavy chain sequence

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Ile Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Thr Tyr Tyr Ala Ser Gly Lys Tyr Asn Tyr
            100                 105                 110

Tyr Tyr Tyr Gly Met Asp Val Trp Gly Gln Gly Thr Thr Val Thr Val
        115                 120                 125

Ser Ser
    130
```